US006310073B1

(12) United States Patent
Kisilevsky et al.

(10) Patent No.: US 6,310,073 B1
(45) Date of Patent: Oct. 30, 2001

(54) METHODS AND COMPOSITIONS TO TREAT GLYCOSAMINOGLYCAN-ASSOCIATED MOLECULAR INTERACTIONS

(75) Inventors: Robert Kisilevsky, Kingston (CA); Allan M. Green, Cambridge, MA (US); Francine Gervais, Ile Bizard (CA)

(73) Assignees: Queen's University at Kingston, Kingston; Neurochem, Inc., Montreal, both of (CA)

( * ) Notice: Subject to any disclaimer, the term of this patent is extended or adjusted under 35 U.S.C. 154(b) by 0 days.

(21) Appl. No.: 09/362,505

(22) Filed: Jul. 27, 1999

Related U.S. Application Data

(60) Provisional application No. 60/094,454, filed on Jul. 28, 1998.

(51) Int. Cl.[7] .......................... A61K 31/407; A61K 31/47; A61K 31/185; A61K 31/715; A61K 38/02
(52) U.S. Cl. .......................... 514/292; 424/78.17; 514/2; 514/54; 514/183; 514/307; 514/553; 514/578; 546/85; 546/150; 562/101; 562/104
(58) Field of Search .......................... 404/78.17; 514/2, 514/23, 53, 54, 183, 553, 576, 577, 578, 292, 307; 546/85, 150; 562/101, 104

(56) References Cited

U.S. PATENT DOCUMENTS

| | | | |
|---|---|---|---|
| 4,091,202 | * 5/1978 | Umezawa et al. | 536/13.7 |
| 4,386,081 | 5/1983 | Helgstrand et al. | 424/212 |
| 4,430,500 | * 2/1984 | Saito et al. | 544/25 |
| 4,540,564 | 9/1985 | Bodor | 424/9 |
| 4,591,583 | 5/1986 | Helgstrand et al. | 514/120 |
| 4,883,666 | 11/1989 | Sabel et al. | 424/422 |
| 5,166,320 | 11/1992 | Wu et al. | 530/395 |
| 5,194,654 | 3/1993 | Hostetler et al. | 558/152 |
| 5,242,932 | 9/1993 | Gandy et al. | 514/313 |
| 5,276,059 | 1/1994 | Caughey et al. | 514/647 |
| 5,385,915 | 1/1995 | Buxbaum et al. | 514/313 |
| 5,389,623 | 2/1995 | Bodor | 514/169 |
| 5,455,044 | 10/1995 | Kim et al. | 424/450 |
| 5,463,092 | 10/1995 | Hostetler et al. | 554/40 |
| 5,494,932 | * 2/1996 | Cardin et al. | 514/514 |
| 5,576,018 | 11/1996 | Kim et al. | 424/450 |
| 5,643,562 | * 7/1997 | Kisilevsky et al. | 424/78.31 |
| 5,658,886 | * 8/1997 | Chizhov et al. | 514/25 |
| 5,668,117 | 9/1997 | Shapiro | 514/55 |
| 5,840,294 | * 11/1998 | Kisilevsky et al. | 424/78.31 |
| 5,869,469 | 2/1999 | Szarek et al. | 514/120 |
| 5,888,973 | * 3/1999 | Lambert, Jr. | 514/12 |

FOREIGN PATENT DOCUMENTS

| | | |
|---|---|---|
| 115 657 | 8/1984 | (EP) . |
| 464 759 | 1/1992 | (EP) . |
| 497 341 | 8/1992 | (EP) . |
| 2669535 | 5/1992 | (FR) . |
| 90/08541 | * 8/1990 | (WO) . |
| WO 94/15624 | 7/1994 | (WO) . |
| WO 94/22437 | 10/1994 | (WO) . |
| 95/06477 | * 3/1995 | (WO) . |
| WO 95/34595 | 12/1995 | (WO) . |
| WO 96/28187 | 9/1996 | (WO) . |
| WO 99/08685 | 2/1999 | (WO) . |
| WO 99/40909 | 8/1999 | (WO) . |

OTHER PUBLICATIONS

West Derwent Abstract, Derwnet–Acc–No: 1998–608151. Abstract of Russian Patent 2,111,962, published May 27, 1998.*

(List continued on next page.)

*Primary Examiner*—Jeffrey E. Russel
(74) *Attorney, Agent, or Firm*—Lahive & Cockfield, LLP; Elizabeth A. Hanley; Nicholas P. Triano, III

(57) ABSTRACT

Therapeutic compounds and methods for inhibiting a glycosaminoglycan (GAG)-associated molecular interaction in a subject, whatever its clinical setting, are described.

5 Claims, 20 Drawing Sheets

OTHER PUBLICATIONS

Ancsin, John B. and Kisilevsky, Robert "The Heparin/Heparan Sulfate–binding Site on Apo–serum Amyloid A" *J. Biol. Chem.* 274(11):7172–81 (1999).

Axelrad et al. "Further Characterization of Amyloid Enhancing Factor" *Laboratory Investigation* 47:139–146 (1982).

Banfield, Bruce W. et al. "Evidence for an Interaction of Herpes Simplex Virus with Chondroitin Sulfate proteoglycans during infection" *Virology* 208:531–39 (1995).

Beadle, J.R. et al. "Alkylthioglycerol prodrugs of foscarnet: synthesis, oral bioavailability and structure–activity studies in human cytomegalovirus–, herpes simplex virus type 1–and human immunodeficiency virus type 1–infected cells" *Antiviral Chem. & Chemother.* 9(1):33–40 (1998).

Bergey, Earl. J., and Stinson, Murray W. "Heparin–Inhibitable Basement Membrane–Binding Protein of *Streptococcus pyogenes*" *Infection & Immunity* 56(7):1715–21 (1988).

Birkelund, Svend et al. "*Chlamydia trachomatis* Serovar L2 Induces Protein Tyrosine Phosphorylation during uptake by HeLa Cells" *Infection & Immunity* 62(11):4900–08 (1994).

Brissette et al. "Differential Induction of the Serum Amyloid A Gene Family in Response to an Inflammatory Agent and to Amyloid–enhancing Factor" *The Journal of Biological Chemistry* 264(32):19327–19332 (1989).

Caughey, B. and Raymond, G. J. "Sulfated Polyanion Inhibition of Scrapie–Associated PrP Accumulation in Cultured Cells" *Journal of Virology* 67(2):643–650 (1993).

Caughey, B. et al. "Binding of the Protease–Sensitive Form of Prion Protein PrP to Sulfated Glysocaminoglycan and Congo Red" *Journal of Virology* 68:2135–2141 (1994).

Caughey, B. "Scrapie–associated PrP accumulation and its prevention: insights from cell culture" *British Medical Bulletin* 49:860–872 (1993).

Caughey, B. "Protease–resistant PrP accumulation and scrapie agent replication: a role for sulphated glycosaminoglycans?" *Biochem. Soc. Trans.*:22:163–167 (1994).

Caughey, B. "Scrapie–associated PrP accumulation and agent replication: effects of sulphated glycosaminoglycan analogues", *Phil. Trans. R. Soc. Lond. B.* 343:399–404 (1994).

Clark, Diana L. et al. "Saccharide anions as inhibitors of the malaria parasite" *Glycoconjugate J.* 14:473–79 (1997).

Copani, A., et al. "Activation of metabotropic glutamate receptors protects cultured neurons against apoptosis induced by β–amyloid peptide" *Molecular Pharmocology* 47(5):890–897 (1995).

Dow et al. "Effects of 4–deoxy–L–threo–pentose, a novel carbohydrate, on neural cell proteoglycan synthesis and function" *Biochimica et Biophysica Acta* 1156:7–14 (1992).

Ehlers et al. "Dextran Sulphate 500 Delays and Prevents Mouse Scrapie by Impairment of Agent Replication in Spleen" *J. Gen. Virol.* 65:1325–1330 (1984).

Fraser et al. "Effects of Sulphate Ions on Alzheimer–beta/A4 Peptide Assemblies: Implications for Amyloid Fibril–Proteoglycan Interactions" *J. Neurochem.* 59:1531–1540 (1992).

Frevert, Ute et al. "Malaria Circumsporozoite Protein Binds to Heparan Sulfate Proteoglycans Associated with the Surface Membrane of Hepatocytes" *J. Exp. Med.* 177:1287–98 (1993).

Fujii, Akira and Cook, Elton S. "Probiotics. Antistaphlococcal and Antifibrinolytic Activities of ω–Amino–and ω–Guanidinoalkanesulfonic Acids" *J. Medicinal Chem.* 18(5):502–05 (1975).

Fujii, Akira et al. "Probiotics. Antistaphylococcal Activity of Aminocyclohexanecarboxylic Acid, 4–Aminobenzoic Acid, and Their Derivatives and Structure–Activity Relationships" *J. Pharmaceut. Sci.* 66(6):844–48 (1977).

Helgstrand, E. et al. "Antiviral Effects of Phosphonoforic Acid and Its Derivatives" *Current Chemotherapy & Infectious. Dis.* 2:1359–61 (1980).

Helgstrand, E. et al. "Trisodium Phosphonoformate, a New Antiviral Compound" *Science* 4358:819–21 (1978).

James, G. et al. "Benzodiazepine Peptidomimetics: Potent Inhibitors of Ras Farnesylation in Animal Cells" *Science* 260:1937–1942 (1993).

Kagan, D.Z. and Rozinova, V.N. "Inhibition of amyloidosis with Congo Red in experimental amyloidosis" *Problemy Tuberkuleza* 40:72–74 (1974) ( with English translation).

Kari, Bruce and Gehrz, Richard "A Human Cytomegalovirus Glycoprotein Complex Designated gC–II Is a Major Heparin–Binding Component of the Envelope" *J. Virology* 66(3):1761–64 (1992).

Kisilevsky, R. "From arthritis to Alzheimer's disease: current concepts of the pathogenesis of amyloidosis" *Can. J. Physiol. Pharmacol.* 65:1805–1815 (1987).

Kisilevsky, R. "Theme and Variations on a String of Amyloid" *Neurobiology of Aging* 10:499–500 (1989).

Kisilevsky, R. "Heparan Sulfate Proteoglycans in Amyloidogenesis: An Epiphenomenon, A Unique Factor, or the Tip of a More Fundamental Process?" *Laboratory Investigation* 63(5):589–591 (1990).

Kisilevsky, R. and Show, A. "The Potential Significance of Sulphated Glycosaminoglycans as a Common Constituent of all Amyloids: or Perhaps Amyloid Is Not a Misnomer" *Medical Hypotheses* 26:231–236 (1988).

Kisilevsky, R. et al. "A Critical Analysis of Postulated Pathogenetic Mechanisms in Amyloidogenesis" *Critical Reviews in Clinical Laboratory Sciences* 29(1):59–82 (1992).

Kisilevsky, R. et al. "Arresting amyloidosis in vivo using small–molecule anoinic sulphonates or sulphates: implications for Alzheimer's disease" *Nature Med.* 1:143–148 (1995).

Krivan, Howard C. et al. "Adhesion of *Mycoplasma pneumoniae* to Sulfated Glycolipids and Inhibition by Dextran Sulfate" *J. Biol. Chem.* 264(16):9283–88 (1989).

Lacoste, Anne–Marie, et al. "Inhibition of D–Alanyl–D–Alanine Ligase in Different Bacterial Species by Amino Phosphonic Acids" *Current Microbiol.* 2(2):113–17 (1979).

Leveugle, B. et al. "Binding of heparan sulfate glycosaminoglycan to beta–amyloid peptide: inhibition by potentially therapeutic polysulfated compounds" *NeuroReport* 5:1389–1392 (1994).

Lycke, Erik et al. "Binding of herpes simplex virus to cellular heparan sulphate, an initial step in the adsorption process" *J. Gen. Virology* 72:1131–37 (1991).

Lyon et al. "Co–deposition of Basement Membrane Components during the Induction of Murine Splenic AA Amyloid" *Laboratory Investigation* 64(6):785–790 (1991).

Masuda et al. "Effect of taurine on nonspecific protection against bacterial infection" Database Chemlabs Online Chemical Abtsracts Service, Accession No. 105:108004 (1985)(Abstract only).

McCubbin et al. "Circular–dichroism studies on two murine serum amyloid A proteins" *Biochem. J.* 256:775–783 (1988).

Narindrasorasak et al. "High Affinity Interactions between the Alzheimer's Beta–Amyloid Precursor Proteins and the Basement Membrane Form of Heparan Sulfate Proteoglycan" *The journal of Biological Chemistry* 266(20):12878–12883 (1991).

Narindrasorasak et al. "Characterization of High Affinity Binding between Laminin and Alzheimer's Disease Amyloid Precursor Proteins" *Laboratory Investigation* 67(5):643–652 (1992).

Neyts, Johan et al. "Sulfated Polymers Inhibit the Interaction of Human Cytomegalovirus with Cell Surface Heparan Sulfate" *Virology* 189:48–58 (1992).

Norén, Jan O. et al. "Synthesis of Esters of Phosphonoformic Acid and Their Antiherpes Activity" *J. Med. Chem.* 26:264–70 (1983).

Ortega–Barria, Eduardo and Pereira, Miercio E.A. "A Novel T. cruzi Heparin–Binding Protein Promotes Fibroblast Adhesion and Penetration of Engineered Bacteria and Trypanosomes into Mammalian Cells" *Cell* 67:411–21 (1991).

Prescott, Lawrence M. "Highlights of the 32$^{nd}$ Interscience Conference on Antimicrobal Agents and Chemotherapy" *Drug Therapy* 23(4):56–58 (1993).

Puchtler et al. "Application of Thiazole Dyes to Amyloid under Conditions of Direct Cotton Dyeing: Correlation of Histochemical and Chemical Data" *Histochemistry* 77: 431–445 (1983).

Rogerson S.J. and Brown G.V. "Chondroitin Sulphate A as an Adherence Receptor for *Plasmodium falciparum*–infected Erythrocytes" *Parasitology Today* 13(2):70–75 (1997).

Rogerson, Stephen J. et al. "Chondroitin Sulfate A Is a Cell Surface Receptor for *Plasmodium falciparum*–infected Erythrocytes" *J. Exp. Med.* 182:15–20 (1995).

Schwers, A. et al. "Comparison of the Effect of Trisodium Phosphonoformate on the Mean Plaque Size of Pseudorabies Virus, Infectious Bovine Rhinotracheitis Virus and Pigeon Herpesvirus" *J. Comp. Path.* 90(4):625–33 (1980).

Shakibaei, Mehdi and Frevert, Ute "Dual Interaction of the Malaria Circumsporozoite Protein with the Low Density Lipoprotein Receptor–related Protein (LRP) and Heparan Sulfate Proteoglycans" *J. Exp. Med.* 184:1699–1711 (1996).

Shieh, Mei–Tsu et al. "Cell Surface Receptors for Herpes Simplex Virus Are Heparan Sulfate Proteoglycans" *J. Cell. Biol.* 116(5):1273–81 (1992).

Sinnis, Photini and Sim, B. Kim Lee "Cell invasion by the vertebrate stages of Plasmodium" *Trends in Microbiol.* 5(2):52–58 (1997).

Sinnis, Photini et al. "Remnant Lipoproteins Inhibit Malaria Sporozoite Invasion of Hepatocytes" *J. Exp. Med.* 184:945–954 (1996).

Small, D.H. et al. "Association and Release of the Amyloid Protein Precursor of Alzheimer's Disease from Chick Brain Extracellular Matrix" *The Journal of Neuroscience* 12(11):4143–4150 (1992).

Snow et al. "A Close Ultrastructural Relationship between Sulfated Proteoglycans and AA Amyloid Fibrils" *Laboratory Investigation* 57(6):687–697 (1987).

Snow et al. "Characterization of Tissue and Plasma Glycosaminoglycans during Experimental AA Amyloidosis and Acute Inflammation" *Laboratory Investigation* 56(6):665–675 (1987).

Snow et al. "Sulfated Glycosaminoglycans in Alzheimer's Disease" *Human Pathology* 18(5):506–510 (1987).

Snow et al. "Sulfated Glycosaminoglycans: A Common Constituent of All Amyloids?" *Laboratory Investigation* 56(1):120–123 (1987).

Snow et al. "Sulfated glycosaminoglycans in amyloid plaques of prion diseases" *Acta Neuropathol.* 77:337–342 (1989).

Snow et al. "A Temporal and Ultrastructural Relationship Between Heparan Sulfate Proteoglycans and AA Amyloid in Experimental Amyloidosis", *The Journal of Histochemistry and Cytochemistry* 39(10):1321–1330 (1991).

Snow, A. D. and Kisilevsky R. "Temporal Relationship between Glycosaminoglycan Accumulation and Amyloid Deposition during Experimental Amyloidosis" *Laboratory Investigation* 53(1):37–43 (1985).

Svennerholm, Bo et al. "Inhibition of Herpes Simplex Virus Infection in Tissue Culture by Trisodium Phosphonoformate" *Proceed. Soc. Experimental Biol & Med.* 161(2):115–18 (1979).

Tape et al. "Direct Evidence for Circulating apoSAA as the Precursor of Tissue AA Amyloid Deposits" *Scand. J. Immunol.* 28:317–324 (1988).

Thornton, D.M. "The synthesis of novel pyrophosphate analogues and their antiviral activities" *Dissertation Abstracts Int'l.* 51(05–B,:2372 (1989) (retrieved online from Dialog File 35, Accession No. 01123106)(Abstract only).

Travis, John "New Piece in Alzheimer's Puzzle" *Science* 261:828–829 (1993).

Winters, Bradford D. et al. "Isolation and Characterization of a *Streptococcus pyogenes* Protein That Binds Laminae of Human Cardiac Muscle" *Infection & Immunity* 61(8):3259–64 (1993).

Wong et al. "Influence of Sulphate Ions on the Structure of AA Amyloid Fibrils" *Scand. J. Immunol.* 32:225–232 (1990).

WuDunn, Darrell and Spear, Patricia G. "Initial Interaction of Herpes Simplex Virus with Cells Is Binding to Heparan Sulfate" *J. Virology* 63(1):52–58 (1989).

Xiao, Lihua et al. "Sulfated Polyanions Inhibit Invasion of Erythrocytes by Plasmodial Merozoites and Cytoadherence of Endothelial Cells to Parasitized Erythrocytes" *Infection & Immunity* 64(4):1373–78 (1996).

Young et al. "Localization of the Basement Membrane Heparan Sulfate Proteoglycan in Islet Amyloid Deposits in Type II Diabetes Mellitus" *Arch Pathol. Lab. Med.* 116:951–954 (1992).

Young et al. "The ultrastructural localization of sulfated proteoglycans is identical in the amyloids of Alzheimer's disease and AA, AL, senile cardiac and medullary carcinoma–associated amyloidosis" *Acta Neuropathol.* 78:202–209 (1989).

Zaretzky, Franca R. et al. "Sulfated Polyanions Block *Chlamydia trachomatis* Infection of Cervix–Derived Human Epithelia" *Infection & Immunity* 63(9):3520–26 (1995).

* cited by examiner

AcNHCH$_2$CH$_2$CH$_2$SO$_3$Na

BzNHCH$_2$CH$_2$CH$_2$SO$_3$Na

XXI

XXII

XXIII

XXIV

XXV

XXVI

XXVII

XXVIII

XXIX

XXX

XXXI

XXXII

XXXIII

XXXIV

XXXV

XXXVI

XXXVII

XXXVIII

XXXIX

XL

XLI
 XLII
 XLIII
 XLIV
 XLV
 XLVI
 XLVII
 XLVIII
 XLIX
 L
 LI
 LII
 LIII
 LIV

LV

LVI

LVII

LVIII

LIX

LX

LXI

LXII

LXIII

LXIV

LXV

LXVI

LXVII

LXVIII

LXIX

LXX

LXXI

LXXII

LXXIII

LXXIV

LXXV

LXXVI

LXXVII

METHODS AND COMPOSITIONS TO TREAT GLYCOSAMINOGLYCAN-ASSOCIATED MOLECULAR INTERACTIONS

RELATED APPLICATIONS

This application claims the benefit of priority under 35 U.S.C. 119(e) to copending U.S. Provisional Application 60/094,454, filed on Jul. 28, 1998, the entire contents of which is incorporated herein by reference.

BACKGROUND OF THE INVENTION

Glycosaminoglycans (GAGs) have been shown to be involved with the early steps of the infectious process associated with several pathogens. For example, it is believed that sulfated proteoglycans are used by the infectious agents as anchors or adsorption moieties for invasion of the host cells. Several bacterial and viral infectious agents have been found to use extracellular membrane components, such as GAGs, to access host cells.

Heparan sulfate and/or other sulfated GAGs have been suggested to be involved in the infection process by certain bacteria such as *Streptococcus pyogenes* associated with acute rheumatic fever and poststreptococcal glomerulonephritis, *Chlamydia trachomatis*, *Staphylococcus aureus* and *Pseudomonas aeruginosa* (cystic fibrosis), *Legionella pneumophila* (Legionnaire's disease), Bordetella pertussis (whooping cough), and Mycoplasma pneumoniae. As one example, *Streptococcus pyogenes* surfaces bind fibronectin, laminin, fibrinogen, nonspecific immunoglobulins A and G, α2-macroglobulin, β2-microglobulin and albumin. Bacterial components do not bind to epithelial or endothelial cells of the kidney but accumulate on the proteoglycan-rich regions that connect these cells to the underlying connective tissue. Another example, *Chlamydia trachomatis*, is one of the most common sexually transmitted bacterial pathogens in the world. Infection appears to be facilitated by binding of a heparan sulfate-like GAG present on the surface of chlamydia, to a heparan sulfate receptor on the target cell.

Certain types of viri, Herpesviridae, are believed to be associated with HSPG during the infectious process. These viri appear to interact with a cells surface through GAGs found on the proteoglycans of the cell plasma membrane. These GAGs are similar to heparin. Cytomegalovirus (CMV) and Herpes simplex (HSV-1 and HSV-2) are two of the viri which are believed to infect cells via cell surface GAGs.

Although certain agents have been used to suppress infection of hosts by pathogens, there are limitations to their use. For example, the widespread use of antibiotics has increasingly led to the problem of resistant pathogens whose growth can no longer be inhibited by known antibiotics. Thus, the appearance of multi-drug resistant pathogens has prompted a search for new classes of compounds which are structurally and/or functionally different from existing drugs. Drugs having new mechanisms of action could be effective against resistant pathogens, where conventional drugs can no longer be used.

SUMMARY OF THE INVENTION

Methods and compositions which are useful in the treatment of conditions related to glycosaminoglycan (GAG)-associated molecular interactions are presented herein.

In one aspect the invention relates to methods for treating a condition related to a glycosaminoglycan-associated molecular interaction in a subject. The method includes administering to the subject a therapeutically effective amount of a therapeutic compound having the formula:

$$Q\text{-}[\text{-}Y^-X^+]_n \qquad (I)$$

wherein $Y^-$ is an anionic group at physiological pH; Q is a carrier molecule; $X^+$ is a cationic group; and n is an integer selected such that the biodistribution of the therapeutic compound for an intended target site is not prevented while maintaining activity of the therapeutic compound, or a pharmaceutically acceptable salt or ester thereof, such that the glycosaminoglycan-associated molecular interaction is modulated and the condition is treated. These methods can be used therapeutically to treat a subject, e.g., afflicted with a pathogen, or can be used prophylactically in a subject susceptible to pathogens.

In another embodiment, the therapeutic compound has at least one anionic group covalently attached to a carrier molecule. In another embodiment, the anionic group covalently attached to the carrier molecule is a sulfonate group. Accordingly, the therapeutic compound can have the formula:

$$Q\text{-}[\text{-}SO_3^-X^+]_n \qquad (II)$$

wherein Q is a carrier molecule; $X^+$ is a cationic group; and n is an integer. In another embodiment, the anionic group is a sulfate group. Accordingly, the therapeutic compound can have the formula:

$$Q\text{-}[\text{-}OSO_3^-X^+]_n \qquad (III)$$

wherein Q is a carrier molecule; $X^+$ is a cationic group; and n is an integer. Carrier molecules which can be used include carbohydrates, polymers, peptides, peptide derivatives, aliphatic groups, alicyclic groups, heterocyclic groups, aromatic groups and combinations thereof.

The invention also provides a method for modulating interactions between an infectious agent and a GAG in a subject. The method includes administering to the subject a therapeutically effective amount of a therapeutic compound having the formula:

$$Q\text{-}[\text{-}Y^-X^+]_n \qquad (I)$$

wherein $Y^-$ is an anionic group at physiological pH; Q is a carrier molecule; $X^+$ is a cationic group; and n is an integer selected such that the biodistribution of the therapeutic compound for an intended target site is not prevented while maintaining activity of the therapeutic compound, or a pharmaceutically acceptable salt or ester thereof.

In another aspect, methods and therapeutic compositions are provided herein for treating a subject afflicted with a disease, e.g., acute rheumatic fever and poststreptococcal glomerulonephritis, caused by infection by bacteria such as *Streptococcus pyogenes*, *Chlamydia trachomatis*, *Staphylococcus aureus*, *Pseudomonas aeruginosa*, *Legionella pneumophila*, *Bordetella pertussis*, and *Mycoplasma pneumoniae*, such that the subject afflicted with the disease is treated. The methods include administering to a subject a therapeutically effective amount of a therapeutic compound of formula (I) for treating the infection. The therapeutic compound is not carrageenan, pentosan polysulfate, fucoidan, dextran sulfate, heparin, heparan sulfate or dermatan sulfate.

In yet another aspect, the invention provides methods and therapeutic compositions for treating a subject afflicted with a disease caused by infection of viri via such as Cytomegalovirus (CMV) and Herpes simplex (HSV-1 and HSV-2), such that the subject afflicted with the disease is treated. The methods include administering to a subject a therapeutically effective amount of a therapeutic compound of formula (I) for treating the disease. The therapeutic compound is not a chondroitin sulfate.

In yet a further aspect a packaged pharmaceutical composition for treating a condition related to a glycosaminoglycan-associated molecular interaction or for modulating a GAG-associated molecular interaction, e.g., between a GAG and an infectious agent, is described herein. The packaged composition includes a container holding a therapeutically effective amount of a pharmaceutical composition for treating the condition related to a glycosaminoglycan-associated molecular interaction in a subject. Alternatively, the packaged composition includes a container holding a therapeutically effective amount of a pharmaceutical composition for modulating a GAG-associated molecular interaction. The pharmaceutical composition includes at least one therapeutic compound having the formula:

$$Q\text{-}[\text{-}Y^-X^+]_n \quad (I)$$

wherein $Y^-$ is an anionic group at physiological pH; Q is a carrier molecule; $X^+$ is a cationic group; and n is an integer selected such that the biodistribution of the therapeutic compound for an intended target site is not prevented while maintaining activity of the therapeutic compound, or a pharmaceutically acceptable salt or ester thereof. Instructions for using the pharmaceutical composition for treatment of the condition related to a glycosaminoglycan-associated molecular interaction or for modulating the GAG-associated molecular interaction are included in the packaged pharmaceutical composition.

The invention further provides pharmaceutical compositions for treating a condition related to a glycosaminoglycan-associated molecular interaction in a subject. Alternatively, the invention provides pharmaceutical compositions for modulating a GAG-associated molecular interaction in a subject. The pharmaceutical compositions include a therapeutically effective amount of a therapeutic compound of the invention, as described supra, and a pharmaceutically acceptable carrier.

In further embodiments, the therapeutic compound has at least one anionic group covalently attached to a carrier molecule. In yet another embodiment, the anionic group covalently attached to the carrier molecule is a sulfonate group. Accordingly, the therapeutic compound can have the formula:

$$Q\text{-}[\text{-}SO_3^-X^+]_n \quad (II)$$

wherein Q is a carrier molecule; $X^+$ is a cationic group; and n is an integer. In another embodiment, the anionic group is a sulfate group. Accordingly, the therapeutic compound can have the formula:

$$Q\text{-}[\text{-}OSO_3^-X^+]_n \quad (III)$$

wherein Q is a carrier molecule; $X^+$ is a cationic group; and n is an integer.

DETAILED DESCRIPTION OF THE INVENTION

Figure 1:
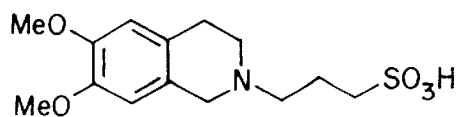
FIGS. 1–14 depict the chemical structures of compounds described in the specification.
Figure 1:
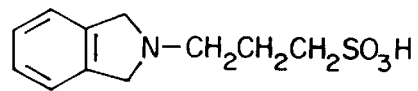
Figure 1:
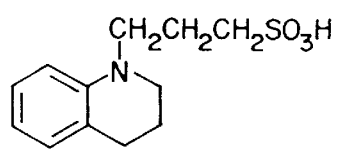
Figure 1:
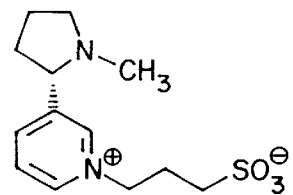
Figure 1:
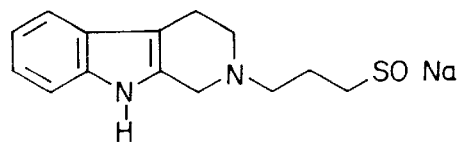
Figure 1:
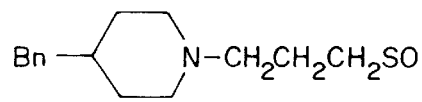
Figure 1:
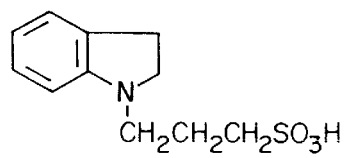
Figure 1:
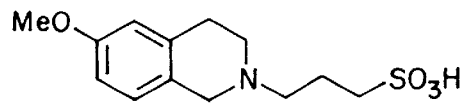
Figure 2:
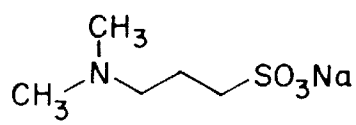
Figure 2:
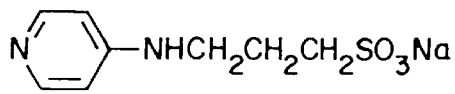
Figure 2:
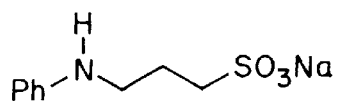
Figure 2:
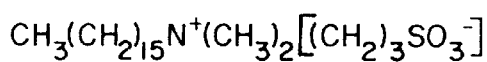
Figure 2:
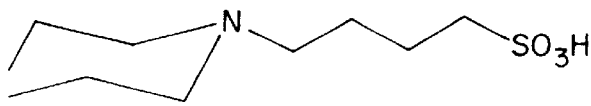
Figure 2:
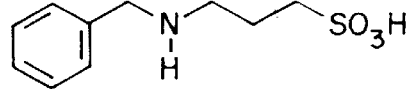
Figure 2:
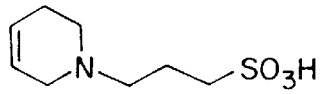
Figure 2:
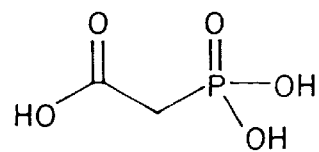
Figure 2:
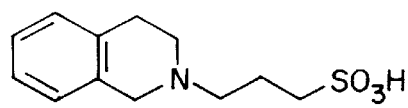
Figure 2:
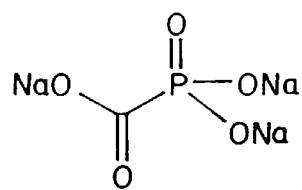
Figure 3:
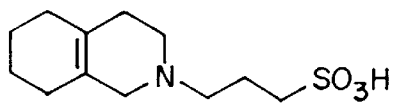
Figure 3:
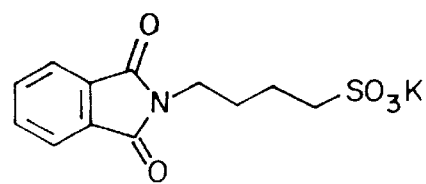
Figure 3:
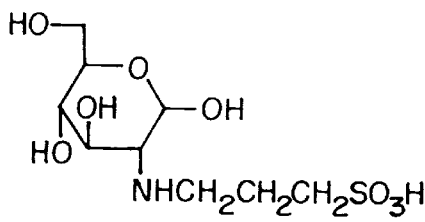
Figure 3:
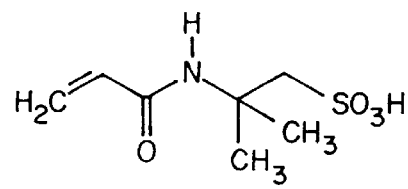
Figure 3:
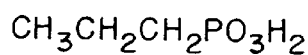
Figure 3:
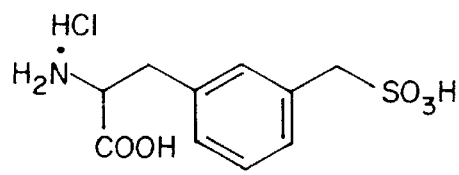
Figure 3:
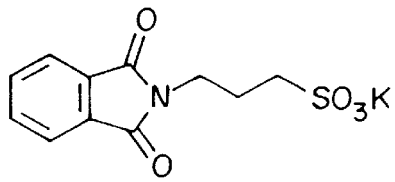
Figure 3:
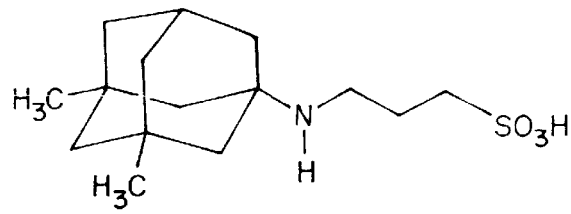
Figure 3:
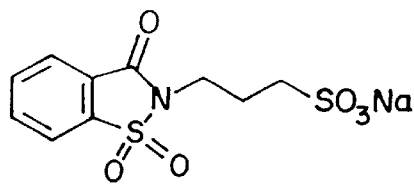
Figure 3:
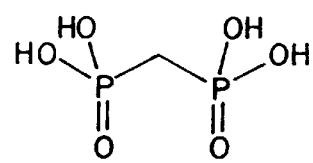
Figure 4:
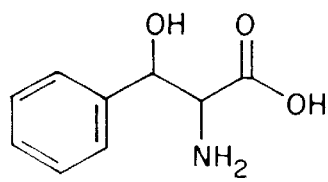
Figure 4:
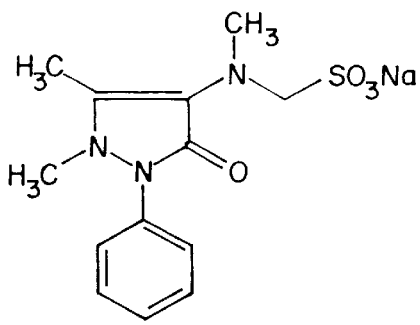
Figure 4:
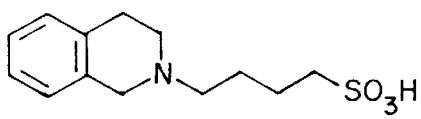
Figure 4:
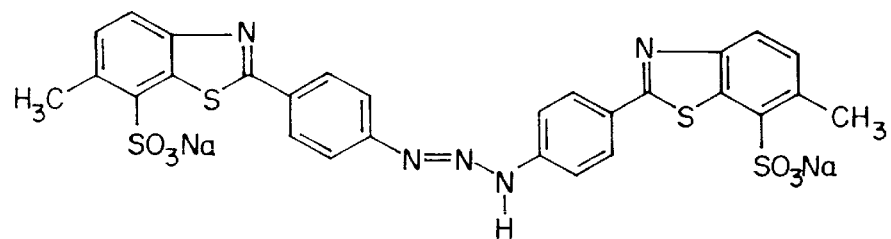
Figure 4:
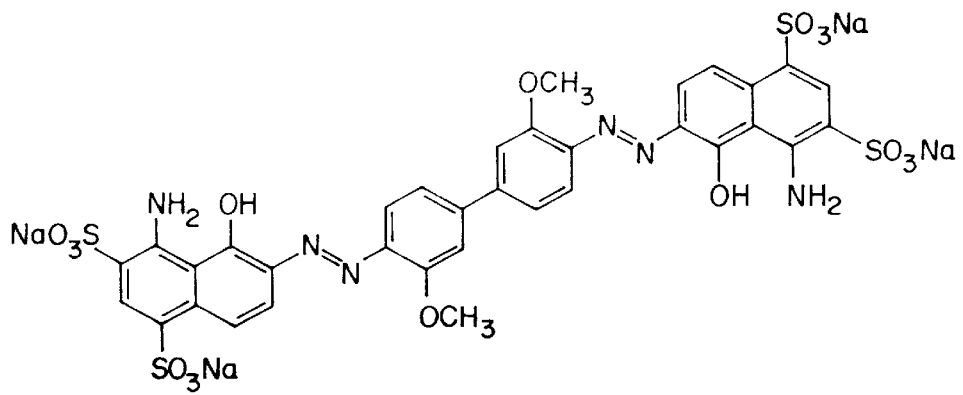
Figure 5:
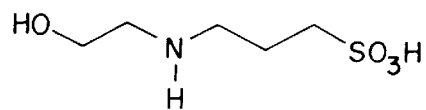
Figure 5:
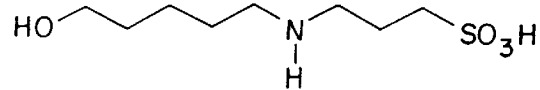
Figure 5:
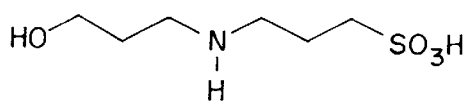
Figure 5:
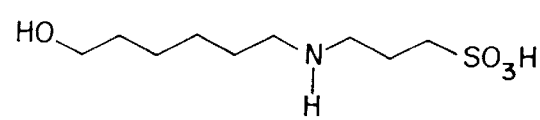
Figure 5:
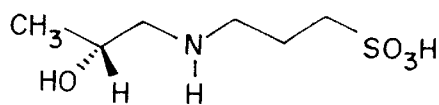
Figure 5:
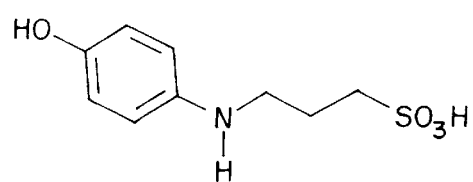
Figure 5:
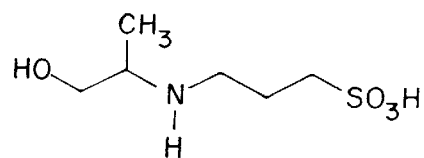
Figure 5:
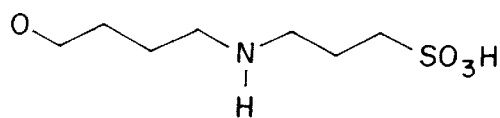
Figure 6:
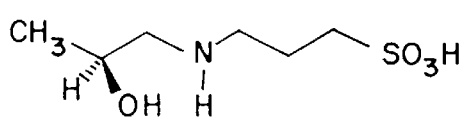
Figure 6:
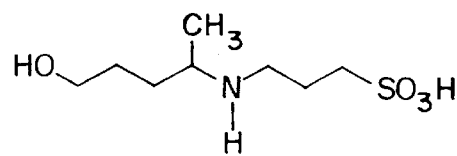
Figure 6:
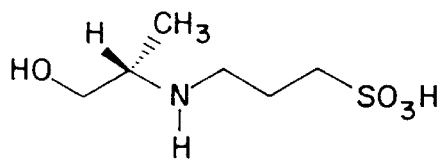
Figure 6:
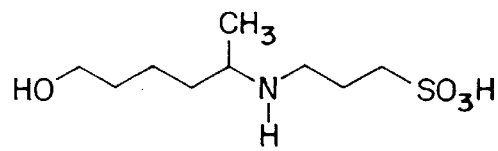
Figure 6:
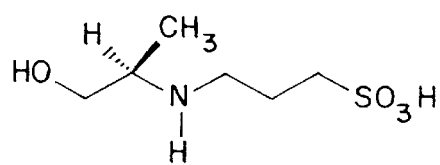
Figure 6:
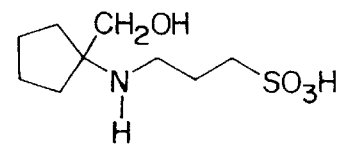
Figure 6:
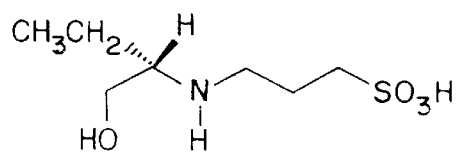
Figure 6:
Figure 6:
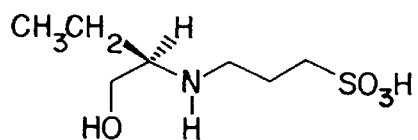
Figure 6:
Figure 7:
Figure 7:
Figure 7:
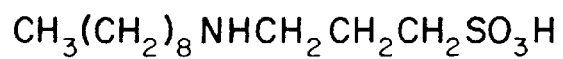
Figure 7:
Figure 7:
Figure 7:
Figure 7:
Figure 8:
Figure 8:
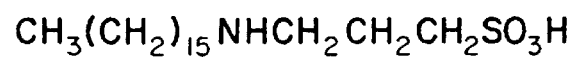
Figure 8:
Figure 9:
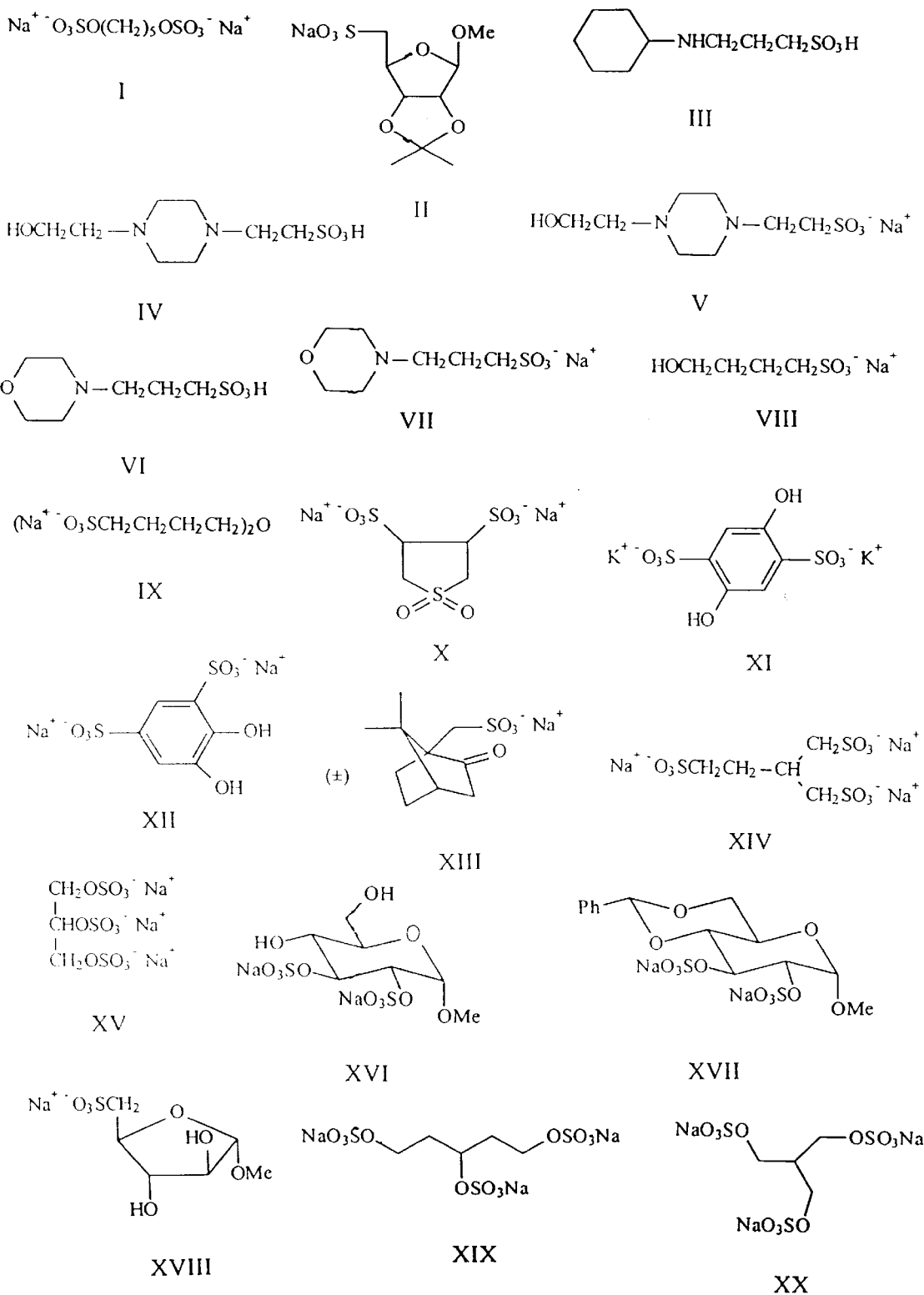
Figure 10:
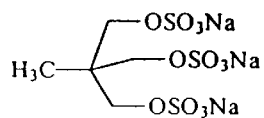
Figure 10:
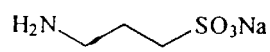
Figure 10:
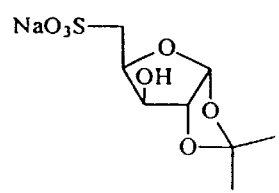
Figure 10:
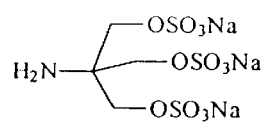
Figure 10:
Figure 10:
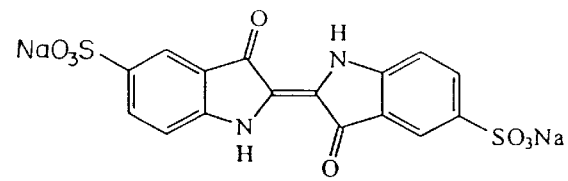
Figure 10:
Figure 10:
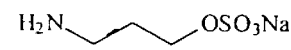
Figure 10:
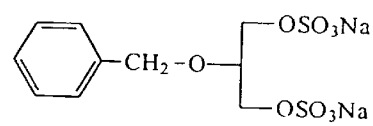
Figure 10:
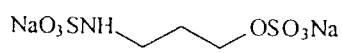
Figure 10:
Figure 10:
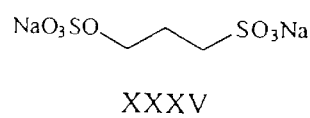
Figure 10:
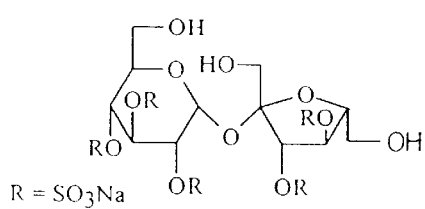
Figure 10:
Figure 10:
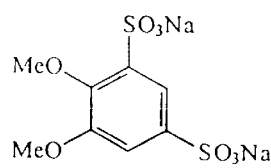
Figure 10:
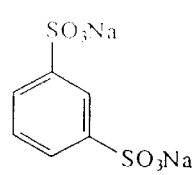
Figure 10:
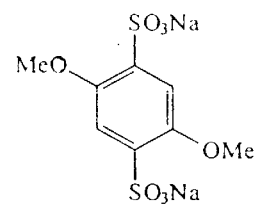
Figure 10:
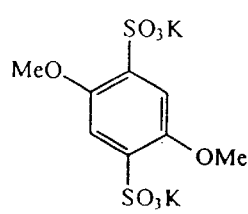
Figure 10:
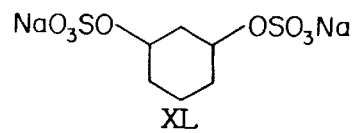
Figure 11:
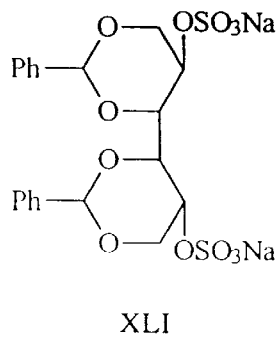
Figure 11:
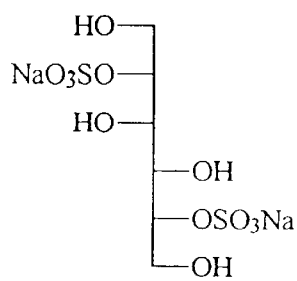
Figure 11:
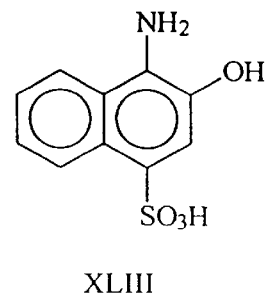
Figure 11:
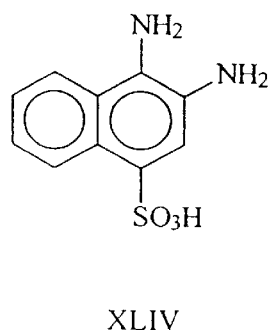
Figure 11:
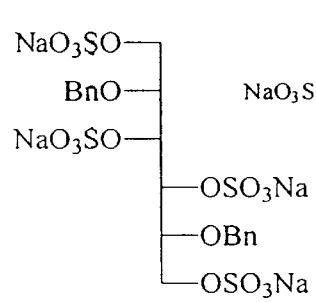
Figure 11:
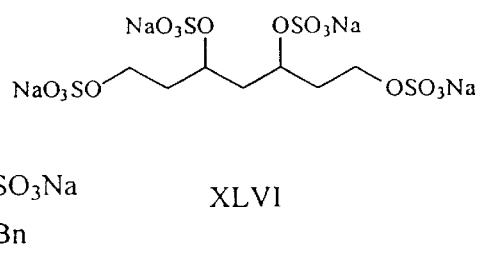
Figure 11:
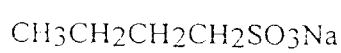
Figure 11:
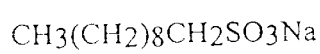
Figure 11:
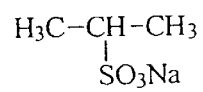
Figure 11:
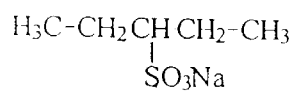
Figure 11:
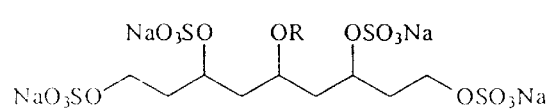
Figure 11:
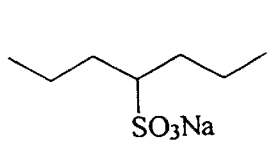
Figure 11:
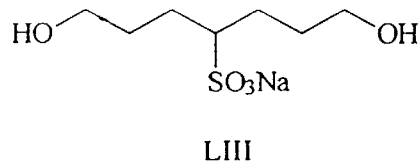
Figure 11:
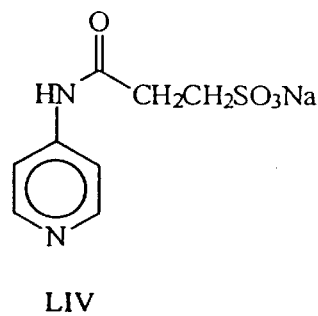
Figure 12:
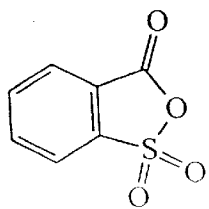
Figure 12:
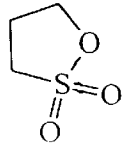
Figure 12:
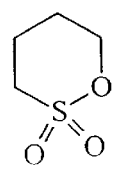
Figure 12:
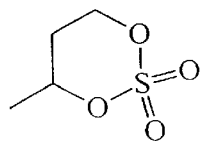
Figure 12:
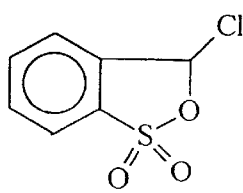
Figure 12:
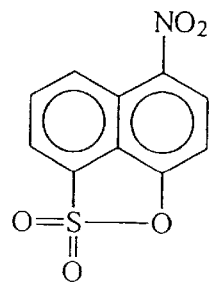
Figure 12:
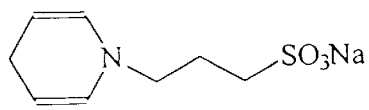
Figure 12:
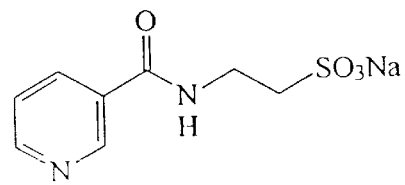
Figure 12:
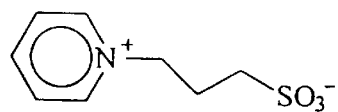
Figure 13:
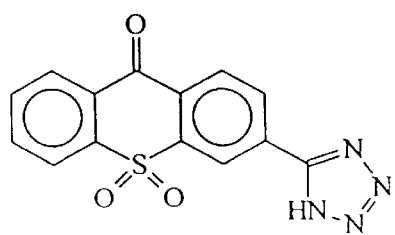
Figure 13:
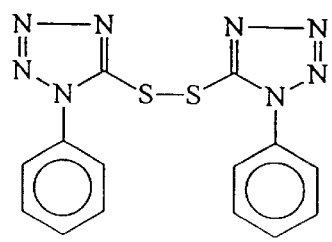
Figure 13:
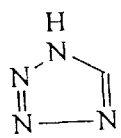
Figure 13:
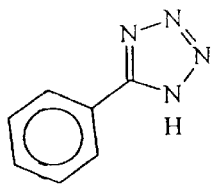
Figure 13:
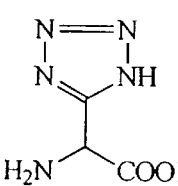
Figure 13:
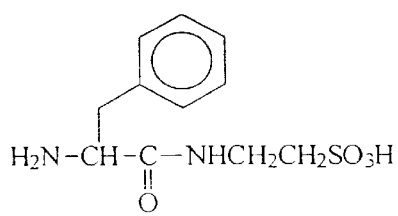
Figure 13:
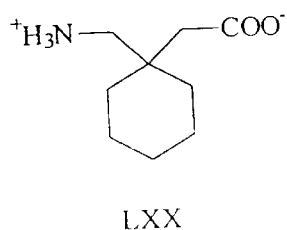
Figure 13:
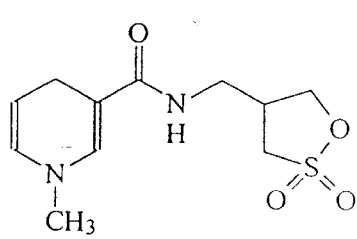
Figure 13:
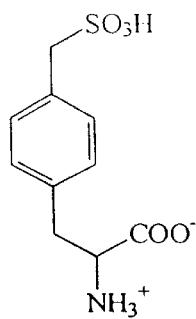
Figure 13:
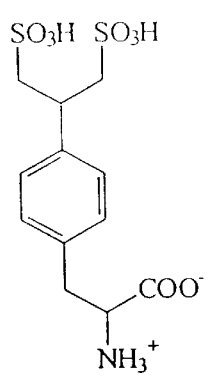
Figure 13:
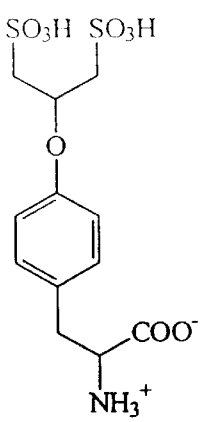
Figure 14:
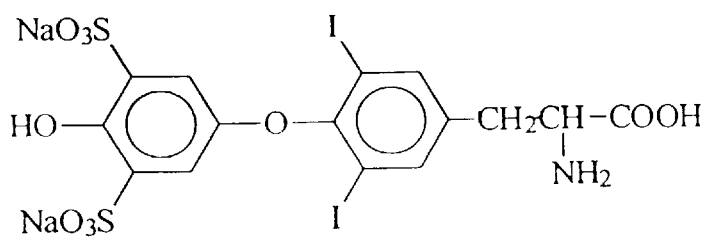
Figure 14:
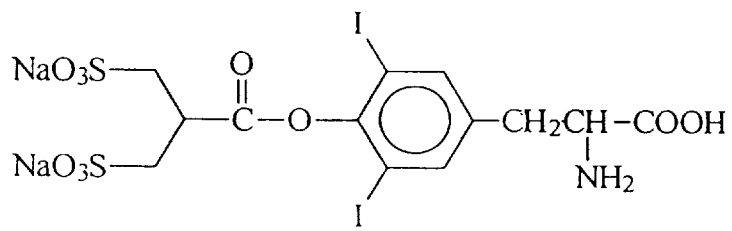
Figure 14:
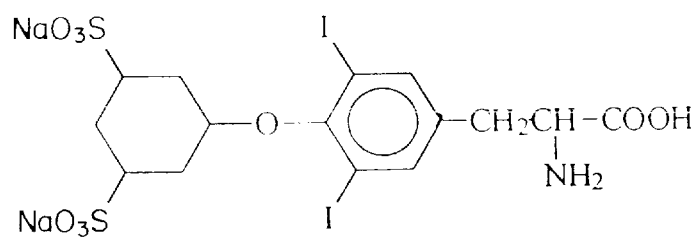
Figure 15:
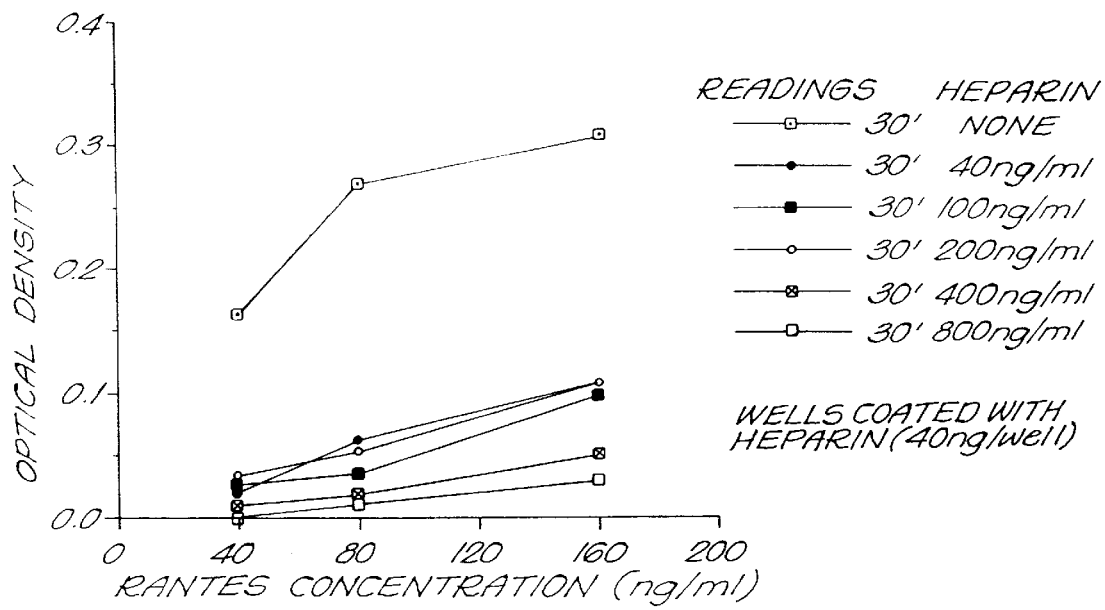
FIGS. 15–28 illustrate the efficacy of compounds of the invention in inhibiting binding of certain compounds, e.g., Rantes, IL-8, to heparan-coated wells. The compounds referenced in the drawings are: 1) 3-amino-1-propanesulfonic acid, sodium salt; 2) trisodium phosphonoformate; 3) methylene diphosphonic acid; 4) trehalose octasulfate, octasodium salt; 5) trans-4-hydroxy-L-proline-4-sulfate, disodium salt; 6) nitrilo(methylene) triphosphonic acid; 7) poly (vinylsulfonate), sodium salt (PVS501, Aldrich); 8) 3-[-2-6-methoxy-1,2,3,4-tetrahydroisoquinolinyl)]-1-propanesulfonic acid; 9) 3-phosphonopropanesulfonic acid, trisodium salt; 10); 4,5-dihydroxy-1,3,benzenedisulfonic acid, sodium salt; 11) 3-cyclohexylamino-1-ropanesulfonic acid; 12) O-phospho-L-serine; and 13) 2-thiopheneboronic acid.
Figure 16:
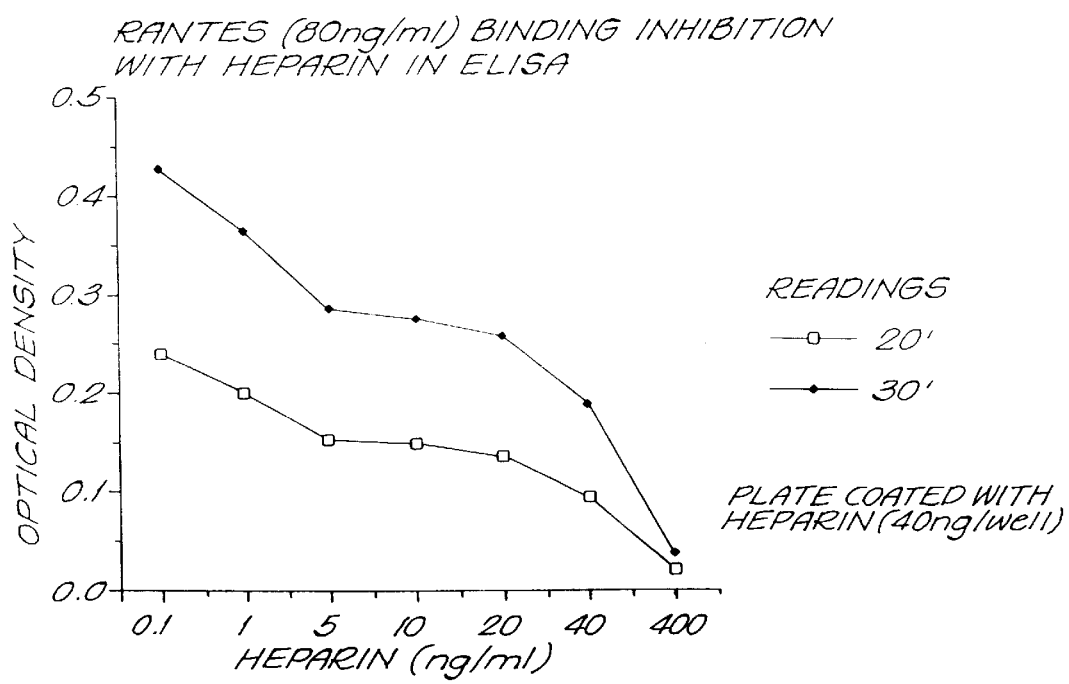
Figure 17:
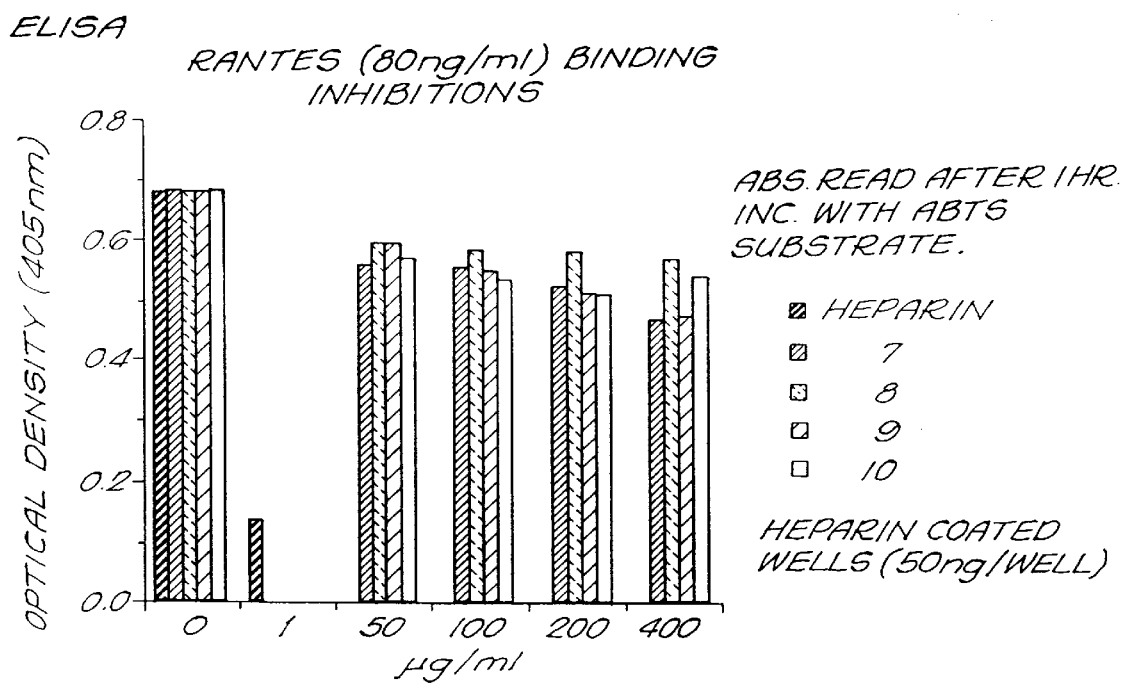
Figure 18:
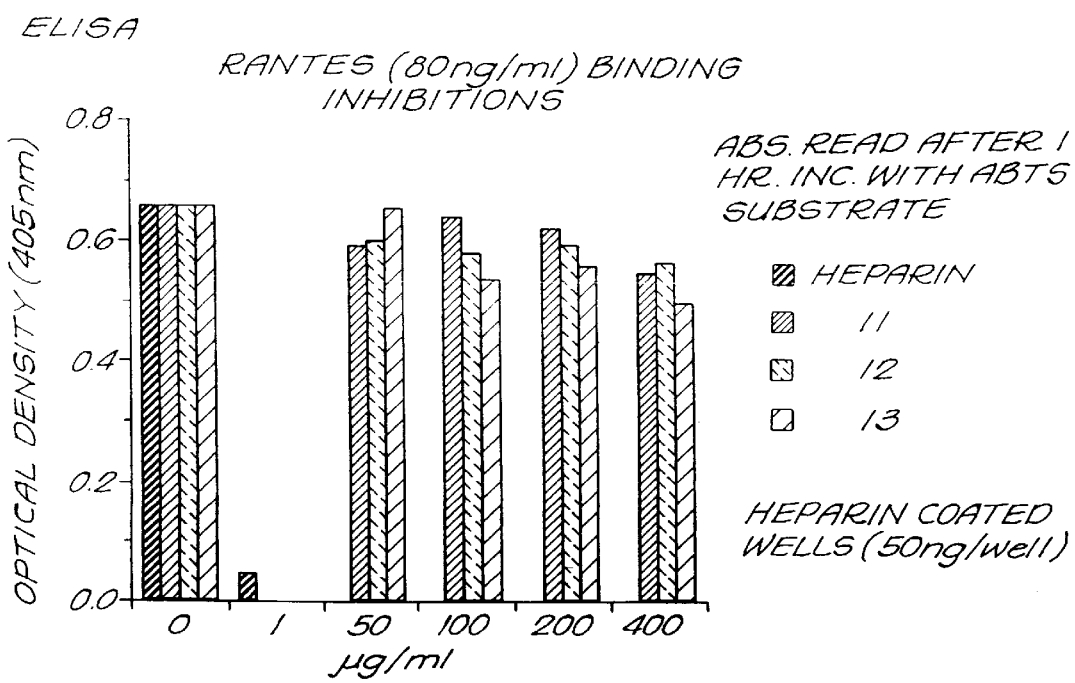
Figure 19:
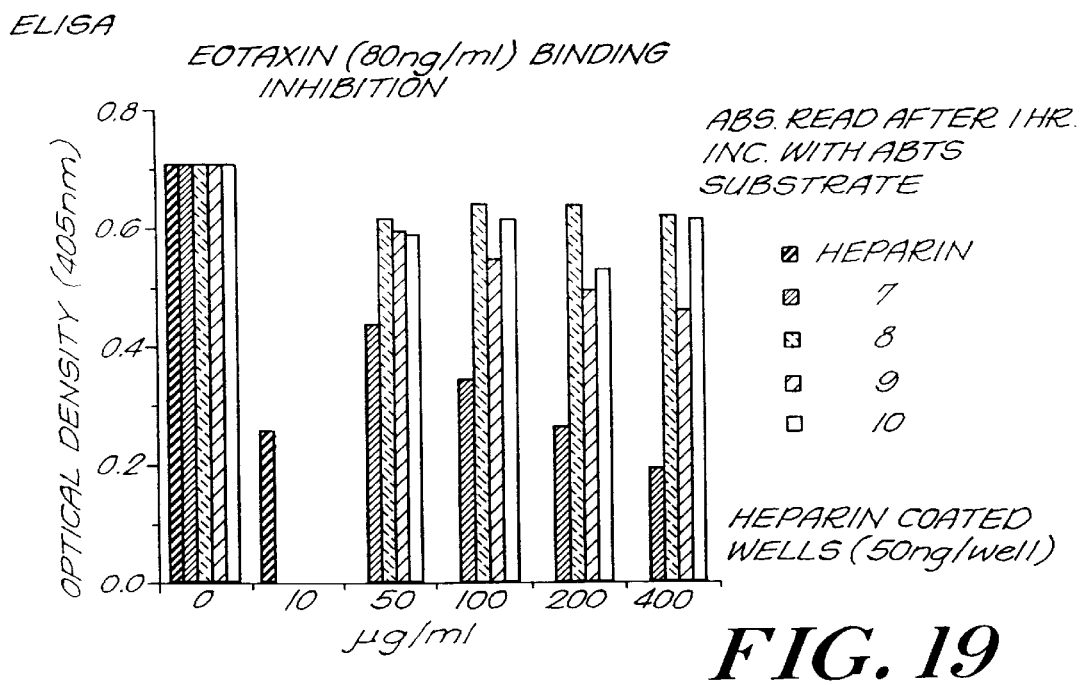
Figure 20:
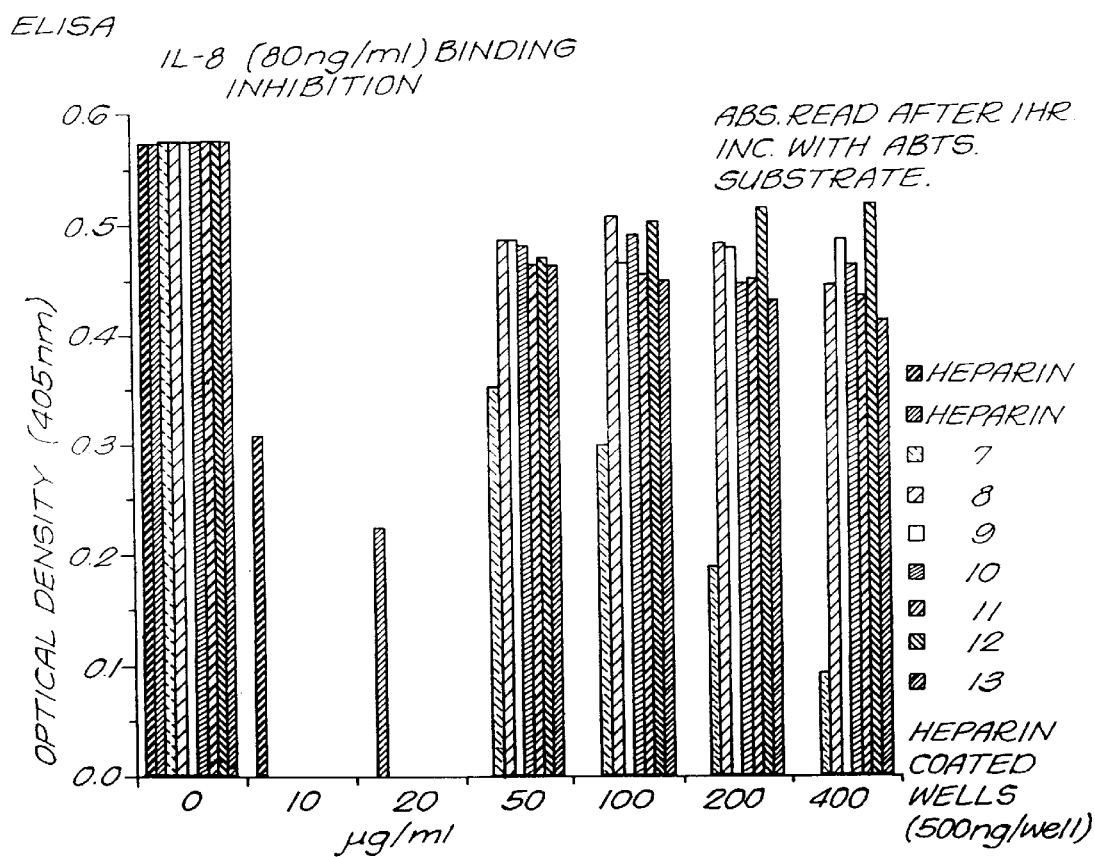
Figure 21:
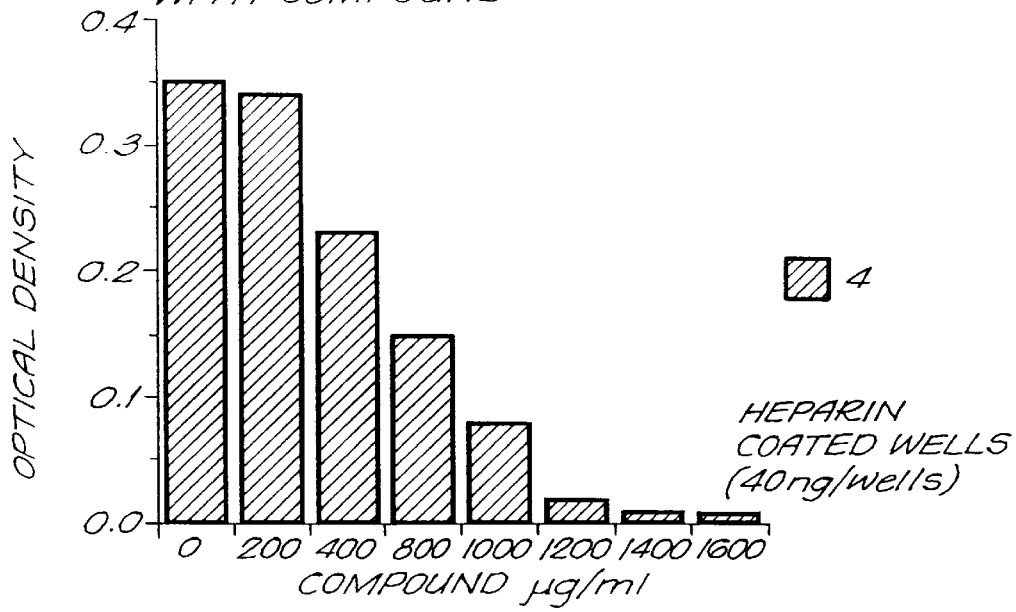
Figure 22:
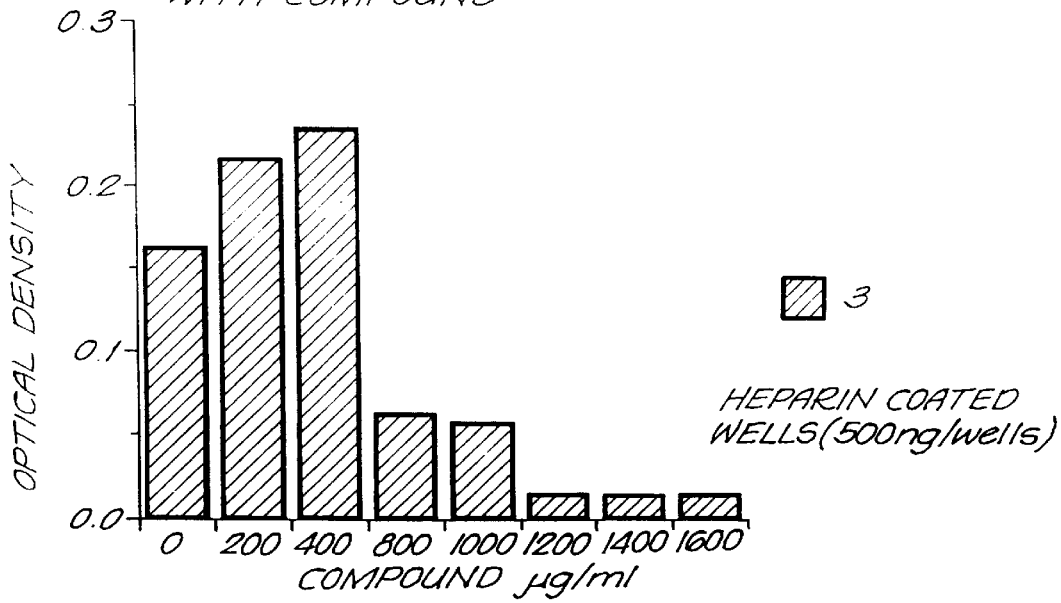
Figure 23:
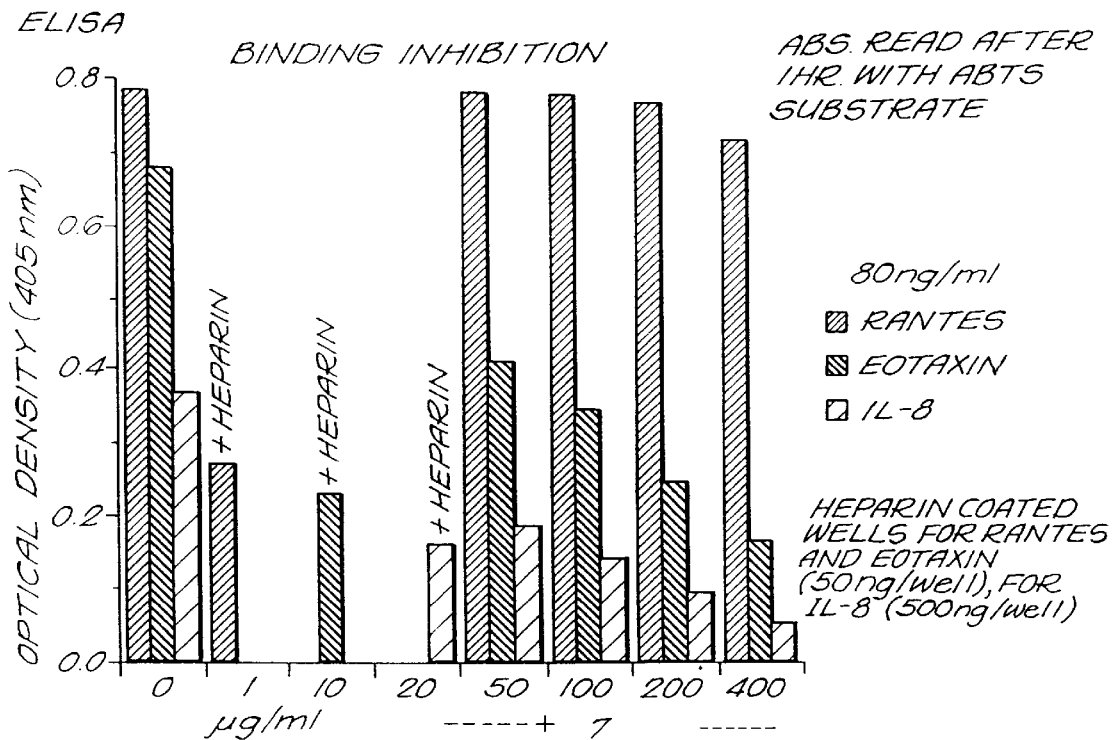
Figure 24:
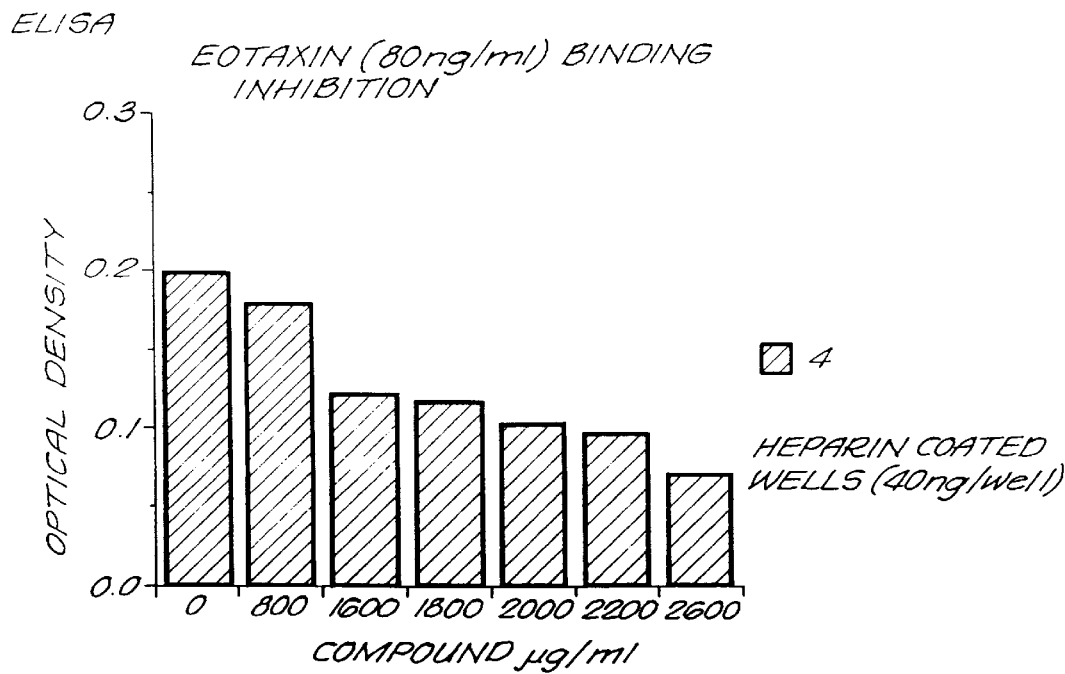
Figure 25:
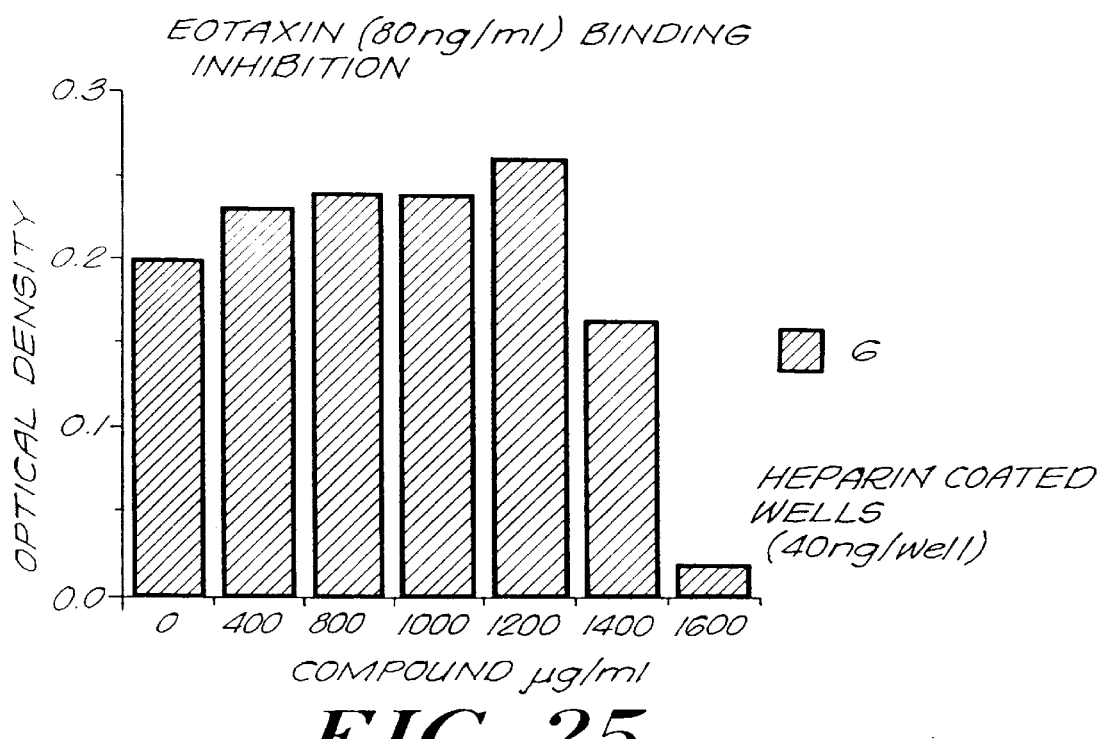
Figure 26:
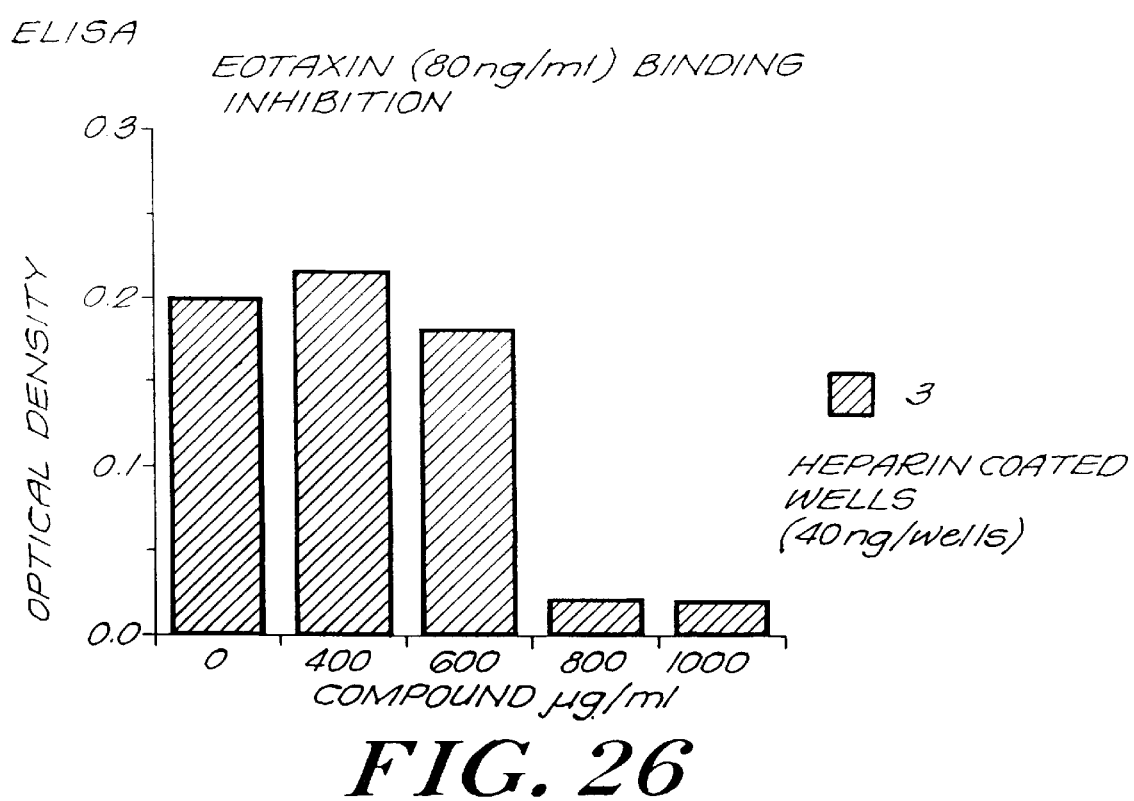
Figure 27:
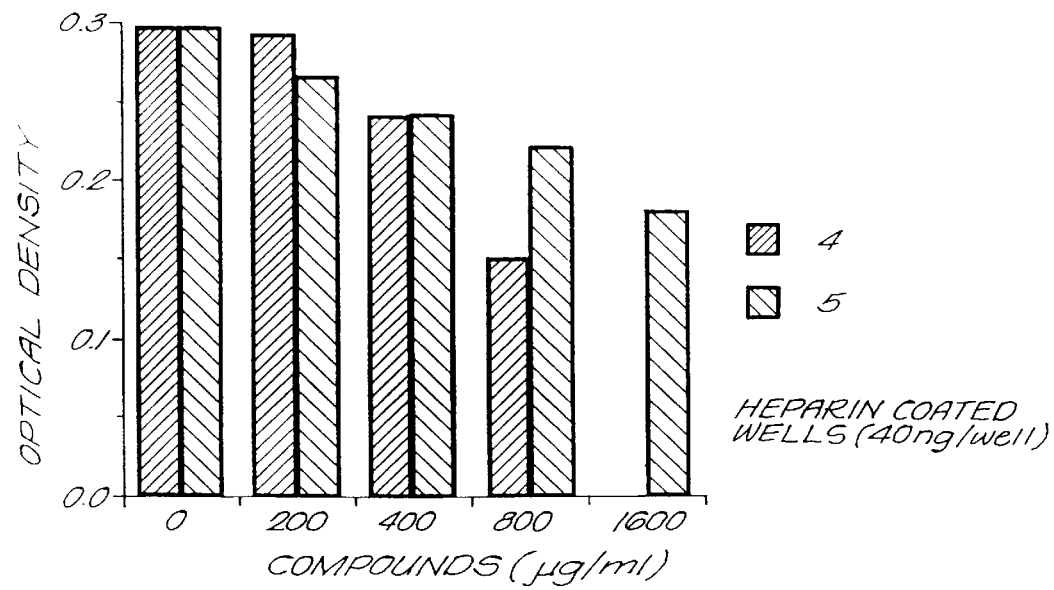
Figure 28:
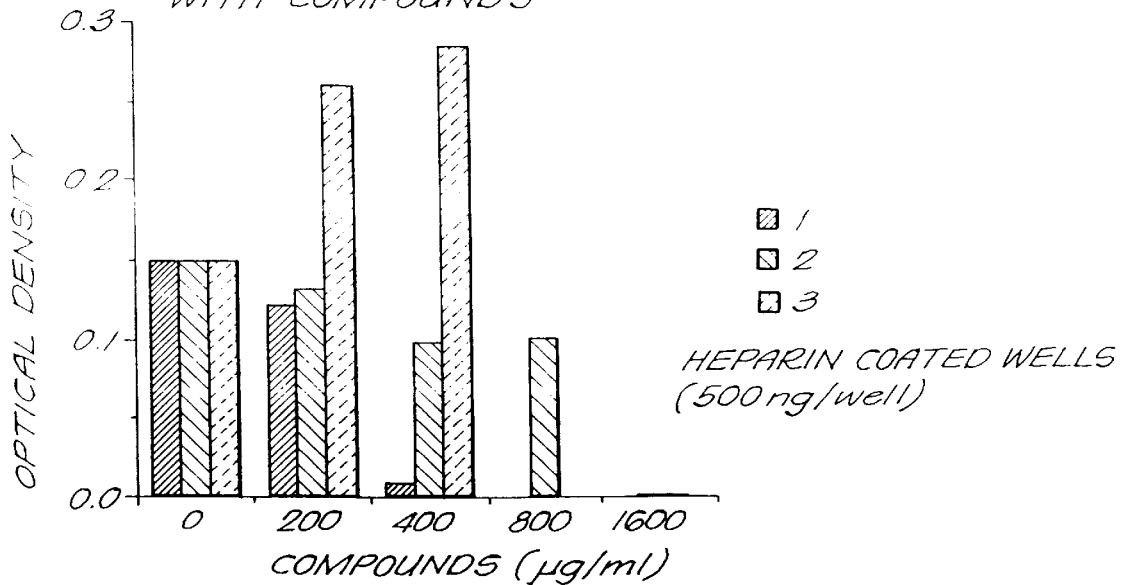

The features and other details of the invention will now be more particularly described with reference to the accompanying drawings and pointed out in the claims. It will be understood that particular embodiments described herein are shown by way of illustration and not as limitations of the invention. The principal features of this invention can be employed in various embodiments without departing from the scope of the invention. All parts and percentages are by weight unless otherwise specified.

The invention provides methods and compositions which are useful in the treatment of conditions related to glycosaminoglycan (GAG)-associated molecular interactions. In one embodiment, the invention provides a method for treating a condition related to a glycosaminoglycan-associated molecular interaction in a subject. The method includes administering to the subject, a therapeutically effective amount of a therapeutic compound having the formula:

$$Q\text{-}[\text{-}Y^-X^+]_n \quad (I)$$

wherein $Y^-$ is an anionic group at physiological pH; Q is a carrier molecule; $X^+$ is a cationic group; and n is an integer selected such that the biodistribution of the therapeutic compound for an intended target site is not prevented while maintaining activity of the therapeutic compound, or a pharmaceutically acceptable salt of ester thereof. The methods of the invention can be used therapeutically to treat a subject afflicted by a pathogen or can be used prophylactically in a subject susceptible to pathogens. The methods of the invention are based, at least in part, on inhibiting, eradicating, or preventing interaction between the cell membrane surface and the pathogen.

The language "treating a condition related to a glycosaminoglycan (GAG)-associated molecular interaction" and "treatment of a condition related to a glycosarninoglycan-associated molecular interaction" is intended to include changes in a condition related to a glycosaminoglycan-associated molecular interaction, as described infra, such that physiological symptoms in a subject can be significantly diminished or minimized. The language also includes control, prevention, relief, or inhibition of physiological symptoms or effects attributed to a disease state associated with glycosaminoglycan-associated molecular interactions. In one preferred embodiment, the control of the glycosaminoglycan-associated molecular interaction or condition related thereto is such that the glycosaminoglycan-associated molecular interaction or condition related thereto is eradicated. In another preferred embodiment, the control is selective such that a particular targeted glycosaminoglycan-associated molecular interaction, e.g., with a pathogen, is controlled while other cells and physiological flora which are not detrimental to the subject are allowed to remain substantially uncontrolled or substantially unaffected, e.g., lymphocytes, red blood cells, white blood cells, platelets, growth factors, etc.

The term "pathogen" is art recognized and is intended to include disease producing agents, such as organisms, e.g., microorganisms, capable of causing disease in a subject, e.g., a mammal, including, for example, bacteria, viruses, prions and fungi.

As used herein, "glycosaminoglycan (GAG)-associated molecular interaction" is intended to include the binding of a GAG to, for example, a cell surface, secreted, or extracellular protein. This term also includes any subsequent results of such protein binding such as, for example, delayed proteolytic degradation or denaturing, changes in protein conformation (which may, for example, lead to alterations of biological activity), or catalysis of a reaction between two different proteins bound to the same or different GAGs on the same or different proteoglycans. Also included is the ability of certain GAGs, e.g., heparin sulfate, to modulate the interaction of a protein to another GAG, for example, FGF-2 (basic fibroblast growth factor) to its GAG cell receptor.

Other GAG-associated molecular interactions include specific interactions between specific compounds and factors. Non-limiting examples include polypeptide growth factors (e.g., FGFs1-9, PDGF, HGF, VEGF, TGF-$\beta$, IL-3); extracellular matrix components (e.g., laminins, fibronectins; thrombospondins, tenascins, collagens, VonWillebrand's factor); proteases and anti-proteases (e.g., thrombin, TPA, UPA, clotting factors IX and X, PAI-1); cell-adhesion molecules (e.g., N-CAM, LI, myelin-associated glycoprotein); proteins involved in lipoprotein metabolism (e.g., APO-B, APO-E, lipoprotein lipase); cell-cell adhesion molecules (e.g., N-CAM, myelin-associated glycoprotein, selectins, pecam); angiogenin; lactoferrin; viral proteins (e.g., proteins from HIV, herpes complex) and other compounds which bind to GAG. The definition is intended to include the result of the binding of these factors to the GAG. For example, the binding of polypeptide growth factor to a GAG can result in cell proliferation, angiogenesis, inflammation, cancer, and other biologically important responses.

Also, the term "glycosaminoglycan (GAG)-associated molecular interaction" includes microbial "interactions" with GAGs which may, for example, lead to invasion of a host cell by a microorganism. It includes the binding of adhesius or other microbial proteins to GAG and the results thereafter. Some examples of such adhesius are: the filamentous hemagluggtinin of Bordetella pertussis, gP120 of HIV, gpB and pgC of HSV, etc. It also includes interactions where the GAG functions as a bridge between the microbial organism and the host cell, e.g., in chlamydia trachomatis, heparin sulfate binds to both C. trachomatis to host cell receptors catalyzing an interaction between the two. Also included in the definition is any interaction between a microbial organism and a cell which is mediated through the GAG.

The term "glycosaminoglycan (GAG)-associated molecular interaction" is further intended to include disease states or conditions caused by or associated with one or more pathogens which interact with extracellular membrane components, e.g., glycosaminoglycans, often found on host cell surfaces. In one embodiment, the disease state includes, for example, those diseases which afflict a subject by associating with or interfering with glycosaminoglycans found within the subject. In a preferred embodiment, the term "glycosaminoglycan-associated molecular interaction" does not include amyloidosis. In another preferred embodiment, the term "glycosaminoglycan-associated molecular interaction" does not include interactions between an amyloidogenic protein and a constituent of basement membrane to inhibit amyloid deposition. In yet another preferred embodiment, the term "glycosaminoglycan" does not include a constituent of basement membrane, e.g., heparan sulfate proteoglycan. In yet another preferred embodiment, the term "glycosaminoglycan" does not include sulfated GAGs, e.g., heparan sulfate. Presently unknown conditions related to glycosaminoglycan-associated molecular interactions that may be discovered in the future are encompassed, since their characterization as conditions related to glycosaminoglycan-associated molecular interactions will be readily determinable by persons skilled in the art.

Conditions related to glycosaminoglycan-associated molecular interactions include, for example, certain bacteria such as *Streptococcus pyogenes*, associated with acute rheumatic fever and poststreptococcal glomerulonephritis, *Chlamydia trachomatis*, *Staphylococcus aureus* (cystic fibrosis), *Bordetella pertussis* (whooping cough) and *Mycoplasma pneumoniae*. For example, *Streptococcus pyogenes* surfaces bind fibronectin, laminin, fibrinogen, nonspecific immunoglobulins A and G, α2-macroglobulin, β2-microglobulin and albumin. Infection by *Chlamydia trachomatis* is facilitated by binding of a heparan sulfate-like GAG present on the surface of chlamydia, to a heparan sulfate receptor on the target cell.

Additionally, conditions related to glycosaminoglycan-associated molecular interactions include certain types of viri, such as Herpesviridae, which are believed to be associated with HSPG during the infectious process. These viri appear to interact with a cell's surface through GAGs found on the proteoglycans of the cell plasma membrane. These GAGs are similar to heparin. Cytomegalovirus (CMV), HIV and Herpes simplex (HSV-1 and HSV-2) are examples of which are believed to infect cells via cell surface GAGs.

In one aspect, the present invention pertains to methods for modulating a glycosaminoglycan-associated molecular interaction, e.g., between an infectious agent and a GAG, in a subject. The methods include administering to the subject a therapeutically effective amount of a therapeutic compound. The therapeutic compound has the formula:

$$Q\text{-}[\text{Y}^-\text{X}^+]_n \qquad (I)$$

wherein $Y^-$ is an anionic group at physiological pH; Q is a carrier molecule; $X^+$ is a cationic group; and n is an integer selected such that the biodistribution of the therapeutic compound for an intended target site is not prevented while maintaining activity of the therapeutic compound, or a pharmaceutically acceptable salt or ester thereof.

The term "infectious agent" is intended to include those pathogens which are associated with disease states caused by bacteria, viri or prions. The term is also intended to include those extracellular components, e.g., proteins, etc., which are secreted, produced, or otherwise discharged by a pathogen, thereby causing the subject to be afflicted with a disease state associated with the infectious agent. Those disease states associated with infectious agents include *Streptococcus pyogenes, Chlamydia trachomatis, Staphylococcus aureus, Bordetella pertussis, Mycoplasma pneumoniae,* Herpesviridae, e.g., herpes simplex. The term infectious agent is also intended to encompass presently unknown infectious agents that may be discovered in the future, since their characterization as a infectious agents will be readily determinable by persons skilled in the art.

In an embodiment, therapeutic compounds which comprise at least one sulfate group covalently attached to a carrier molecule, or pharmaceutically acceptable salt thereof are used to treat a condition related to a glycosaminoglycan (GAG)-associated molecular interaction or an infectious agent. In particular, the therapeutic compounds of the invention comprise at least one sulfate group or a functional equivalent thereof, for example a sulfonic acid group or other functionally equivalent anionic group, linked to a carrier molecule. In addition to functioning as a carrier for the anionic functionality, the carrier molecule can enable the compound to traverse biological membranes and to be biodistributed without excessive or premature metabolism. Moreover, when multiple anionic functionalities are present on a carrier molecule, the carrier molecule serves to space the anionic groups in a correct geometric separation.

In one embodiment, when the condition related to a glycosaminoglycan-associated molecular interaction is associated with or caused by the bacteria *Chlamydia trachomatis*, the therapeutic compound is not sulfated polysaccharides kapp and lambda, iota carrageenans C-1263, C-3889 and C-4014, pentosan polysulfate (P-8275), fucodian (F-5631), dextran sulfate (D-6001), heparin (H-3393), heparan sulfate (H-7641) or dermatan sulfate (chondroitin sulfate A and B).

In another embodiment, when the condition related to a glycosaminoglycan-associated molecular interaction is associated with or caused by cytomegalovirus, the therapeutic compound is not pentosan polysulfate, dextran sulfate, heparin, copolymers of acrylic acid and vinylalcohol sulfate, α-cyclodextrin hexasulfate and αcyclodextrin dodecasulfate.

In yet another embodiment, when the condition related to a glycosaminoglycan-associated molecular interaction is associated with the virus Herpesviridae, the therapeutic agent is not chondroitin sulfate A, B or C.

In one embodiment, the method of the invention includes administering to the subject an effective amount of a therapeutic compound which has at least one anionic group covalently attached to a carrier molecule. The therapeutic compound is capable of treating a condition related to a glycosaminoglycan-associated molecular interaction or an infectious agent. The therapeutic compound can have the formula:

$$Q\text{-}[\text{-Y}^-\text{X}^+]_n \tag{I}$$

wherein $Y^-$ is an anionic group at physiological pH; Q is a carrier molecule; $X^+$ is a cationic group; and n is an integer. The number of anionic groups ("n") is selected such that the biodistribution of the compound for an intended target site is not prevented while maintaining activity of the compound. For example, the number of anionic groups is not so great as to inhibit traversal of an anatomical barrier, such as a cell membrane, or entry across a physiological barrier, such as the blood-brain barrier, in situations where such properties are desired. In one embodiment, n is an integer between 1 and 10. In another embodiment, n is an integer between 3 and 8.

An anionic group of a therapeutic compound of the invention is a negatively charged moiety that, when attached to a carrier molecule, can inhibit an interaction between a bacteria, a virus or an infectious agent and a cell membrane. The anionic group is desirably negatively charged at physiological pH. Preferably, the anionic therapeutic compound mimics the structure of a sulfated proteoglycan, i.e., is a sulfated compound or a functional equivalent thereof. "Functional equivalents" of sulfates are intended to include compounds such as sulfamates as well as bioisosteres. Bioisosteres encompass both classical bioisosteric equivalents and non-classical bioisosteric equivalents. Classical and non-classical bioisosteres of sulfate groups are known in the art (see, e.g., Silverman, R. B. *The Organic Chemistry of Drug Design and Drug Action*, Academic Press, Inc. San Diego, Calif., 1992, pp. 19–23). Accordingly, a therapeutic compound of the invention can comprise at least one anionic group including sulfonates, sulfates, sulfamates, phosphonates, phosphates, carboxylates, and heterocyclic groups of the following formulae:

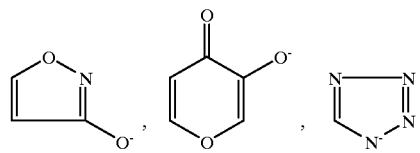

Depending on the carrier molecule, more than one anionic group can be attached thereto. When more than one anionic group is attached to a carrier molecule, the multiple anionic groups can be the same structural group (e.g., all sulfonates) or, alternatively, a combination of different anionic groups can be used (e.g., sulfonates and sulfates, etc.).

A therapeutic compound of the invention typically further comprises a counter cation (i.e., $X^+$ in formula (I): Q-[-Y$^-$X$^+$]$_n$). Cationic groups include positively charged atoms and moieties. If the cationic group is hydrogen, $H^+$, then the compound is considered an acid, e.g., ethanesulfonic acid. If hydrogen is replaced by a metal or its equivalent, the compound is a salt of the acid. Pharmaceutically acceptable salts of the therapeutic compound are within the scope of the invention. For example, $X^+$ can be a pharmaceutically acceptable alkali metal, alkaline earth, higher valency cation (e.g., aluminum salt), polycationic counter ion or ammonium. A preferred pharmaceutically acceptable salt is a sodium salt but other salts are also contemplated within their pharmaceutically acceptable range.

Within the therapeutic compound, the anionic group(s) is covalently attached to a carrier molecule. Suitable carrier molecules include carbohydrates, polymers, peptides, peptide derivatives, aliphatic groups, alicyclic groups, heterocyclic groups, aromatic groups or combinations thereof. A carrier molecule can be substituted, e.g. with one or more amino, nitro, halogen, thiol or hydroxy groups.

As used herein, the term "carbohydrate" is intended to include substituted and unsubstituted mono-, oligo-, and polysaccharides. Monosaccharides are simple sugars usually of the formula $C_6H_{12}O_6$ that can be combined to form oligosaccharides or polysaccharides. Monosaccharides include enantiomers and both the D and L stereoisomers of monosaccharides. Carbohydrates can have multiple anionic groups attached to each monosaccharide moiety. For example, in sucrose octasulfate, four sulfate groups are attached to each of the two monosaccharide moieties.

As used herein, the term "polymer" is intended to include molecules formed by the chemical union of two or more combining subunits called monomers. Monomers are molecules or compounds which usually contain carbon and are of relatively low molecular weight and simple structure. A monomer can be converted to a polymer by combination with itself or other similar molecules or compounds. A polymer may be composed of a single identical repeating subunit or multiple different repeating subunits (copolymers). Polymers within the scope of this invention include substituted and unsubstituted vinyl, acryl, styrene and carbohydrate-derived polymers and copolymers and salts thereof. In one embodiment, the polymer has a molecular weight of approximately 800–1000 Daltons. Examples of polymers with suitable covalently attached anionic groups (e.g., sulfonates or sulfates) include poly(2-acrylamido-2-methyl-1-propanesulfonic acid); poly(2-acrylamido-2-methyl-1-propanesulfonic acid-co-acrylonitrile); poly(2-acrylamido-2-methyl-1-propanesulfonic acid-co-styrene); poly(vinylsulfonic acid); poly(sodium 4-styrenesulfonic acid); and sulfates and sulfonates derived from: poly(acrylic acid); poly(methyl acrylate); poly(methyl methacrylate); and poly(vinyl alcohol); and pharmaceutically acceptable salts thereof. Examples of carbohydrate-derived polymers with suitable covalently attached anionic groups include those of the formula:

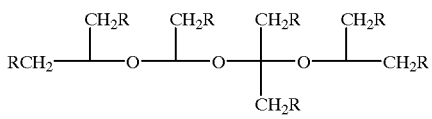

wherein R is $SO_3^-$ or $OSO_3^-$; and pharmaceutically acceptable salts thereof.

Peptides and peptide derivatives can also act as carrier molecules. The term "peptide" includes two or more amino acids covalently attached through a peptide bond. Amino acids which can be used in peptide carrier molecules include those naturally occurring amino acids found in proteins such as glycine, alanine, valine, cysteine, leucine, isoleucine, serine, threonine, methionine, glutamic acid, aspartic acid, glutamnine, asparagine, lysine, arginine, proline, histidine, phenylalanine, tyrosine, and tryptophan. The term amino acid further includes analogs, derivatives and congeners of naturally occurring amino acids, one or more of which can be present in a peptide derivative. For example, amino acid analogs can have lengthened or shortened side chains or variant side chains with appropriate functional groups. Also included are the D and L stereoisomers of an amino acid when the structure of the amino acid admits of stereoisomeric forms. The term "peptide derivative" further includes compounds which contain molecules which mimic a peptide backbone but are not amino acids (so-called peptidomimetics), such as benzodiazepine molecules (see e.g. James, G. L. et al. (1993) *Science* 260:1937–1942). The anionic groups can be attached to a peptide or peptide derivative through a functional group on the side chain of certain amino acids or other suitable functional group. For example, a sulfate or sulfonate group can be attached through the hydroxy side chain of a serine residue. Accordingly, in one embodiment, the peptide comprises four amino acids and anionic groups (e.g., sulfonates) are attached to the first, second and fourth amino acid. For example, the peptide can be Ser-Ser-Y-Ser, wherein an anionic group is attached to the side chain of each serine residue and Y is any amino acid. In addition to peptides and peptide derivatives, single amino acids can be used as carriers in the therapeutic compounds of the invention. For example, cysteic acid, the sulfonate derivative of cysteine, can be used.

The term "aliphatic group" is intended to include organic compounds characterized by straight or branched chains, typically having between 1 and 22 carbon atoms. Aliphatic groups include alkyl groups, alkenyl groups and alkynyl groups. In complex structures, the chains can be branched or cross-linked. Alkyl groups include saturated hydrocarbons having one or more carbon atoms, including straight-chain alkyl groups and branched-chain alkyl groups. Such hydrocarbon moieties may be substituted on one or more carbons with, for example, a halogen, a hydroxyl, a thiol, an amino, an alkoxy, an alkylcarboxy, an alkylthio, or a nitro group. Unless the number of carbons is otherwise specified, "lower aliphatic" as used herein means an aliphatic group, as defined above (e.g., lower alkyl, lower alkenyl, lower alkynyl), but having from one to six carbon atoms. Representative of such lower aliphatic groups, e.g., lower alkyl groups, are methyl, ethyl, n-propyl, isopropyl, 2-chloropropyl, n-butyl, sec-butyl, 2-aminobutyl, isobutyl, tert-butyl, 3-thiopentyl, and the like. As used herein, the term "amino" means -$NH_2$; the term "nitro" means —$NO_2$; the term "halogen" designates —F, —Cl, —Br or —I; the term "thiol" means SH; and the term "hydroxyl" means —OH. Thus, the term "alkylamino" as used herein means an alkyl group, as defined above, having an amino group attached thereto. The term "alkylthio" refers to an alkyl group, as defined above, having a sulfhydryl group is attached thereto. The term "alkylcarboxyl" as used herein means an alkyl group, as defined above, having a carboxyl group attached thereto. The term "alkoxy" as used herein means an alkyl group, as defined above, having an oxygen atom, attached thereto. Representative alkoxy groups include methoxy, ethoxy, propoxy, tert-butoxy and the like. The terms "alkenyl" and "alkynyl" refer to unsaturated aliphatic groups analogous to alkyls, but which contain at least one double or triple bond respectively.

The term "alicyclic group" is intended to include closed ring structures of three or more carbon atoms. Alicyclic groups include cycloparaffins or naphthenes which are saturated cyclic hydrocarbons, cycloolefins which are unsaturated with two or more double bonds, and cycloacetylenes which have a triple bond. They do not include aromatic groups. Examples of cycloparaffins include cyclopropane, cyclohexane, and cyclopentane. Examples of cycloolefins include cyclopentadiene and cyclooctatetraene. Alicyclic groups also include fused ring structures and substituted alicyclic groups such as alkyl substituted alicyclic groups. In the instance of the alicyclics such substituents can further comprise a lower alkyl, a lower alkenyl, a lower alkoxy, a lower alkylthio, a lower alkylamino, a lower alkylcarboxyl, a nitro, a hydroxyl, —$CF_3$, —CN, or the like.

The term "heterocyclic group" is intended to include closed ring structures in which one or more of the atoms in the ring is an element other than carbon, for example, nitrogen, or oxygen. Heterocyclic groups can be saturated or unsaturated and heterocyclic groups such as pyrrole and furan can have aromatic character. They include fused ring structures such as quinoline and isoquinoline. Other examples of heterocyclic groups include pyridine and purine. Heterocyclic groups can also be substituted at one or more constituent atoms with, for example, a halogen, a lower alkyl, a lower alkenyl, a lower alkoxy, a lower alkylthio, a lower alkylamino, a lower alkylcarboxyl, a nitro, a hydroxyl, —$CF_3$, —CN, or the like.

The term "aromatic group" is intended to include unsaturated cyclic hydrocarbons containing one or more rings. Aromatic groups include 5- and 6-membered single-ring groups which may include from zero to four heteroatoms, for example, benzene, pyrrole, furan, thiophene, imidazole, oxazole, thiazole, triazole, pyrazole, pyridine, pyrazine, pyridazine and pyrimidine, and the like. The aromatic ring may be substituted at one or more ring positions with, for example, a halogen, a lower alkyl, a lower alkenyl, a lower alkoxy, a lower alkylthio, a lower alkylamino, a lower alkylcarboxyl, a nitro, a hydroxyl, —$CF_3$, —CN, or the like.

The therapeutic compound of the invention can be administered in a pharmaceutically acceptable carrier. As used herein "pharmaceutically acceptable carrier" includes any and all solvents, dispersion media, coatings, antibacterial and antifungal agents, isotonic and absorption delaying agents, and the like which are compatible with the activity of the compound and are physiologically acceptable to the subject. An example of a pharmaceutically acceptable carrier is buffered normal saline (0.15 molar NaCl). The use of such media and agents for pharmaceutically active substances is well known in the art. Except insofar as any conventional media or agent is incompatible with the therapeutic compound, use thereof in the compositions suitable for pharmaceutical administration is contemplated. Supplementary active compounds can also be incorporated into the compositions.

In an embodiment of the method of the invention, the therapeutic compound administered to the subject is comprised of at least one sulfonate group covalently attached to a carrier molecule, or a pharmaceutically acceptable salt thereof. Accordingly, the therapeutic compound can have the formula:

$$Q\text{-}[\text{-SO}_3^- X^+]_n \qquad (II)$$

wherein Q is a carrier molecule; $X^+$ is a cationic group; and n is an integer. Suitable carrier molecules and cationic groups are those described hereinbefore. The number of sulfonate groups ("n") is selected such that the biodistribution of the compound for an intended target site is not prevented while maintaining activity of the compound as discussed earlier. In one embodiment, n is an integer between 1 and 10. In another embodiment, n is an integer between 3 and 8. As described earlier, therapeutic compounds with multiple sulfonate groups can have the sulfonate groups spaced such that the compound interacts optimally with a receptor site on the cell membrane.

In certain embodiments, the carrier molecule for a sulfonate(s) is a lower aliphatic group (e.g., a lower alkyl, lower alkenyl or lower alkynyl), a heterocyclic group, a disaccharide, a polymer or a peptide or peptide derivative. Furthermore, the carrier can be substituted, e.g. with one or more amino, nitro, halogen, thiol or hydroxy groups. In certain embodiments, the carrier molecule for a sulfonate(s) is an aromatic group.

Particularly suitable therapeutic compounds include 1,3-propanedisulfonic acid, 3-amino-1-propanesulfonic acid, 3-dimethylamino-1-propanesulfonic acid sodium salt, 2-(3-sulfopropyl)-1,2,3,4-tetrahydro-9H-pyrido[3,4-b]indole, sodium salt, 3-[2-(6-methoxy-1,2,3,4-tetrahydroisoquinolinyl)]-1-propanesulfonic acid, 3-(2-hydroxyethyl)amino-1-propanesulfonic acid, 3-(3-hydroxy-1-propyl)amino-1-propanesulfonic acid, (−)3-[(R)-2-hydroxy-1-propyl]amino-1-propanesulfonic acid, 3-(4-hydroxy-1-butyl)amino-1-propanesulfonic acid, 3-(5-hydroxy-1-pentyl)amino-1-propanesulfonic acid, 3-(6-hydroxy-1-hexyl)amino-1-propanesulfonic acid, 3-(2-hydroxyethyl)amino-1-propanesulfonic acid, 3-(2-hydroxyethyl)amino-1-propanesulfonic acid, 3-(2-hydroxyethyl)amino-1-propanesulfonic acid, 3-(2-hydroxyethyl)amino-1-propanesulfonic acid, 3-hexylamino-1-propanesulfonic acid, 3-undecylamino-1-propanesulfonic acid, and 3-octadecylamino-1-propanesulfonic acid, and pharmaceutically acceptable salts or esters thereof.

Examples of sulfonated polymeric therapeutic compounds include poly(2-5 acrylamido-2-methyl-1-propanesulfonic acid); poly(2-acrylamido-2-methyl4-1-propanesulfonic acid-co-acrylonitrile); poly(2-acrylamido-2-methyl-1-propanesulfonic acid-co-styrene); poly(vinylsulfonic acid); poly(sodium 4-styrenesulfonic acid); a sulfonic acid derivative of poly (acrylic acid); a sulfonic acid derivative of poly (methyl acrylate); a sulfonic acid derivative of poly (methyl methacrylate); and a sulfonate derivative of poly(vinyl alcohol); and pharmaceutically acceptable salts thereof.

A suitable sulfonated polymer is poly(vinylsulfonic acid) (PVS) or a pharmaceutically acceptable salt thereof, preferably the sodium salt thereof. In one embodiment, PVS having a molecular weight of about 800–1000 Daltons is used. PVS may be used as a mixture of stereoisomers or as a single active isomer.

A suitable sulfonated disaccharide is a fully or partially sulfonated sucrose, or pharmaceutically acceptable salt thereof, such as sucrose octasulfonate. Other sulfonated saccharides include 5-deoxy-1,2-O-isopropylidene-α-D-xylofuranose-5-sulfonic acid (XXIII, shown as the sodium salt).

Suitable lower aliphatic sulfonated compounds for use in the invention include ethanesulfonic acid; 2-aminoethanesulfonic acid (taurine); cysteic acid (3-sulfoalanine or α-amino-β-sulfopropionic acid); 1-propanesulfontic acid; 1,2-ethanedisulfonic acid; 1,4-butanedisulfonic acid; 1,5-pentanedisulfonic acid; and 4-hydroxybutane-1-sulfonic acid (VIII, shown as the sodium salt); and pharmaceutically acceptable salts thereof. Other aliphatic sulfonated compounds contemplated for use in the invention include 1-butanesulfonic acid (XLVII, shown as the sodium salt), 2-propanesulfonic acid (XLIX, shown as the sodium salt), 3-pentanesulfonic acid (L, shown as the sodium salt), 4-heptanesulfonic acid (LII, shown as the sodium salt), 1-decanesulfonic acid (XLVIII, shown as the sodium salt); and pharmaceutically acceptable salts thereof. Sulfonated substituted aliphatic compounds contemplated for use in the invention include 3-amino-1-propanesulfonic acid (XXII, shown as the sodium salt), 3-hydroxypropanesulfonic acid sulfate (XXXV, shown as the disodium salt), 1,7-dihydroxy-4-heptanesulfonic acid (LIII, shown as the sodium salt); and pharmaceutically acceptable salts thereof. Yet other sulfonated compounds contemplated for use in the invention include 2-[(4-pyridinyl)amido]ethanesulfonic acid (LIV, depicted as the sodium salt), and pharmaceutically acceptable salts thereof.

Suitable heterocyclic sulfonated compounds include 3-(N-morpholino)propanesulfonic acid; and tetrahydrothiophene-1,1-dioxide-3,4-disulfonic acid; and pharmaceutically acceptable salts thereof.

Aromatic sulfonated compounds include 1,3-benzenedisulfonic acid (XXXVI, shown as the disodium salt), 2,5-dimethoxy-1,4-benzenedisulfonic acid (depicted as the disodium salt, XXXVII, or the dipotassium salt, XXXIX), 4-amino-3-hydroxy-1-naphthalenesulfonic acid (XLIII), 3,4-diamino-1-naphthalenesulfonic acid (XLIV); and pharmaceutically acceptable salts thereof.

In another embodiment of the method of the invention, the therapeutic compound administered to the subject is comprised of at least one sulfate group covalently attached to a carrier molecule, or a pharmaceutically acceptable salt thereof. Accordingly, the therapeutic compound can have the formula:

$$Q\text{-}[\text{-SO}_3^- X^+]_n \qquad (III)$$

wherein Q is a carrier molecule; $X^+$ is a cationic group; and n is an integer. Suitable carrier molecules and cationic groups are those described hereinbefore. The number of sulfate groups ("n") is selected such that the biodistribution of the compound for an intended target site is not prevented while maintaining activity of the compound as discussed earlier. In one embodiment, n is an integer between 1 and 10. In another embodiment, n is an integer between 3 and 8. As described earlier, therapeutic compounds with multiple sulfate groups can have the sulfate groups spaced such that the compound interacts optimally with a bacteria, virus or an infectious agent or a cell membrane.

In certain embodiments, the carrier molecule for a sulfate (s) is a lower aliphatic group (e.g., a lower alkyl, lower alkenyl or lower alkynyl), an aromatic group, a disaccharide, a polymer or a peptide or peptide derivative. Furthermore, the carrier can be substituted, e.g. with one or more amino, nitro, halogen, thiol or hydroxy groups.

Examples of sulfated polymeric therapeutic compounds include poly(2-acrylamido-2-methyl-propyl sulfuric acid); poly(2-acrylamido-2-methyl-propyl sulfuric acid-co-acrylonitrile); poly(2-acrylamido-2-methyl-propyl sulfuric acid-co-styrene); poly(vinylsulfuric acid); poly(sodium 4-styrenesulfate); a sulfate derivative of poly(acrylic acid); a sulfate derivative of poly(methyl acrylate); a sulfate derivative of poly(methyl methacrylate); and a sulfate derivative of poly(vinyl alcohol); and pharmaceutically acceptable salts thereof.

A suitable sulfated polymer is poly(vinylsulfuric acid) or pharmaceutically acceptable salt thereof. A suitable sulfated disaccharide is sucrose octasulfate or pharmaceutically acceptable salt thereof. Other contemplated sulfated saccharides include the acid form of methyl-α-D-glucopyranoside 2,3-disulfate (XVI), methyl 4,6-O-benzylidene-α-D-glucopyranoside 2,3-disulfate (XVII), 2,3,4,3',4'-sucrose pentasulfate (XXXIII), 1,3:4,6-di-O-benzylidene-D-mannitol 2,5-disulfate (XLI), D-mannitol 2,5-disulfate (XLII), 2,5-di-O-benzyl-D-mannitol tetrasulfate (XLV); and pharmaceutically acceptable salts thereof.

Suitable lower aliphatic sulfated compounds for use in the invention include ethyl sulfuric acid; 2-aminoethan-1-ol sulfuric acid; 1-propanol sulfuric acid; 1,2-ethanediol disulfuric acid; 1,3-propanediol disulfuric acid; 1,4-butanediol disulfuric acid; 1,5-pentanediol disulfuric acid; and 1,4-butanediol monosulfuric acid; and pharmaceutically acceptable salts thereof. Other sulfated aliphatic compounds contemplated for use in the invention include the acid form of 1,3-cyclohexanediol disulfate (XL), 1,3,5-heptanetriol trisulfate (XIX), 2-hydroxymethyl-1,3-propanediol trisulfate (XX), 2-hydroxymethyl-2-methyl-1,3-propanediol trisulfate (XXI), 1,3,5,7-heptanetriol tetrasulfate (XLVI), 1,3,5,7,9-nonane pentasulfate (LI); and pharmaceutically acceptable salts thereof. Other sulfated compounds contemplated for use in the invention include the acid form of 2-amino-2-hydroxymethyl-1,3-propanediol trisulfate (XXIV), 2-benzyloxy-1,3-propanediol disulfate (XXIX), 3-hydroxypropylsulfamic acid sulfate (XXX)2,2'-iminoethanol disulfate (XXXI), N,N-bis(2-hydroxyethyl) sulfamic acid disulfate (XXXII); and pharmaceutically acceptable salts thereof.

Suitable heterocyclic sulfated compounds include 3-(N-morpholino) propanesulfuric acid; and tetrahydrothiophene-1,1-dioxide-3,4-diol disulfuric acid; and pharmaceutically acceptable salts thereof.

A further aspect of the invention includes pharmaceutical compositions for treating conditions related to glycosaminoglycan-associated molecular interactions, such as those described supra. The therapeutic compounds in the methods of the invention, as described hereinbefore, can be incorporated into a pharmaceutical composition in an amount effective to treat a condition related to a glycosaminoglycan-associated molecular interaction in a pharmaceutically acceptable carrier.

In another embodiment, the pharmaceutical compositions of the invention include a therapeutic compound that has at least one sulfate group covalently attached to a carrier molecule, or a pharmaceutically acceptable salt thereof, in an amount sufficient to treat a condition related to a glycosaminoglycan-associated molecular interaction, and a pharmaceutically acceptable carrier. The therapeutic compound can have the following formula:

$$Q\text{-}[\text{-}OSO_3^-X^+]_n \qquad (III)$$

wherein Q is a carrier molecule; $X^+$ is a cationic group; and n is an integer selected such that the biodistribution of the compound for an intended target site is not prevented while maintaining activity of the compound.

The use of prodrugs which are converted in vivo to the therapeutic compounds of the invention (see, e.g., R. B. Silverman, 1992, "The Organic Chemistry of Drug Design and Drug Action", Academic Press, Chp. 8) are also to be considered within the scope of the present invention. Such prodrugs can be used to alter the biodistribution (e.g., to allow compounds which would not typically cross the blood-brain barrier to cross the blood-brain barrier) or the pharmacokinetics of the therapeutic compound. For example, an anionic group, e.g., a sulfate or sulfonate, can be esterified, e.g., with a methyl group or a phenyl group, to yield a sulfate or sulfonate ester. When the sulfate or sulfonate ester is administered to a subject, the ester is cleaved, enzymatically or non-enzymatically, reductively or hydrolytically, to reveal the anionic group. Such an ester can be cyclic, e.g., a cyclic sulfate or sultone, or two or more anionic moieties may be esterified through a linking group. Exemplary cyclic compounds include, for example, 2-sulfobenzoic acid (LV), propane sultone (LVI), butane sultone (LVII), 1,3-butanediol cyclic sulfate (LVIII), α-chloro-α-hydroxy-o-toluenesulfonic acid sultone (LIX), and 6-nitronaphth-[1,8-cd]-1,2,-oxathiole 2,2-dioxide (LX). In an embodiment, the prodrug is a cyclic sulfate or sultone. An anionic group can be esterified with moieties (e.g., acyloxymethyl esters) which are cleaved to reveal an intermediate compound which subsequently decomposes to yield the active compound. In another embodiment, the prodrug is a reduced form of a sulfate or sulfonate, e.g., a thiol, which is oxidized in vivo to the therapeutic compound. Furthermore, an anionic moiety can be esterified to a group which is actively transported in vivo, or which is selectively taken up by target organs. The ester can be selected to allow specific targeting of the therapeutic moieties to particular organs, as described below for carrier moieties.

Carrier molecules useful in the therapeutic compounds include carrier molecules previously described, e.g. carbohydrates, polymers, peptides, peptide derivatives, aliphatic groups, alicyclic groups, heterocyclic groups, aromatic groups or combinations thereof. Suitable polymers include substituted and unsubstituted vinyl, acryl, styrene and carbohydrate-derived polymers and copolymers and salts thereof. Suitable carrier molecules include a lower alkyl group, a heterocyclic group, a disaccharide, a polymer or a peptide or peptide derivative.

Carrier molecules useful in the present invention may also include moieties which allow the therapeutic compound to be selectively delivered to a target organ or organs. For example, if delivery of a therapeutic compound to the brain is desired, the carrier molecule may include a moiety capable of targeting the therapeutic compound to the brain, by either active or passive transport (a "targeting moiety"). Illustratively, the carrier molecule may include a redox moiety, as described in, for example, U.S. Pat. Nos. 4,540,564 and 5,389,623, both to Bodor. These patents disclose drugs linked to dihydropyridine moieties which can enter the brain, where they are oxidized to a charged pyridinium species which is trapped in the brain. Thus, drug accumulates in the brain. Exemplary pyridine/dihydropyridine compounds of the invention include sodium 1-(3-sulfopropyl)-1,4-dihydropyridine (LXI), sodium 2-(nicotinylamido)-ethanesulfonate (LXII), and 1-(3-sulfopropyl)-pyridinium betaine (LXIII). Other carrier moieties include compounds, such as amino acids or thyroxine, which can be passively or actively transported in vivo. An illustrative compound is phenylalanyltaurine (LXIX), in which a taurine molecule is conjugated to a phenylalanine (a large neutral amino acid). Such a carrier moiety can be metabolically removed in vivo, or can remain intact as part of an active compound. Structural mimics of amino acids (and other actively transported moieties) are also useful in the invention (e.g., 1-(aminomethyl)-1-(sulfomethyl)-cyclohexane (LXX)). Other exemplary amino acid mimetics include p-(sulfomethyl)phenylalanine (LXXII), p-(1,3-disulfoprop-2-yl)phenylalanine (LXXIII), and O-(1,3-disulfoprop-2-yl) tyrosine (LXXIV). Exemplary thyroxine mimetics include compounds LXXV, LXVI, and LXXVII. Many targeting moieties are known, and include, for example, asialoglycoproteins (see, e.g. Wu, U.S. Pat. No. 5,166,320) and other ligands which are transported into cells via receptor-mediated endocytosis (see below for further examples of targeting moieties which may be covalently or non-covalently bound to a carrier molecule). Furthermore, the therapeutic compounds of the invention may bind to bacteria, viri, infectious agents or cell membranes in the circulation and thus be transported to the site of action.

The targeting and prodrug strategies described above can be combined to produce a compound that can be transported as a prodrug to a desired site of action and then unmasked to reveal an active compound. For example, the dihydropyrine strategy of Bodor (see supra) can be combined with a cyclic prodrug, as for example in the compound 2-(1-methyl-1,4-dihydronicotinyl)amidomethyl-propanesultone (LXXI).

In one embodiment, the therapeutic compound in the pharmaceutical compositions is a sulfonated polymer, for example poly(2-acrylamido-2-methyl-1-propanesulfonic acid); poly(2-acrylamido-2-methyl-1-propanesulfonic acid-co-acrylonitrile); poly(2-acrylamido-2-methyl-1-propanesulfonic acid-co-styrene); poly(vinylsulfonic acid); poly(sodium 4-styrenesulfonic acid); a sulfonate derivative of poly (acrylic acid); a sulfonate derivative of poly (methyl acrylate); a sulfonate derivative of poly(methyl methacrylate); and a sulfonate derivative of poly(vinyl alcohol); and pharmaceutically acceptable salts thereof.

The therapeutic compound can also have the structure:

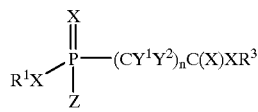

(IV)

in which Z is $XR^2$ or $R^4$, $R^1$ and $R^2$ are each independently hydrogen, a substituted or unsubstituted aliphatic group (preferably a branched or straight-chain aliphatic moiety having from 1 to 24 carbon atoms in the chain; or an unsubstituted or substituted cyclic aliphatic moiety having from 4 to 7 carbon atoms in the aliphatic ring; suitable aliphatic and cyclic aliphatic groups are alkyl groups, more preferably lower alkyl), an aryl group, a heterocyclic group, or a salt-forming cation; $R^3$ is hydrogen, lower alkyl, aryl, or a salt-forming cation; X is, independently for each occurrence, O or S; $R^4$ is hydrogen, lower alkyl, aryl or amino; $Y^1$ and $Y^2$ are each independently hydrogen, halogen (e.g., F, Cl, Br, or I), lower alkyl, amino (including alkylamino, dialkylamino, arylamino, diarylamino, and alkylarylamino), hydroxy, alkoxy, or aryloxy; and n is an integer from 0 to 12 (more preferably 0 to 6, more preferably 0 or 1). These compounds are described in U.S. application Ser. No. 08/912,574, the contents of which are incorporated herein by reference.

Suitable therapeutic compounds for use in the invention include compounds in which both $R^1$ and $R^2$ are pharmaceutically acceptable salt-forming cations. It will be appreciated that the stoichiometry of an anionic compound to a salt-forming counterion (if any) will vary depending on the charge of the anionic portion of the compound (if any) and the charge of the counterion. In a particularly suitable embodiment, $R^1$, $R^2$ and $R^3$ are each independently a sodium, potassium or calcium cation. In certain embodiments in which at least one of $R^1$ and $R^2$ is an aliphatic group, the aliphatic group has between 1 and 10 carbons atoms in the straight or branched chain, and is more preferably a lower alkyl group. In other embodiments in which at least one of $R^1$ and $R^2$ is an aliphatic group, the aliphatic group has between 10 and 24 carbons atoms in the straight or branched chain. In certain embodiments, n is 0 or 1; more preferably, n is 0. In certain embodiments of the therapeutic compounds, $Y^1$ and $Y^2$ are each hydrogen.

In certain embodiments, the therapeutic compound of the invention can have the structure:

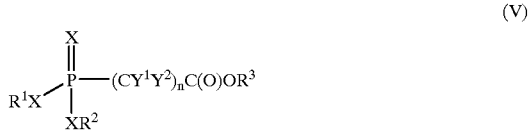

(V)

in which $R^1$, $R^2$, $R^3$, $Y^1$, $Y^2$, X and n are as defined above. In other embodiments, the therapeutic compound of the invention can have the structure:

(VI)

in which $R^1$, $R^2$, $R^3$, $Y^1$, $Y^2$, and X are as defined above, $R_a$ and $R_b$ are each independently hydrogen, alkyl, aryl, or heterocyclyl, or $R_a$ and $R_b$, taken together with the nitrogen atom to which they are attached, form a cyclic moiety having from 3 to 8 atoms in the ring, and n is an integer from 0 to 6. In certain embodiments, $R_a$ and $R_b$ are each hydrogen. In certain embodiments, a compound of the invention comprises an α-amino acid (or α-amino acid ester), more preferably a L-α-amino acid or ester.

The Z, Q, $R^1$, $R^2$, $R^3$, $Y^1$, $Y^2$ and X groups are each independently selected such that the biodistribution of the therapeutic compound for an intended target site is not prevented while maintaining activity of the therapeutic compound. For example, the number of anionic groups (and the overall charge on the therapeutic compound) should not be so great as to inhibit traversal of an anatomical barrier, such as a cell membrane, or entry across a physiological barrier, such as the blood-brain barrier, in situations where such properties are desired. For example, it has been reported that esters of phosphonoformate have biodistribution properties different from, and in some cases superior to, the biodistribution properties of phosphonoformate (see, e.g., U.S. Pat. Nos. 4,386,081 and 4,591583 to Helgstrand et al., and U.S. Pat. Nos. 5,194,654 and 5,463,092 to Hostetler et al.). Thus, in certain embodiments, at least one of $R^1$ and $R^2$ is an aliphatic group (more preferably an alkyl group), in which the aliphatic group has between 10 and 24 carbons atoms in the straight or branched chain. The number, length, and degree of branching of the aliphatic chains can be selected to provide a desired characteristic, e.g., lipophilicity. In other embodiments, at least one of $R^1$ and $R^2$ is an aliphatic group (more preferably an alkyl group), in which the aliphatic group has between 1 and 10 carbons atoms in the straight or branched chain. Again, the number, length, and degree of branching of the aliphatic chains can be selected to provide a desired characteristic, e.g., lipophilicity or ease of ester cleavage by enzymes. In certain embodiments, a suitable aliphatic group is an ethyl group.

In another embodiment, the therapeutic compound of the invention can have the structure:

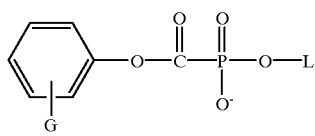

(VII)

in which G represents hydrogen or one or more substituents on the aryl ring (e.g., alkyl, aryl, halogen, amino, and the like) and L is a substituted alkyl group (in certain embodiments, preferably a lower alkyl), more preferably a hydroxy-substituted alkyl or an alkyl substituted with a nucleoside base. In certain embodiments, G is hydrogen or an electron-donating group. In embodiments in which G is an electron-withdrawing group, G is preferably an electron withdrawing group at the meta position. The term "electron-withdrawing group" is known in the art, and, as used herein, refers to a group which has a greater electron-withdrawing than hydrogen. A variety of electron-withdrawing groups are known, and include halogens (e.g., fluoro, chloro, bromo, and iodo groups), nitro, cyano, and the like. Similarly, the term "electron-donating group", as used herein, refers to a group which is less electron-withdrawing than hydrogen. In embodiments in which G is an electron donating group, G can be in the ortho, meta or para position.

In certain embodiments, L is a moiety selected from the group consisting of:

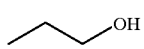

IVa

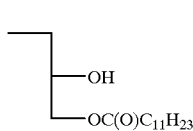

IVb

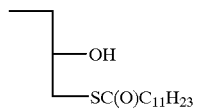

IVc

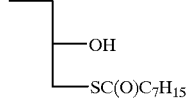

IVd

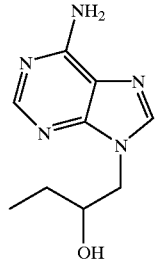

IVe

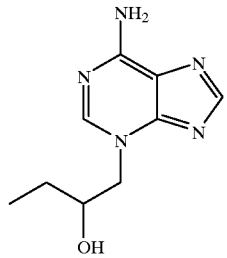

IVf

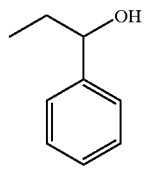

IVg

Table 1 lists data pertinent to the characterization of these compounds using art-recognized techniques.

TABLE 1

| COMPOUND | $^{31}$P NMR | $^{13}$C NMR | FAB-MS(−) |
|---|---|---|---|
| IVa | −6.33 (DMSO-$d_6$) | 60.97 CH$_2$OH (d, J = 6 Hz)<br>66.76 CHOH (d, J = 7.8 Hz)<br>121.65, 121.78, 121.99, 125.71,<br>129.48, 129.57, 126.43<br>Aromatic CH<br>134.38 Aniline C—N<br>150.39 Phenyl C—O (d, J = 7 Hz)<br>171.57 P—C═O (d, J = 234 Hz) | 245.2 |
| IVb | −6.41 (DMSO-$d_6$) | 13.94 CH$_3$<br>22.11, 24.40, 28.56, 28.72, 28.99,<br>29.00, 31.30, 33.43, —(CH$_2$)$_{10}$—<br>65.03 CH$_2$—OC(O)<br>66.60 CH$_2$—OP (d, J = 5.6 Hz)<br>67.71 CH$_2$—OH (d, J = 6 Hz)<br>121.73, 121.10, 125.64, 126.57,<br>129.40, 129.95, Aromatic CH<br>134.04 Aniline C—N<br>150.31 Phenyl C—O<br>171.44 P—C═O (d, J = 6.7 Hz)<br>172.83 O—C═O | 456 |
| IVc | −6.46 | 13.94 CH$_3$ | 471 |

TABLE 1-continued

| COMPOUND | $^{31}$P NMR | $^{13}$C NMR | FAB-MS(−) |
|---|---|---|---|
| | (DMSO-d$_6$) | 22.11, 25.10, 28.68, 28.72, 28.85, 29.00, 30.76, 31.31, 32.10, —(CH$_2$)$_{10}$— 43.36 CH$_2$—S 68.43 CH$_2$—OH 68.43 CH—OH (d, J = 6.3 Hz) 68.76 P—O—CH$_2$-9d, J = 5.8 Hz) 121.75, 122.03, 125.62, 126.37, 129.30, 129.53, Aromatic CH 134.23 Aniline C—N 150.37 Phenyl C—O (d, J = 6.7 Hz) 171.47 P—C=O (d, J = 234.0 Hz) 198.47 S—C=O | |
| IVd | −6.61 (DMSO-d$_6$) | 13.94 CH$_3$ 22.06, 25.14, 28.24, 28.35, 31.09, 32.14 —(CH$_2$)$_6$— 43.40 CH$_2$—S 68.50 P—O—CH$_2$- (d, J = 5.8 Hz) 68.77 CH—OH (d, 6.4 Hz) 121.78, 122.59, 125.69, 127.06, 129.43, 129.59 Aromatic CH 133.39 Aniline C—N 150.38 Phenyl C—O (d, J = 6.7 Hz) 171.47 P—C=O (d, J = 234.4 Hz) 198.54 S—C=O | 416 |
| IVe | −5.76 (D$_2$O) | N/A | N/A |
| IVf | −7.00 (DMSO-d$_6$) | N/A | N/A |
| IVg | −6.60 (DMSO-D6) | 70.84 CH$_2$—OH 72.17 CH—OH 121.68, 121.79, 121.85, 125.71 127.10, 127.92, 129.36, 129.50, 129.59 Aromatic CH 134.51 Aniline C—N 142.34 Aromatic C—CH 150.37 Phenyl C—O (d, J = 6.2 Hz) 171.59 P—C=O (d, J = 232.6 Hz) | 321 |

It will be noted that the structure of some of the therapeutic compounds of this invention includes asymmetric carbon atoms. It is to be understood accordingly that the isomers (e.g., enantiomers and diastereomers) arising from such asymmetry are included within the scope of this invention. Such isomers can be obtained in substantially pure form by classical separation techniques and by sterically controlled synthesis. For the purposes of this application, unless expressly noted to the contrary, a therapeutic compound shall be construed to include both the R or S stereoisomers at each chiral center. In certain embodiments, an therapeutic compound of the invention comprises a cation (i.e., in certain embodiments, at least one of $R^1$, $R^2$ or $R^3$ is a cation). If the cationic group is hydrogen, H$^+$, then the therapeutic compound is considered an acid, e.g., phosphonoformic acid. If hydrogen is replaced by a metal ion or its equivalent, the therapeutic compound is a salt of the acid. Pharmaceutically acceptable salts of the therapeutic compound are within the scope of the invention. For example, at least one of $R^1$, $R^2$ or $R^3$ can be a pharmaceutically acceptable alkali metal (e.g., Li, Na, or K), ammonium cation, alkaline earth cation (e.g., Ca$^{2+}$, Ba$^{2+}$, Mg$^{2+}$), higher valency cation, or polycationic counter ion (e.g., a polyammonium cation). (See, e.g., Berge et al. (1977) "Pharmaceutical Salts", *J. Pharm. Sci.* 66:1–19). It will be appreciated that the stoichiometry of an anionic compound to a salt-forming counterion (if any) will vary depending on the charge of the anionic portion of the compound (if any) and the charge of the counterion. Preferred pharmaceutically acceptable salts include a sodium, potassium or calcium salt, but other salts are also contemplated within their pharmaceutically acceptable range.

The term "pharmaceutically acceptable esters" refers to the relatively non-toxic, esterified products of the therapeutic compounds of the present invention. These esters can be prepared in situ during the final isolation and purification of the therapeutic compounds or by separately reacting the purified therapeutic compound in its free acid form or hydroxyl with a suitable esterifying agent; either of which are methods known to those skilled in the art. Carboxylic acids and phosphonic acids can be converted into esters according to methods well known to one of ordinary skill in the art, e.g., via treatment with an alcohol in the presence of a catalyst. A preferred ester group (e.g., when $R^3$ is lower alkyl) is an ethyl ester group.

The term "alkyl" refers to the saturated aliphatic groups, including straight-chain alkyl groups, branched-chain alkyl groups, cycloalkyl (alicyclic) groups, alkyl substituted cycloalkyl groups, and cycloalkyl substituted alkyl groups. In preferred embodiments, a straight chain or branched chain alkyl has 30 or fewer carbon atoms in its backbone (e.g., $C_1$–$C_{30}$ for straight chain, $C_3$–$C_{30}$ for branched chain), and more preferably 20 or fewer. Likewise, preferred cycloalkyls have from 4–10 carbon atoms in their ring structure, and more preferably have 4–7 carbon atoms in the ring structure. The term "lower alkyl" refers to alkyl groups having from 1 to 6 carbons in the chain, and to cycloalkyls having from 3 to 6 carbons in the ring structure.

Moreover, the term "alkyl" (including "lower alkyl") as used throughout the specification and claims is intended to include both "unsubstituted alkyls" and "substituted alkyls", the latter of which refers to alkyl moieties having substituents replacing a hydrogen on one or more carbons of the hydrocarbon backbone. Such substituents can include, for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfate, sulfonato, sulfamoyl, sulfonamido, nitro, trifluoromethyl, cyano, azido, heterocyclyl, aralkyl, or an aromatic or heteroaromatic moiety. It will be understood by those skilled in the art that the moieties substituted on the hydrocarbon chain can themselves be substituted, if appropriate. Cycloalkyls can be further substituted, e.g., with the substituents described above. An "aralkyl" moiety is an alkyl substituted with an aryl (e.g., phenylmethyl (benzyl)).

The term "alkoxy", as used herein, refers to a moiety having the structure -O-alkyl, in which the alkyl moiety is described above.

The term "aryl" as used herein includes 5- and 6-membered single-ring aromatic groups that may include from zero to four heteroatoms, for example, unsubstituted or substituted benzene, pyrrole, furan, thiophene, imidazole, oxazole, thiazole, triazole, pyrazole, pyridine, pyrazine, pyridazine and pyrimidine, and the like. Aryl groups also include polycyclic fused aromatic groups such as naphthyl, quinolyl, indolyl, and the like. The aromatic ring can be substituted at one or more ring positions with such substituents, e.g., as described above for alkyl groups. Preferred aryl groups include unsubstituted and substituted phenyl groups.

The term "aryloxy", as used herein, refers to a group having the structure -O-aryl, in which the aryl moiety is as defined above.

The term "amino," as used herein, refers to an unsubstituted or substituted moiety of the formula —NR$_a$R$_b$, in which R$_a$ and R$_b$ are each independently hydrogen, alkyl, aryl, or heterocyclyl, or R$_a$ and R$_b$, taken together with the nitrogen atom to which they are attached, form a cyclic moiety having from 3 to 8 atoms in the ring. Thus, the term "amino" is intended to include cyclic amino moieties such as piperidinyl or pyrrolidinyl groups, unless otherwise stated. An "amino-substituted amino group" refers to an amino group in which at least one of R$_a$ and R$_b$, is further substituted with an amino group.

In another embodiment, R$^1$ or R$^2$ can be (for at least one occurrence) a long-chain aliphatic moiety. The term "long-chain aliphatic moiety" as used herein, refers to a moiety having a straight or branched chain aliphatic moiety (e.g., an alkyl or alkenyl moiety) having from 10 to 24 carbons in the aliphatic chain, e.g., the long-chain aliphatic moiety is an aliphatic chain of a fatty acid (preferably a naturally-occurring fatty acid). Representative long-chain aliphatic moieties include the aliphatic chains of stearic acid, oleic acid, linolenic acid, and the like.

In certain embodiments, the therapeutic compound of the invention can have the structure:

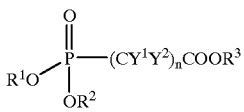

(VIII)

in which R$^1$ and R$^2$ are each independently hydrogen, an aliphatic group (preferably a branched or straight-chain aliphatic moiety having from 1 to 24 carbon atoms, more preferably 10–24 carbon atoms, in the chain; or an unsubstituted or substituted cyclic aliphatic moiety having from 4 to 7 carbon atoms in the aliphatic ring), an aryl group, a heterocyclic group, or a salt-forming cation; R$^3$ is hydrogen, lower alkyl, aryl, or a salt-forming cation; Y$^1$ and Y$^2$ are each independently hydrogen, halogen (e.g., F, Cl, Br, or I), lower alkyl, hydroxy, alkoxy, or aryloxy; and n is an integer from 0 to 12. Suitable therapeutic compounds for use in the invention include compounds in which both R$^1$ and R$^2$ are pharmaceutically acceptable salt-forming cations. In a particularly suitable embodiment, R$^1$, R$^2$ and R$^3$ are each independently a sodium, potassium or calcium cation, and n is 0. In certain embodiments of the therapeutic compounds, Y$^1$ and Y$^2$ are each hydrogen. Suitable therapeutic compounds include salts of phosphonoformate. Trisodium phosphonoformate (foscarnet sodium or Foscavir®) is commercially available (e.g., from Astra), and its clinical pharmacology has been investigated (see, e.g., "Physician's Desk Reference", 51st Ed., pp. 541–545 (1997)).

In another embodiment, the therapeutic compound used in the invention can be an aminophosphonate, a biphosphonate, a phosphonocarboxylate derivative, a phosphonate derivative, or a phosphono carbohydrate. For example, the therapeutic compound can be one of the compounds described in Appendix A submitted herewith.

Suitable therapeutic compounds for inclusion in a pharmaceutical composition for treating glycosaminoglycan-associated molecular interactions include 1,3-propanedisulfonic acid, 3-amino-1-propanesulfonic acid, 3-dimethylamino-1-propanesulfonic acid sodium salt, 2-(3-sulfopropyl)-1,2,3,4-tetrahydro-9H-pyrido[3,4-b]indole, sodium salt, 3-[2-(6-methoxy-1,2,3,4-tetrahydroisoquinolinyl)]-1-propanesulfonic acid, 3-(2-hydroxyethyl)amino-1-propanesulfonic acid, 3-(3-hydroxy-1-propyl)amino-1-propanesulfonic acid, (−)3-[(R)-2-hydroxy-1-propyl]amino-1-propanesulfonic acid, 3-(4-hydroxy-1-butyl)amino-1-propanesulfonic acid, 3-(5-hydroxy-1-pentyl)amino-1-propanesulfonic acid, 3-(6-hydroxy-1-hexyl)amino-1-propanesulfonic acid, 3-(2-hydroxyethyl)amino-1-propanesulfonic acid, 3-(2-hydroxyethyl)amino-1-propanesulfonic acid, 3-(2-hydroxyethyl)amino-1-propanesulfonic acid, 3-(2-hydroxyethyl)amino-1-propanesulfonic acid, 3-hexylamino-1-propanesulfonic acid, 3-undecylamino-1-propanesulfonic acid, and 3-octadecylamino-1-propanesulfonic acid, and pharmaceutically acceptable salts or esters thereof.

In the methods of the invention, a condition related to a glycosaminoglycan-associated molecular interaction in a subject is treated by administering a therapeutic compound of the invention to the subject. The term "subject" is intended to include living organisms in which conditions related to glycosaminoglycan-associated molecular interactions can occur. The term subject is also intended to include those living organisms which are afflicted by infectious agents which secrete components which interfere with a host cells via glycosaminoglycans. Examples of subjects include humans, monkeys, cows, sheep, goats, dogs, cats, mice, rats, and transgenic species thereof. Administration of the compositions of the present invention to a subject to be treated can be carried out using known procedures, at dosages and for periods of time effective to treat a condition related to a glycosaminoglycan-associated molecular interaction in the subject. An effective amount of the therapeutic compound necessary to achieve a therapeutic effect may vary according to factors such as the age, sex, and weight of the subject, and the ability of the therapeutic compound to treat the foreign agents in the subject. Dosage regimens can be adjusted to provide the optimum therapeutic response. For example, several divided doses may be administered daily or the dose may be proportionally reduced as indicated by the exigencies of the therapeutic situation. A non-limiting example of an effective dose range for a therapeutic compound of the invention (e.g., poly(vinylsulfonate sodium salt)) is between 5 and 500 mg/kg of body weight/per day. In an aqueous composition, suitable concentrations for the active compound (i.e., the therapeutic compound that can treat the disease) are between 5 and 500 mM, between 10 and 100 mM, and between 20 and 50 mM.

The therapeutic compounds of the invention may be administered orally. Alternatively, the active compound may be administered by other suitable routes such subcutaneous, intravenous, intraperitoneal, etc. administration (e.g. by injection). Depending on the route of administration, the active compound may be coated in a material to protect the compound from the action of acids and other natural conditions which may inactivate the compound.

The compounds of the invention can be formulated to ensure proper distribution in vivo. For example, the blood-brain barrier (BBB) excludes many highly hydrophilic compounds. To ensure that the therapeutic compounds of the invention cross the BBB, they can be formulated, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs ("targeting moieties"), thus providing targeted drug delivery (see, e.g., V. V. Ranade (1989) *J. Clin. Pharmacol.* 29:685). Exemplary targeting moieties include folate or biotin (see, e.g., U.S. Pat. No. 5,416,016 to Low et al.); mannosides (Umezawa et al., (1988) *Biochem. Biophys. Res. Commun.* 153:1038); antibodies (P. G. Bloeman et al. (1995) *FEBS Lett.* 357:140; M. Owais et al. (1995) *Antimicrob. Agents Chemother.* 39:180); surfactant protein A receptor (Briscoe et al. (1995) *Am. J. Physiol.* 1233:134); gp1120 (Schreier et al. (1994) *J. Biol. Chem.* 269:9090); see also K. Keinanen; M. L. Laukkanen (1994) *FEBS Lett.* 346:123; J. J. Killion; I. J. Fidler (1994) *Immunomethods* 4:273. In an embodiment, the therapeutic compounds of the invention are formulated in liposomes; in a more preferred embodiment, the liposomes include a targeting moiety.

Delivery and in vivo distribution can also be affected by alteration of an anionic group of compounds of the invention. For example, anionic groups such as carboxylate or tetrazole can be employed instead of, or in addition to, sulfate or sulfonate moieties, to provide compounds with desirable pharmocokinetic, pharmacodynamic, biodistributive, or other properties. Exemplary tetrazole-substituted compounds include 3-(1H-tetrazol-5-yl)-9H-thioxanthen-9-one 10,10-dioxide (LXIV), 5,5-dithiobis(1-phenyltetrazole) (LXV), 1H-tetrazole (LXVI), 5-phenyl-1H-tetrazole (LXVII), and 5-(2-aminoethanoic acid)-1H-tetrazole (LXVIII), and the like; and their pharmaceutically acceptable salts. Exemplary carboxylate-substituted compounds include dicarboxylic acids such as adipic acid, azelaic acid, 3,3-imethylglutaric acid, suberic acid, succinic acid, and the like, and their harmaceutically acceptable salts.

To administer the therapeutic compound by other than parenteral administration, it may be necessary to coat the compound with, or co-administer the compound with, a material to prevent its inactivation. For example, the therapeutic compound may be administered to a subject in an appropriate carrier, for example, liposomes, or a diluent. Pharmaceutically acceptable diluents include saline and aqueous buffer solutions. Liposomes include water-in-oil-in-water CGF emulsions as well as conventional liposomes (Strejan et al., (1984) *J. Neuroimmunol.* 7:27).

The therapeutic compound may also be administered parenterally, intraperitoneally, intraspinally, or intracerebrally. Dispersions can be prepared in glycerol, liquid polyethylene glycols, and mixtures thereof and in oils. Under ordinary conditions of storage and use, these preparations may contain a preservative to prevent the growth of microorganisms.

Pharmaceutical compositions suitable for injectable use include sterile aqueous solutions (where water soluble) or dispersions and sterile powders for the extemporaneous preparation of sterile injectable solutions or dispersion. In all cases, the composition must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, sodium chloride, or polyalcohols such as mannitol and sorbitol, in the composition. Prolonged absorption of the injectable compositions can be brought about by including in the composition an agent which delays absorption, for example, aluminum monostearate or gelatin.

Sterile injectable solutions can be prepared by incorporating the therapeutic compound in the required amount in an appropriate solvent with one or a combination of ingredients enumerated above, as required, followed by filtered sterilization. Generally, dispersions are prepared by incorporating the therapeutic compound into a sterile carrier which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient (i.e., the therapeutic compound) plus any additional desired ingredient from a previously sterile-filtered solution thereof.

The therapeutic compound can be orally administered, for example, with an inert diluent or an assimilable edible carrier. The therapeutic compound and other ingredients may also be enclosed in a hard or soft shell gelatin capsule, compressed into tablets, or incorporated directly into the subject's diet. For oral therapeutic administration, the therapeutic compound may be incorporated with excipients and used in the form of ingestible tablets, buccal tablets, troches, capsules, elixirs, suspensions, syrups, wafers, and the like. The percentage of the therapeutic compound in the compositions and preparations may, of course, be varied. The amount of the therapeutic compound in such therapeutically useful compositions is such that a suitable dosage will be obtained.

It is especially advantageous to formulate parenteral compositions in dosage unit form for ease of administration and uniformity of dosage. Dosage unit form as used herein refers to physically discrete units suited as unitary dosages for the subjects to be treated; each unit containing a predetermined quantity of therapeutic compound calculated to produce the desired therapeutic effect in association with the required pharmaceutical carrier. The specification for the dosage unit forms of the invention are dictated by and directly dependent on (a) the unique characteristics of the therapeutic compound and the particular therapeutic effect to be achieved, and (b) the limitations inherent in the art of compounding such a therapeutic compound for the treatment of a condition related to a glycosaminoglycan-associated molecular interaction in a subject.

Active compounds are administered at a therapeutically effective dosage sufficient to treat a condition related to a glycosaminoglycan-associated molecular interaction in a subject. A "therapeutically effective dosage" preferably reduces the amount of symptoms of the condition in the infected subject by at least about 20%, more preferably by at least about 40%, even more preferably by at least about 60%, and still more preferably by at least about 80% relative to untreated subjects. For example, the ability of a compound to reduce an infectious agent can be evaluated in an animal model system that may be predictive of efficacy in treating diseases associated with the infectious agent in humans.

The invention is further illustrated by the following Exemplification, which should not be construed as further limiting the subject invention. The contents of all references, issued patents, and published patent applications cited throughout this is application including the background are hereby incorporated by reference.

EXEMPLIFICATION

Bacteria:

Streptococcus pyogens:

S. *pyogenes* can cause acute rheumatic fever streptococcus and acute post-streptococcal glomerulonephritis. Studies have identified the protein responsible for stabilizing the bacteria on the basal laminae of cardiac muscle as well as on kidney tissues.

The mechanism for such a bacterial virulence is unknown. One hypothesis is the direct binding of bacterial adhesions and exotoxins to the cardiac muscle and kidney Bergey & Stenson identified two streptococcal proteins (9, 15 Kda) that are capable of binding to basement membranes of cardiac muscle and renal tissues; the binding was completely inhibited by heparin and other GAGs. Binding of specific *S. pyogenes* protein can be measured on cardiac muscle section and kidney section. Briefly, *S. pyogenes* protein preparation are incubated on cardiac muscle and kidney preparation. Binding of protein is visualized by indirect immunofluorescence using an antibody against the bacteria protein. Ability of a compound to interfere in such a binding can be determined in ligand inhibition studies. Binding is measured by comparing the amount of protein binding (as determined by Image Analysis) in presence or absence of the compound. Measurement can also be determined using 3H-labeled streptococcal protein.

Fluorescence: Cryostat-cut section of heart tissue are pre-incubated with bacterial antigen preparation. Amount of peptide binding to tissue is determined by indirect immunofluorescence using a Rabbit anti-S. pyogenes serum. Ability of a compound to inhibit the binding of the streptococcal protein to the tissue is evaluated by comparing the amount of bacterial antigen present of tissue section in presence or absence of the inhibitor.

Direct Binding Assay: Radiolabelled streptococcal components are tested for direct binding activity to mammalian tissue component as previously described (M W Stinson & E J Bergey, 1982). Dried cardiac muscle fragments are rehydrated with PBS and 1% bovine serum albumin. Moist heart material is incubated with radiolabelled bacterial components. Bound radioactivity is determined by liquid scintillation spectrometry.

Determination of a compound's ability to inhibit this binding is done with various concentrations of the compound added to the streptococcal preparation prior its incubation with the cardiac muscle preparation.

S. *aureus*, Pseudomonas aeruglnosa, Legionella pneumophila

S. *aureus* and P. *aeruginosa* are well-known to cause major pulmonary infection in patients with cystic fibrosis. *Legionella pneumophila* is known to cause Legionnaire's disease in susceptible individuals. These bacteria need to adhere to mucus membrane to in order to multiply and cause infection.

The ability of specific compounds to inhibit S. *Aureus*, P. *Aeruginosa* and L. *pneumophila* adherence to mucosal membrane can be determined in vitro using murine trachea culture. The number of bacteria adhering to the preparation can be determined by comparing the number of bacteria remaining in supernatant after incubation with trachea preparation. Briefly, trachea preparation are incubated with a bacterial suspension in presence or absence of a compound. 30 minutes later the amount of bacteria remaining the supernatant (i.e., non-adhering) determined by serial dilution.

The ability of bacteria to infect cells an also be determined in vitro. Macrophages are incubated with bacteria and the phagocytic rate is determined 30 minutes later.

In vivo: Intratracheal infection with P. *aeruginosa* or S. *aureus* with or without treatment with compound. Intratracheal infection with P. *aeruginosa*, S. *aureus* and Legionella have been shown to cause acute pulmonary infection in mice. The ability of a compound to inhibit such an infection can be determined by evaluating the bacterial load present in the lung of infected mice undergoing a treatment with specific compounds. These compounds can be administered IV, PO, or under aerosol.

Viral infections:

The infectious process of viruses of the herpesviridae family have been extensively studied. It has been established that the initial interaction of several herpes viruses with the cell surface is mediated by glycosaminoglycans found on the proteoglycans in the cell plasma membrane. These GAGs are similar to heparin. Amongst the different herpes viruses found to interact with cell surface GAGs, interesting ones are Cytomegalovirus (CMV) and Herpes simplex (HSV-1 and HSV-2). The ability of compounds to interfere in the infectious process of these viruses is determined as follows:

In vitro: Hela cells are infected with CMV or HSV-1 in presence or absence of compounds. Ability of CMV to infect cells is determined by evaluating virus load 24–72 hours later by:

% viral antigen expression (IF)

specific viral antigen (mRNA level)

Virus particle titration cytopathic effect

The ability of a compound to interfere in the infectious process can be determined by evaluating (by the different techniques mentioned above) the amount of virus found in the culture in presence or absence of an inhibitor.

EQUIVALENTS

Those skilled in the art will recognize, or be able to ascertain using no more than routine experimentation, numerous equivalents to the specific procedures described herein. Such equivalents are considered to be within the scope of this invention and are covered by the following claims.

-42-

Appendix A

AMINOPHONATES

| Name | Structure |
|---|---|
| 3-[2-(1,2,3,4-Tetrahydroisoquinolinyl)]-1-propanephosphonic acid, disodium salt | 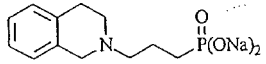 |
| 3-Aminopropylphosphonic acid | $NH_2CH_2CH_2CH_2PO_3H_2$ |
| (S)-2-Amino-2-methyl-4-phosphonobutanoic acid | 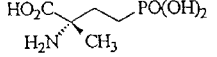 |
| D-(-)-2-Amino-4-phosphonobutanoic acid | 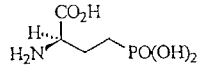 |
| L-(+)-2-Amino-4-phosphonobutanoic acid | 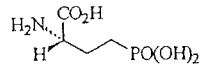 |
| 3-Aminopropyl(methyl)phosphinic acid, hydrochloride | 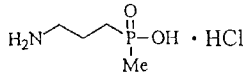 |
| (R)-(-)-3-(2-Carboxypiperazin-4-yl)-propyl-1-phosphonic acid (D-CPP) | 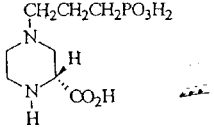 |
| (R,E)-4-(3-Phosphonoprop-2-enyl)piperazine-2-carboxylic acid | 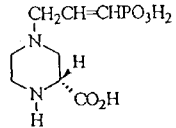 |

-43-

| | |
|---|---|
| *trans*-L-4-Phosphonomethylproline, trisodium salt | 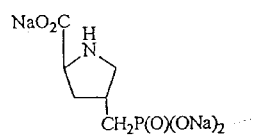 |
| *cis*-L-4-Phosphonomethylproline, trisodium salt | 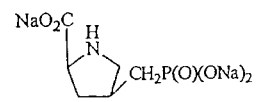 |
| 4-Amino-1-butylphosphonic acid, disodium salt | 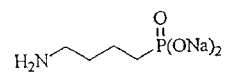 |
| 1-(3-Phosphonopropyl)-benzimidazole, disodium salt | 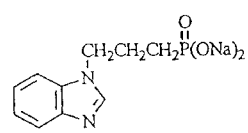 |
| 3-Dimethylamino-1-propylphosphonic acid, disodium salt | 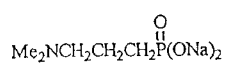 |
| 3-Amino-butylphosphonic acid, disodium salt | 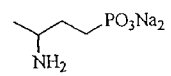 |
| 3-Amino-pentylphosphonic acid, disodium salt | 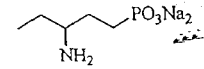 |
| 3-Amino-hexylphosphonic acid, disodium salt | 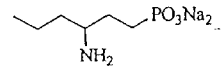 |

-44-

| | |
|---|---|
| 3-Amino-heptylphosphonic acid, disodium salt | 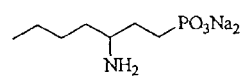 |
| 3-Amino-octylphophonic acid, disodium salt | 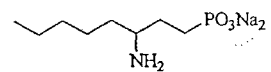 |
| 3-Amino-4-methyl-pentylphosphonic acid, disodium salt | 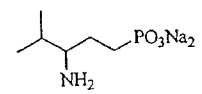 |
| 3-Amino-3-methyl-butylphosphonic acid, disodium salt | 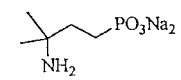 |
| 3-Amino-3-phenyl-propylphosphonic acid, disodium salt | 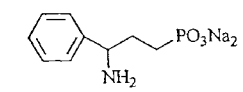 |
| 3-Amino-4-phenyl-butylphosphonic acid, disodium salt | 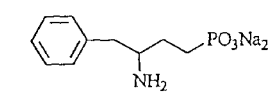 |
| 3-Amino-4-phenyl-pentylphosphonic acid, disodium salt | 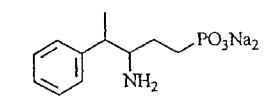 |
| 3-Amino-3-phenyl-butylphosphonic acid, disodium salt | 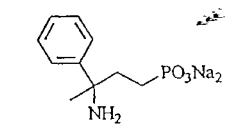 |

-45-

| | |
|---|---|
| 2-Amino-2-(2-phosphonoethyl)-1,3,4-trihydronaphthalene, disodium salt | 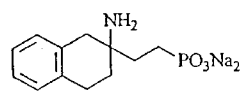 |
| 1-Amino-1-(2-phosphonoethyl)-cyclohexane, disodium salt | 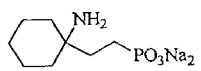 |
| 2-(2-Amino-4-phosphonobutoxy)tetrahydropyran | 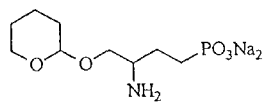 |
| 3-Amino-4-hydroxy-butylphosphonic acid, disodium salt | 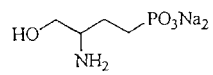 |
| Diethyl 2-pyrrolidinylphosphonate | 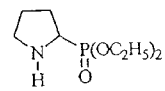 |
| 2-Pyrrolidinylphosphonic acid, disodium salt | 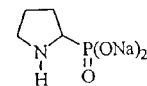 |
| 1,1-Dioxo-2-(3-phosphonopropyl)-isothiazoline, disodium salt | 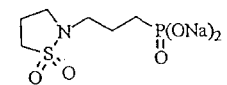 |
| 2-Deoxy-2-phosphonoacetylamino-D-glucose | 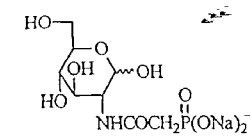 |

3-Hydroxy-3-(2-pyridyl)propenyl-2-phosphonic acid, disodium salt
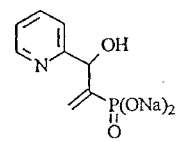
3-Hydroxy-3-(3-pyridyl)propenyl-2-phosphonic acid, disodium salt
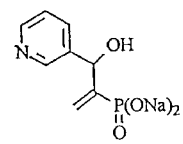
3-Hydroxy-3-(4-pyridyl)propenyl-2-phosphonic acid, disodium salt
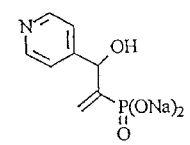
3-Amino-3-(2-pyridyl)propenyl-2-phosphonic acid, disodium salt
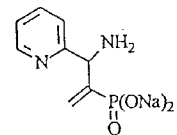
3-Amino-3-(3-pyridyl)propenyl-2-phosphonic acid, disodium salt
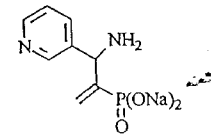

-47-

| | |
|---|---|
| 3-Amino-3-(4-pyridyl)propenyl-2-phosphonic acid, disodium salt | 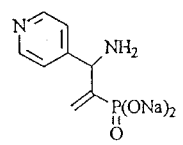 |
| 1,4-Diamino-1-(3-pyridyl)butyl-2-phosphonic acid, disodium salt | 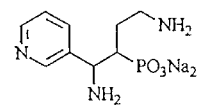 |
| 1,4-Diamino-4-methyl-1-(3-pyridyl)pentyl-2-phosphonic acid, disodium salt | 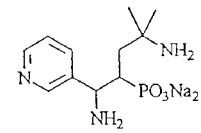 |
| 1,4-Diamino-4-methyl-1-(2-pyridyl)pentyl-2-phosphonic acid, disodium salt | 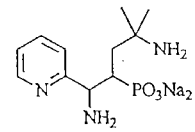 |
| 1,4-Diamino-4-methyl-1-(4-pyridyl)pentyl-2-phosphonic acid, disodium salt | 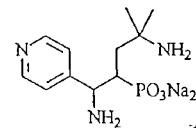 |
| 3-(2-Amino-4,5,7,8-tetrahydro-6$H$-thiazolo[4,5-$d$]azepin-6-yl)propyl-phosphonic acid, disodium salt | 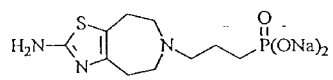 |

-48-

| | |
|---|---|
| N-Phosphonomethylglycine | (HO)₂P(O)CH₂NHCH₂COOH |
| N-Phosphonomethylglycine, trisodium salt | (NaO)₂P(O)CH₂NHCH₂COONa |
| (2R,4S)-4-Phosphonomethylpipecolinic acid, trisodium salt | 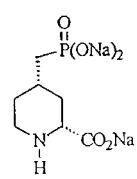 |
| (2R,4S)-4-Phosphonomethyl-pipecolinamide, disodium salt | 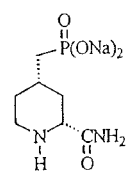 |
| N-Phosphonomethylglycine (Aldrich, see NC-1769) | (HO)₂P(O)CH₂NHCH₂COOH |
| N-Phosphonomethylglycine, trisodium salt (see NC1770, prepared from NC1781) | (NaO)₂P(O)CH₂NHCH₂COONa |
| 3-[6-Methoxy-2-(1,2,3,4-tetrahydro-isoquinolinyl)]propylphosphonic acid, disodium salt | 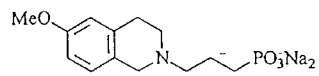 |

-49-
| | |
|---|---|
| 3-[8-Methoxy-2-(1,2,3,4-tetrahydro-isoquinolinyl)]propylphosphonic acid, disodium salt | 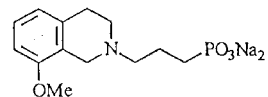 |
| 3-[2-(3-Methoxycarbonyl-1,2,3,4-tetrahydroisoquinolinyl)]-propylphosphonic acid disodium salt | 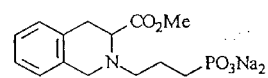 |
| 2-(3-Phosphonopropyl)-1,2,3,4-tetrahydro-9H-pyrido[3,4-b]indole, disodium salt | 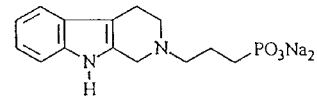 |

-50-

Bisphosphonates

| Name | Structure |
|---|---|
| Pamidronic acid (3-Aminopropyl-1-hydroxypropane-1,1-bisphosphonic acid) | 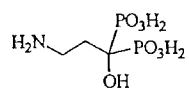 |
| 3-Amino-1-hydroxypropane-1,1-bisphosphonic acid, tetrasodium salt | 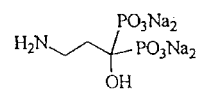 |
| 1-Amino-3-sulfopropane-1,1-bisphosphonic acid | 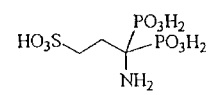 |
| 1-Amino-3-sulfopropane-1,1-bisphosphonic acid, pentasodium salt | 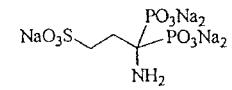 |
| 1,3-Diaminopropane-1,1-bisphosphonic acid, tetrasodium salt | 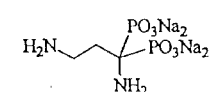 |
| 1-Amino-3-dimethylaminopropane-1,1-bisphosphonic acid, tetrasodium salt | 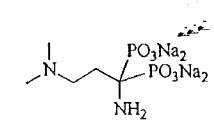 |
| 3-Dimethylamino-1-hydroxypropane-1,1-bisphosphonic acid, tetrasodium salt | 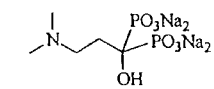 |

-51-

| | |
|---|---|
| 1-Hydroxy-3-(methylphenylamino)-propane-1,1-bisphosphonic acid, tetrasodium salt | 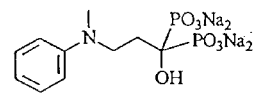 |
| 1-Amino-3-(methylphenylamino)propane-1,1-bisphosphonic acid, tetrasodium salt | 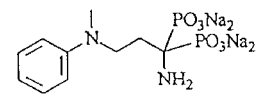 |
| Ibandronic acid, tetrasodium salt (1-Hydroxy-3-(methylpentylamino)-propane-1,1-bisphosphonic acid, tetrasodium salt) | 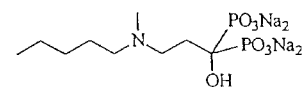 |
| 1-Amino-3-(methylpentylamino)propane-1,1-bisphosphonic acid, tetrasodium salt | 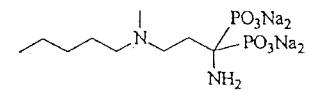 |
| 1-Amino-3-(1-benzimidazolyl)propane-1,1-bisphosphonic acid | 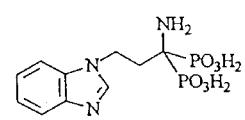 |
| 1-Amino-3-(1-benzimidazolyl)propane-1,1-bisphosphonic acid, tetrasodium salt | 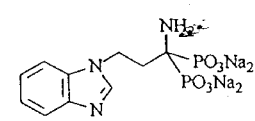 |
| 3-Aminopropane-1,1-bisphosphonic acid, tetrasodium salt | 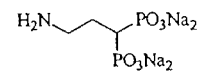 |

-52-

(*dl*)-3-Aminobutane-1,1-bisphosphonic acid, tetrasodium salt
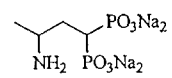

(*dl*)-3-Aminopentane-1,1-bisphosphonic acid, tetrasodium salt
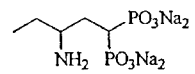

(*dl*)-3-Aminohexane-1,1-bisphosphonic acid, tetrasodium salt
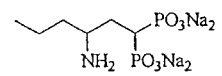

(*dl*)-3-Aminoheptane-1,1-bisphosphonic acid, tetrasodium salt
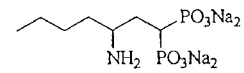

(*dl*)-3-Aminooctane-1,1-bisphosphonic acid, tetrasodium salt
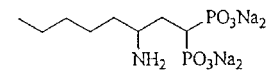

(*dl*)-3-Amino-4-methylpentane-1,1-bisphosphonic acid, tetrasodium salt
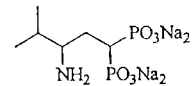

(*dl*)-3-Amino-3-methylbutane-1,1-bisphosphonic acid, tetrasodium salt
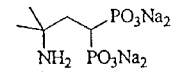

(*dl*)-3-Amino-3-phenylpropane-1,1-bisphosphonic acid, tetrasodium salt
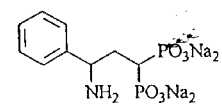

(*dl*)-3-Amino-4-phenylbutane-1,1-bisphosphonic acid, tetrasodium salt
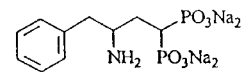

-53-

| | |
|---|---|
| (dl)-3-Amino-4-phenylpentane-1,1-bisphosphonic acid, tetrasodium salt | 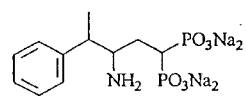 |
| (dl)-3-Amino-3-phenylbutane-1,1-bisphosphonic acid, tetrasodium salt | 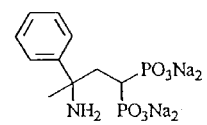 |
| (dl)-2-(2-Amino-1,2,3,4-tetrahydronaphthalenyl)ethane-1,1-bisphosphonic acid, tetrasodium salt | 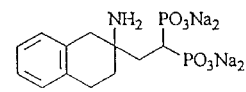 |
| 2-(1-Aminocyclohexyl)ethane-1,1-bisphosphonic acid, tetrasodium salt | 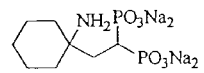 |
| 2-(2-Amino-4,4-bisphosphonobutoxy)-tetrahydropyran, tetrasodium salt | 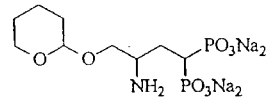 |
| (dl)-3-Amino-4-hydroxybutane-1,1-bisphosphonic acid, tetrasodium salt | 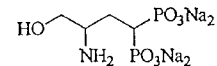 |
| (S)-Hydroxy(2-pyrrolidinyl)methanebisphosphonic acid tetrasodium salt | 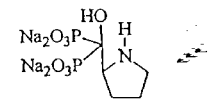 |
| Hydroxy[(2S,4R)-4-hydroxy-2-pyrrolidinyl]methanebisphosphonic acid tetrasodium salt | 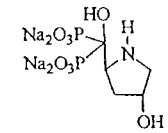 |

| | |
|---|---|
| 2-Amino-1-hydroxyethane-1,1-bisphosphonic acid, tetrasodium salt | 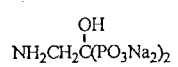 |
| 1,2-Diaminoethane-1,1-bisphonponic acid, tetrasodium salt | 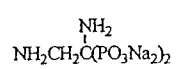 |
| 4-Amino-1-hydroxybutane-1,1-bisphosphonic acid, tetrasodium salt |  |
| 1,4-Diaminobutane-1,1-bisphosphonic acid, tetrasodium salt | 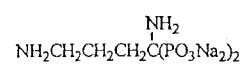 |
| 5-Amino-1-hydroxypentane-1,1-bisphosphonic acid, tetrasodium salt | 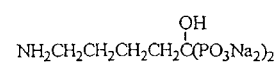 |
| 1,5-Diaminopentane-1,1-bisphosphonic acid, tetrasodium salt | 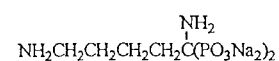 |
| (S)-2-Amino-1-hydroxypropane-1,1-bisphosphonic acid, tetrasodium salt | 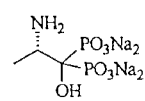 |
| (S)-2-Amino-1-hydroxybutane-1,1-bisphosphonic acid, tetrasodium salt | 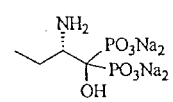 |
| (S)-2-Amino-1-hydroxy-3-methylbutane-1,1-bisphosphonic acid, tetrasodium salt | 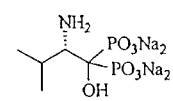 |

-55-

| | |
|---|---|
| (S)-2-Amino-1-hydroxy-3-phenylpropane-1,1-bisphosphonic acid, tetrasodium salt | 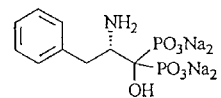 |
| (S)-2-Amino-1,3-dihydroxypropane-1,1-bisphosphonic acid, tetrasodium salt | 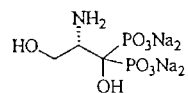 |
| (S)-2,3-Diamino-1-hydroxypropane-1,1-bisphosphonic acid, tetrasodium salt | 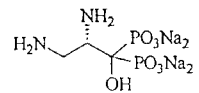 |
| (dl)-3-Amino-1-hydroxy-3-phenylpropane-1,1-bisphosphonic acid, tetrasodium salt | 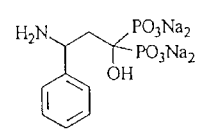 |
| (S)-3-Amino-2-(4-chlorophenyl)-1-hydroxypropane-1,1-bisphosphonic acid, tetrasodium salt | 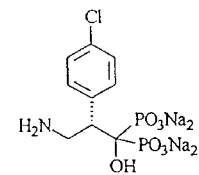 |
| (S)-2-Amino-3-(4-aminophenyl)-1-hydroxypropane-1,1-bisphosphonic acid, tetrasodium salt | 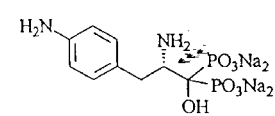 |

Phosphonocarboxylate Derivatives
| Name | Structure |
|---|---|
| Phosphonoacetic acid (fosfonet) | 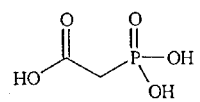 |
| Phosphonoformic acid, trisodium salt | 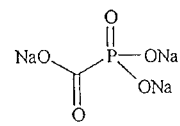 |
| Diethylphosphonoacetic acid | 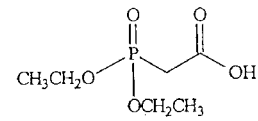 |
| 2-Carboxyethylphosphonic acid | $HO_2CCH_2CH_2PO_3H_2$ |
| (dl)-2-Amino-3-phosphonopropanoic acid | 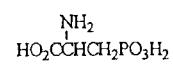 |
| (dl)-2-Amino-5-phosphonopentanoic acid | 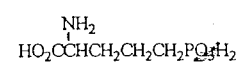 |
| Phosphonoacetic acid (See NC-769) | $HO_2CCH_2PO_3H_2$ |
| (S)-2-Amino-2-methyl-4-phosphonobutanoic acid | 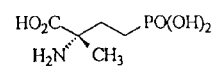 |

-57-
| | |
|---|---|
| D-(−)-2-Amino-4-phosphonobutanoic acid | 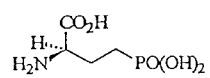 |
| L-(+)-2-Amino-4-phosphonobutanoic acid | 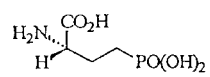 |
| D-(−)-2-Amino-7-phosphonoheptanoic acid | 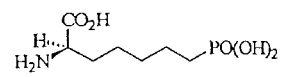 |
| L-(+)-2-Amino-7-phosphonoheptanoic acid | 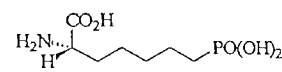 |
| D-(−)-2-Amino-6-phosphonohexanoic acid | 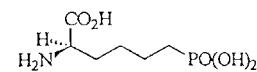 |
| L-(+)-2-Amino-6-phosphonohexanoic acid | 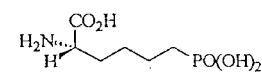 |
| D-(−)-2-Amino-4-phosphonopentanoic acid | 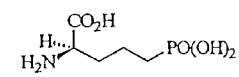 |
| L-(+)-2-Amino-4-phosphonopentanoic acid | 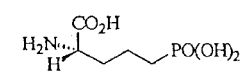 |
| D-(−)-2-Amino-3-phosphonopropanoic acid | 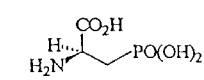 |
| L-(+)-2-Amino-3-phosphonopropanoic acid | 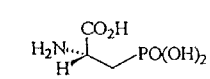 |

-58-
(R)-(-)-3-(2-Carboxypiperazin-4-yl)-propyl-1-phosphonic acid (D-CPP) 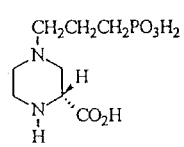
L-4-[Difluoro(phosphono)methyl)]-phenylalanine 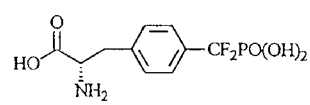
(R,E)-4-(3-Phosphonoprop-2-enyl)piperazine-2-carboxylic acid 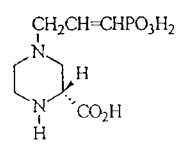
trans-L-4-Phosphonomethylproline, trisodium salt 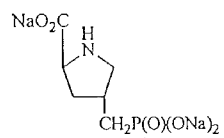
cis-L-4-Phosphonomethylproline, trisodium salt 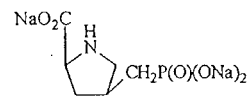
N,N-Diethylphosphonoacetamide, disodium salt 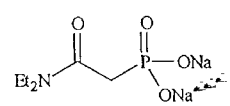
N-Cyclohexylphosphonoacetamide, disodium salt 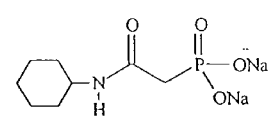

-59-
| | |
|---|---|
| Phosphonoacetic hydrazide, disodium salt | 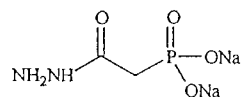 |
| *N*-Hydroxyphosphonoacetamide, disodium salt | 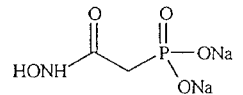 |
| *N*-Phosphonoacetyl-L-alanine, trisodium salt | 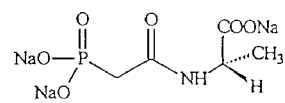 |
| *N*-Phosphonoacetyl-L-glycine, trisodium salt | 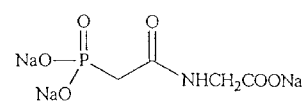 |
| *N*-(Phosphonoactyl)-L-asparagine-L-glycine, tetrasodium salt | 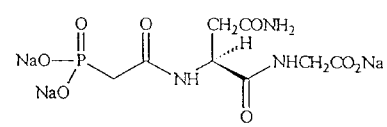 |
| *N*-Phosphonomethylglycine | 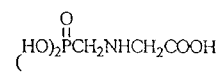 |
| *N*-Phosphonomethylglycine, trisodium salt | 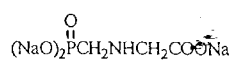 |
| 2-Phosphonomethylglutaric acid, tetrasodium salt | 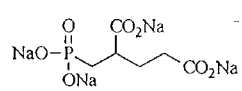 |

-60-
| | |
|---|---|
| 2-Phosphonomethylsuccinic acid, tetrasodium salt | 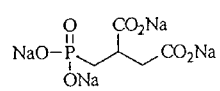 |
| (2R,4S)-4-Phosphonomethylpipecolinic acid, trisodium salt | 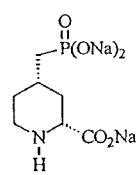 |
| (2R,4S)-4-Phosphonomethyl-pipecolinamide, disodium salt | 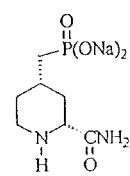 |
| N-Phosphonomethylglycine (Aldrich, see NC-1769) | 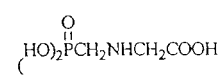 |
| N-Phosphonomethylglycine, trisodium salt (see NC1770, prepared from NC1781) | 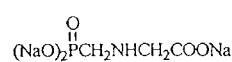 |
| 3-[2-(3-Methoxycarbonyl-1,2,3,4-tetrahydroisoquinolinyl)]-propylphosphonic acid disodium salt | 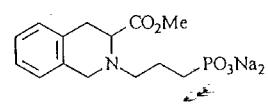 |

-61-

Phosphonate derivative

| Name | Structure |
|---|---|
| 3-[2-(1,2,3,4-Tetrahydroisoquinolinyl)]-1-propanephosphonic acid, disodium salt | 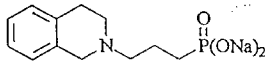 |
| Propylphosphonic acid | $CH_3CH_2CH_2PO_3H_2$ |
| Ethylphosphonic acid | $CH_3CH_2PO_3H_2$ |
| Methylphosphonic acid | $CH_3PO_3H_2$ |
| *tert*-Butylphosphonic acid | $(CH_3)_3CPO_3H_2$ |
| Phenylphosphonic acid | 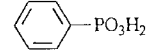 |
| 3-Aminopropylphosphonic acid | $NH_2CH_2CH_2CH_2PO_3H_2$ |
| (1-Aminopropyl)phosphonic acid | $CH_3CH_2\overset{NH_2}{\underset{}{C}H}-PO_3H_2$ |
| Diethyl phosphoramidate | 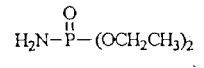 |
| 3-Aminopropyl(methyl)phosphinic acid, hydrochloride | 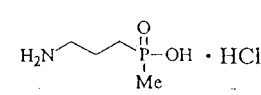 |
| 4-Amino-1-butylphosphonic acid, disodium salt | 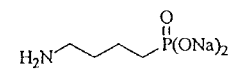 |

-62-

| | |
|---|---|
| 1-(3-Phosphonopropyl)-benzimidazole, disodium salt | 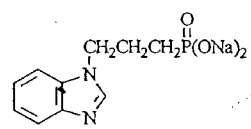 |
| 3-Dimethylamino-1-propylphosphonic acid, disodium salt | $Me_2NCH_2CH_2CH_2\overset{\overset{O}{\|}}{P}(ONa)_2$ |
| Diphenylamine-4-phosphonic acid, disodium salt | 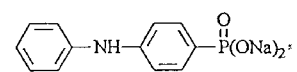 |
| 3-Amino-butylphosphonic acid, disodium salt | 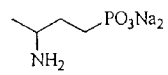 |
| 3-Amino-pentylphosphonic acid, disodium salt | 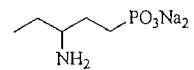 |
| 3-Amino-hexylphosphonic acid, disodium salt | 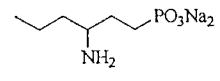 |
| 3-Amino-heptylphosphonic acid, disodium salt | 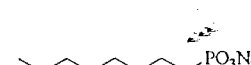 |
| 3-Amino-octylphophonic acid, disodium salt | 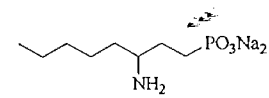 |
| 3-Amino-4-methyl-pentylphosphonic acid, disodium salt | 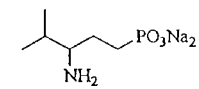 |

-63-

| | |
|---|---|
| 3-Amino-3-methyl-butylphosphonic acid, disodium salt | 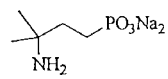 |
| 3-Amino-3-phenyl-propylphosphonic acid, disodium salt | 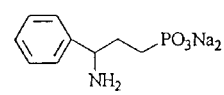 |
| 3-Amino-4-phenyl-butylphosphonic acid, disodium salt | 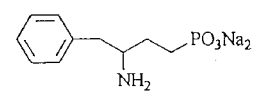 |
| 3-Amino-4-phenyl-pentylphosphonic acid, disodium salt | 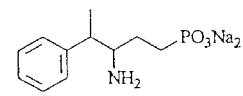 |
| 3-Amino-3-phenyl-butylphosphonic acid, disodium salt | 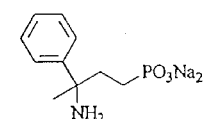 |
| 2-Amino-2-(2-phosphonoethyl)-1,3,4-trihydronaphthalene, disodium salt | 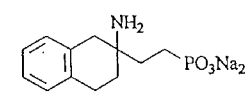 |
| 1-Amino-1-(2-phosphonoethyl)-cyclohexane, disodium salt | 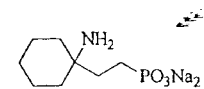 |
| 2-(2-Amino-4-phosphonobutoxy)tetrahydropyran | 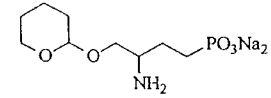 |

-64-
| 3-Amino-4-hydroxy-butylphosphonic acid, disodium salt | 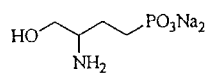 |
| 3-Phosphonopropanesulfonic acid, trisodium salt | 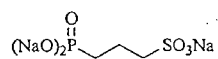 |
| Diethyl 2-pyrrolidinylphosphonate | 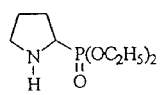 |
| 2-Pyrrolidinylphosphonic acid, disodium salt | 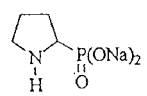 |
| 1,1-Dioxo-2-(3-phosphonopropyl)-isothiazoline, disodium salt | 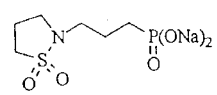 |
| 2-Deoxy-2-phosphonoacetylamino-D-glucose | 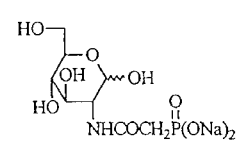 |
| 3-Hydroxy-3-(2-pyridyl)propenyl-2-phosphonic acid, disodium salt | 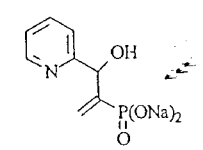 |

-65-
| | |
|---|---|
| 3-Hydroxy-3-(3-pyridyl)propenyl-2-phosphonic acid, disodium salt | 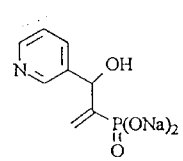 |
| 3-Hydroxy-3-(4-pyridyl)propenyl-2-phosphonic acid, disodium salt | 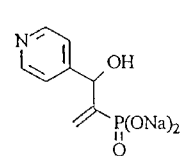 |
| 3-Amino-3-(2-pyridyl)propenyl-2-phosphonic acid, disodium salt | 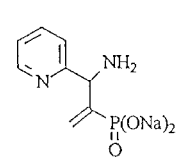 |
| 3-Amino-3-(3-pyridyl)propenyl-2-phosphonic acid, disodium salt | 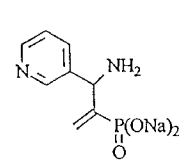 |
| 3-Amino-3-(4-pyridyl)propenyl-2-phosphonic acid, disodium salt | 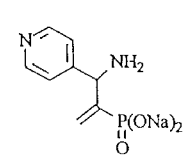 |

-66-

| | | |
|---|---|---|
| 1,4-Diamino-1-(3-pyridyl)butyl-2-phosphonic acid, disodium salt | 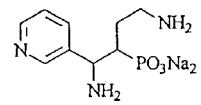 | |
| 1,4-Diamino-4-methyl-1-(3-pyridyl)pentyl-2-phosphonic acid, disodium salt | 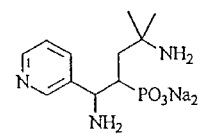 | |
| 1,4-Diamino-4-methyl-1-(2-pyridyl)pentyl-2-phosphonic acid, disodium salt | 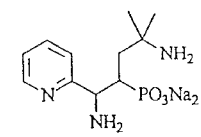 | |
| 1,4-Diamino-4-methyl-1-(4-pyridyl)pentyl-2-phosphonic acid, disodium salt | 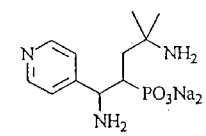 | |
| 3-(2-Amino-4,5,7,8-tetrahydro-6$H$-thiazolo[4,5-$d$]azepin-6-yl)propyl-phosphonic acid, disodium salt | 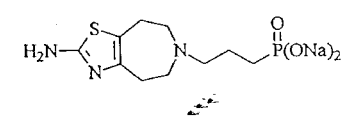 | |
| 3-[6-Methoxy-2-(1,2,3,4-tetrahydro-isoquinolinyl)]propylphosphonic acid, disodium salt | 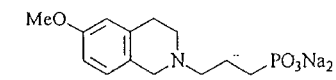 | |

-67-
| | |
|---|---|
| 3-[8-Methoxy-2-(1,2,3,4-tetrahydro-isoquinolinyl)]propylphosphonic acid, disodium salt | 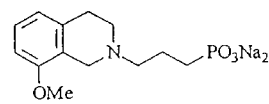 |
| 2-(3-Phosphonopropyl)-1,2,3,4-tetrahydro-9H-pyrido[3,4-b]indole, disodium salt | 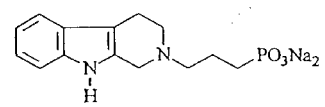 |

-68-
Phosphono Carbohydrates
| Name | Structure |
|---|---|
| 2-Deoxy-2-phosphonoacetylamino-D-glucose | 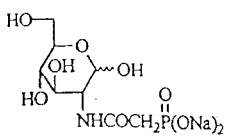 |
| 2-Deoxy-2-thiophosphonoacetylamino-D-glucose | 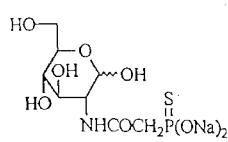 |
| β-D-Glucopyranosylmethylphosphonic acid, disodium salt | 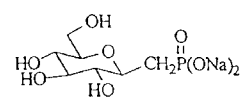 |
| α-D-Glucopyranosylmethylphosphonic acid, disodium salt | 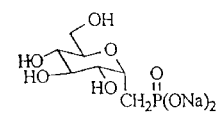 |
| 6-Deoxy-6-C-phosphonomethyl-D-glucono-δ-lactone, disodium salt | 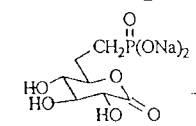 |

-69-
| | |
|---|---|
| 6-Deoxy-6-C-phosphonomethyl-D-glucose, disodium salt | 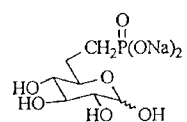 |
| 4-Deoxy-4-C-phosphonomethyl-D-glucose, disodium salt | 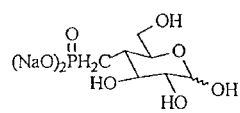 |
| 3-Deoxy-3-C-phosphonomethyl-D-glucose, disodium salt | 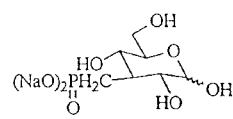 |
| 1-Deoxy-N-phosphonoacetylnojirimycin, disodium salt | 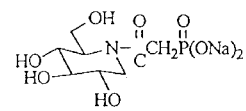 |
| (1,5-Dideoxy-1,5-imino-α-D-glucopyranosyl)methylphosphonic acid, disodium salt | 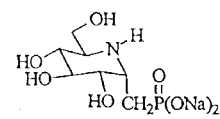 |
| 1,6-Dideoxy-6-C-phosphonomethyl-nojirimycin, disodium salt | 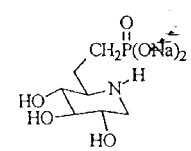 |

-70-

Thiophosphonate Derivatives

| Name | Structure |
|---|---|
| Thiophosphonoformic acid, trisodium salt | NaO-C(=O)-P(=S)(ONa)(ONa) |
| Thiophosphonoacetic acid | HO-C(=O)-CH$_2$-P(=S)(OH)(OH) |
| Thiophosphonoacetic acid, trisodium salt | NaO-C(=O)-CH$_2$-P(=S)(ONa)(ONa) |
| Thiophosphonoacetic acid, triethyl ester | EtO-C(=O)-CH$_2$-P(=S)(OEt)(OEt) |
| Chloro(thiophosphono)acetic acid, trisodium salt | NaO-C(=O)-CHCl-P(=S)(ONa)(ONa) |
| Dichloro(thiophosphono)acetic acid, trisodium salt | NaO-C(=O)-CCl$_2$-P(=S)(ONa)(ONa) |

-71-

| | |
|---|---|
| Thiophosphonomethylthiophosphonic acid, tetrasodium salt | 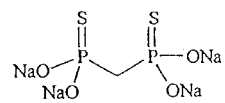 |
| Phenylthiophosphinomethylthio-phosphonic acid, trisodium salt | 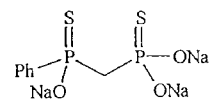 |
| 3-[2-(1,2,3,4-Tetrahydroisoquinolinyl)]-1-propanethiophosphonic acid, disodium salt | 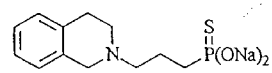 |
| Propylthiophosphonic acid | 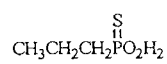 |
| Ethylthiophosphonic acid |  |
| Methylthiophosphonic acid | 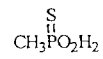 |
| tert-Butylthiophosphonic acid | 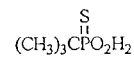 |
| 2-Carboxyethylthiophosphonic acid |  |
| Phenylthiophosphonic acid | 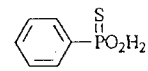 |
| 3-Aminopropylthiophosphonic acid | 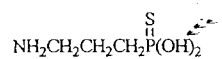 |
| (dl)-2-Amino-3-thiophosphonopropionic acid | 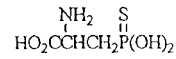 |
| (1-Aminopropyl)thiophosphonic acid | 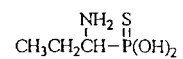 |

-72-

| | |
|---|---|
| (dl)-2-Amino-5-thiophosphonopentanoic acid | 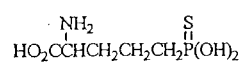 |
| (S)-2-Amino-2-methyl-4-thiophosphonobutanoic acid | 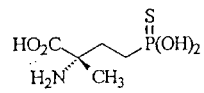 |
| D-2-Amino-4-thiophosphonobutanoic acid | 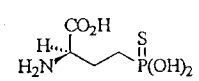 |
| L-2-Amino-4-thiophosphonobutanoic acid | 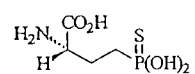 |
| D-2-Amino-7-thiophosphonoheptanoic acid | 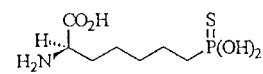 |
| L-2-Amino-7-thiophosphonoheptanoic acid | 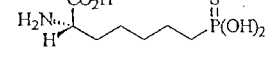 |
| D-2-Amino-6-thiophosphonohexanoic acid | 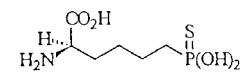 |
| L-2-Amino-6-thiophosphonohexanoic acid | 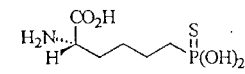 |
| D-2-Amino-4-thiophosphonopentanoic acid | 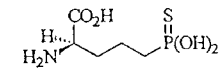 |
| L-2-Amino-4-thiophosphonopentanoic acid | 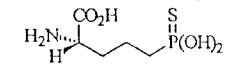 |
| D-2-Amino-3-thiophosphonopropionic acid | 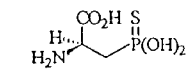 |

-73-

L-2-Amino-3-thiophosphonopropionic acid 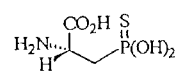

3-Aminopropyl(methyl)thiophosphinic acid, hydrochloride 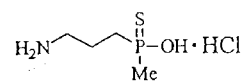

(R)-3-(2-Carboxypiperazin-4-yl)-propyl-1-thiophosphonic acid 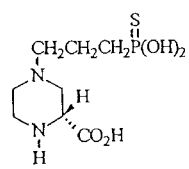

L-4-[Difluoro(thiophosphono)methyl]-phenylalanine 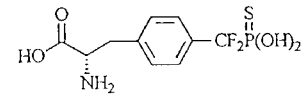

(R,E)-4-(3-Thiophosphonoprop-2-enyl)piperazine-2-carboxylic acid 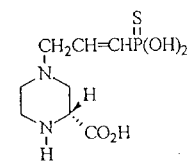

trans-L-4-Thiophosphonomethylproline, trisodium salt 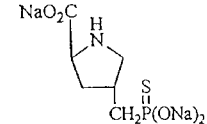

cis-L-4-Thiophosphonomethylproline, trisodium salt 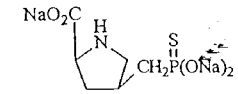

4-Amino-1-butylthiophosphonic acid, disodium salt 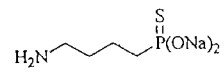

| | |
|---|---|
| 1-(3-Thiophosphonopropyl)-benzimidazole, disodium salt | 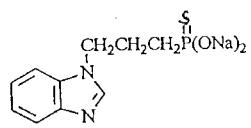 |
| 3-Dimethylamino-1-propylthiophosphonic acid, disodium salt |  |
| N,N-Diethylthiophosphonoacetamide, disodium salt | 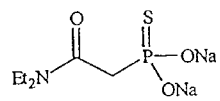 |
| Diphenylamine-4-thiophosphonic acid, disodium salt | 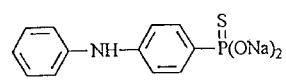 |
| Selenophosphonoformic acid, trisodium salt | 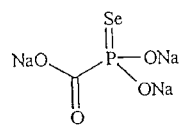 |
| Selenophosphonoacetic acid, trisodium salt | 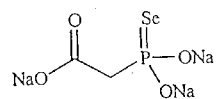 |
| D-2-Amino-3-selenophosphonopropanoic acid | 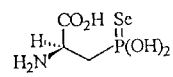 |
| L-2-Amino-3-selenophosphonopropanoic acid | 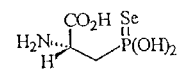 |
| D-2-Amino-4-selenophosphonobutanoic acid | 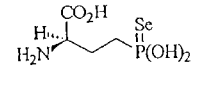 |
| L-2-Amino-4-selenophosphonobutanoic acid | 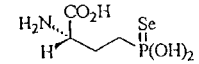 |

-75-

N-Cyclohexylthiophosphonoacetamide, disodium salt 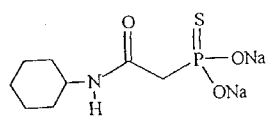

N-Cyclohexylselenophosphonoacetamide, disodium salt 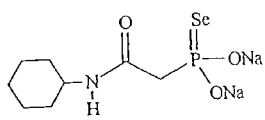

N-Hydroxythiophosphonoacetamide, disodium salt 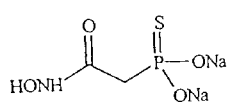

Thiophosphonoacetic hydrazide, disodium salt 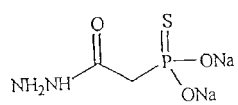

N-Thiophosphonoacetyl-L-alanine, trisodium salt 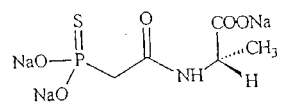

N-Thiophosphonoacetyl-L-glycine, trisodium salt 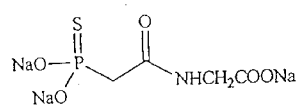

N-(Thiophosphonoactyl)-L-asparagine-L-glycine, tetrasodium salt 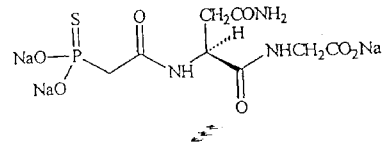

(s)-2-Pyrrolidinemethylthiophosphonic acid, disodium salt 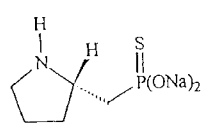

1,1-Dioxo-2-(3-thiophosphonopropyl)-
isothiazolidine, disodium salt
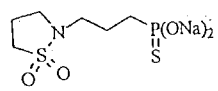
2-Deoxy-2-thiophosphonoacetylamino-D-
glucose
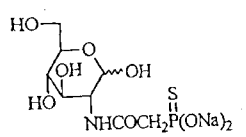
3-(2-Amino-4,5,7,8-tetrahydro-6H-
thiazolo[4,5-d]azepin-6-yl)propyl-
thiophosphonic acid, disodium salt

-77-
1,1-Dioxo-2-(3-thiophosphonopropyl)-
isothiazolidine, disodium salt
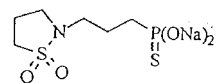
2-Deoxy-2-thiophosphonoacetylamino-D-
glucose
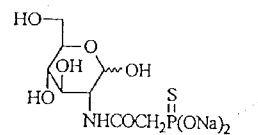
3-(2-Amino-4,5,7,8-tetrahydro-6H-
thiazolo[4,5-d]azepin-6-yl)propyl-
thiophosphonic acid, disodium salt
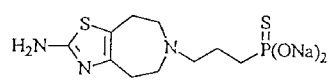

What is claimed is:

1. A method of treating a condition associated with a glycosaminoglycan-associated molecular interaction in a subject, comprising administering to a subject a therapeutically effective amount of 3-amino-1-propanesulfonic acid, or a pharmaceutically acceptable salt or ester thereof, such that said glycosaminoglycan-associated molecular interaction is modulated and said condition is treated, provided that said condition is not amyloidosis.

2. A method of treating a condition associated with a glycosaminoglycan-associated molecular interaction in a subject, comprising administering to a subject a therapeutically effective amount of 1,3-propanedisulfonic acid, or a pharmaceutically acceptable salt or ester thereof, such that said glycosaminoglycan-associated molecular interaction is modulated and said condition is treated, provided that said condition is not amyloidosis.

3. A method of treating a condition associated with a glycosaminoglycan-associated molecular interaction in a subject, comprising administering to a subject a therapeutically effective amount of 3-dimethylamino-1-propanesulfonic acid, or a pharmaceutically acceptable salt or ester thereof, such that said glycosaminoglycan-associated molecular interaction is modulated and said condition is treated, provided that said condition is not amyloidosis.

4. A method of treating a condition associated with a glycosaminoglycan-associated molecular interaction in a subject, comprising administering to a subject a therapeutically effective amount of 2-(3-sulfopropyl)-1,2,3,4-tetrahydro-9H-pyrido(3,4-bindole, or a pharmaceutically acceptable salt or ester thereof, such that said glycosaminoglycan-associated molecular interaction is modulated and said condition is treated, provided that said condition is not amyloidosis.

5. A method of treating a condition associated with a glycosaminoglycan-associated molecular interaction in a subject, comprising administering to a subject a therapeutically effective amount of 3-(2-(6-methoxy-1,2,3,4-tetrahydroisoquinolinyl))-1-propanesulfonic acid, or a pharmaceutically acceptable salt or ester thereof, such that said glycosaminoglycan-associated molecular interaction is modulated and said condition is treated, provided that said condition is not amyloidosis.

* * * * *

UNITED STATES PATENT AND TRADEMARK OFFICE
CERTIFICATE OF CORRECTION

PATENT NO. : 6,310,073 B1
DATED : October 30, 2001
INVENTOR(S) : Kisilevsky et al.

It is certified that error appears in the above-identified patent and that said Letters Patent is hereby corrected as shown below:

<u>Column 100,</u>
Line 8, delete "pyrido(3,4-bindole", and insert therefor -- pyrido(3,4-*b*)indole --.

Signed and Sealed this

First Day of October, 2002

*Attest:*

JAMES E. ROGAN
*Attesting Officer*   *Director of the United States Patent and Trademark Office*

UNITED STATES PATENT AND TRADEMARK OFFICE
CERTIFICATE OF CORRECTION

PATENT NO. : 6,310,073 B1
DATED : October 30, 2001
INVENTOR(S) : Kisilevsky et al.

It is certified that error appears in the above-identified patent and that said Letters Patent is hereby corrected as shown below:

<u>Column 99,</u>
Line 9, after the word "amyloidosis", please insert -- or infection by *Staphylococcus aureus* --

Signed and Sealed this

Twenty-seventh Day of April, 2004

JON W. DUDAS
*Acting Director of the United States Patent and Trademark Office*